(12) United States Patent
Wiltzius et al.

(10) Patent No.: US 11,834,654 B2
(45) Date of Patent: Dec. 5, 2023

(54) ANTIGEN BINDING MOLECULES AND METHODS OF USE THEREOF

(71) Applicant: Kite Pharma, Inc., Santa Monica, CA (US)

(72) Inventors: Jed J. W. Wiltzius, Santa Monica, CA (US); Stuart A. Sievers, Santa Monica, CA (US)

(73) Assignee: Kite Pharma, Inc., Santa Monica, CA (US)

( * ) Notice: Subject to any disclaimer, the term of this patent is extended or adjusted under 35 U.S.C. 154(b) by 333 days.

(21) Appl. No.: 17/094,458

(22) Filed: Nov. 10, 2020

(65) Prior Publication Data

US 2021/0130808 A1      May 6, 2021

Related U.S. Application Data

(62) Division of application No. 16/138,542, filed on Sep. 21, 2018, now Pat. No. 10,844,371.

(60) Provisional application No. 62/562,231, filed on Sep. 22, 2017.

(51) Int. Cl.
| | | |
|---|---|---|
| *C12N 15/10* | (2006.01) | |
| *C07K 16/00* | (2006.01) | |
| *A61K 47/65* | (2017.01) | |
| *A61K 31/37* | (2006.01) | |
| *C12N 15/62* | (2006.01) | |
| *C12N 15/85* | (2006.01) | |

(52) U.S. Cl.
CPC .......... *C12N 15/1037* (2013.01); *A61K 31/37* (2013.01); *A61K 47/65* (2017.08); *C07K 16/00* (2013.01); *C12N 15/1062* (2013.01); *C12N 15/62* (2013.01); *C12N 15/85* (2013.01); *C07K 2317/34* (2013.01)

(58) Field of Classification Search
None
See application file for complete search history.

(56) References Cited

U.S. PATENT DOCUMENTS

| | | | |
|---|---|---|---|
| 5,223,409 A | 6/1993 | Ladner et al. | |
| 5,225,539 A | 7/1993 | Winter | |
| 5,545,806 A | 8/1996 | Lonberg et al. | |
| 5,569,825 A | 10/1996 | Lonberg et al. | |
| 5,814,318 A | 9/1998 | Lonberg et al. | |
| 5,821,337 A | 10/1998 | Carter et al. | |
| 5,859,205 A | 1/1999 | Adair et al. | |
| 5,869,619 A | 2/1999 | Studnicka | |
| 5,877,397 A | 3/1999 | Lonberg et al. | |
| 6,180,370 B1* | 1/2001 | Queen | A61P 31/12 435/69.6 |
| 6,881,557 B2 | 4/2005 | Foote | |
| 7,709,226 B2 | 5/2010 | Foote | |
| 8,957,193 B2 | 2/2015 | Zhang et al. | |
| 10,844,371 B2* | 11/2020 | Wiltzius | C12N 15/85 |
| 2013/0287748 A1 | 10/2013 | June et al. | |

FOREIGN PATENT DOCUMENTS

| | | | |
|---|---|---|---|
| WO | 09030285 A1 | 3/2009 | |
| WO | 14106004 A2 | 7/2014 | |
| WO | 15105522 A1 | 7/2015 | |
| WO | 16160618 A2 | 10/2016 | |

OTHER PUBLICATIONS

Jakobovits et al., "Analysis of homozygous mutant chimeric mice: deletion of the immunoglobulin heavy-chain joining region blocks B-cell development and antibody production", Proc Natl Acad Sci USA 90:2551-55 (1993).
Jakobovits et al., "Germ-line transmission and expression of a human-derived yeast artificial chromosome", Nature 362:255-58 (1993).
Jakobovits et al., "Production of antigen-specific human antibodies from mice engineered with human heavy and light chain YACs", Ann. N.Y. Acad. Sci. 764:525-35 (1995).
Jakobovits, "Humanizing the mouse genome", Curr Biol. 4:761-63 (1994).
Jakobovits, "Production and selection of antigen-specific fully human monoclonal antibodies from mice engineered with human Ig loci", Advanced Drug Delivery Reviews 31:33-42 (1998).
Jakobovits, "The long-awaited magic bullets: therapeutic human monoclonal antibodies from transgenic mice" Exp. Opin. Invest. Drugs. 7:607-14 (1998).
Kang et al., "Linkage of recognition and replication functions by assembling combinatorial antibody Fab libraries along phage surfaces", Proc. Natl. Acad. Sci. USA 88:4363-66 (1991).
Kellermann et al., "Antibody discovery: the use of transgenic mice to generate human monoclonal antibodies for therapeutics", Curr Opin Biotechnol. 13:593-97 (2002).
Kirkland, et al., "Analysis of the fine specificity and cross-reactivity of monoclonal anti-lipid A antibodies", J. Immunol. 137(11): 3614-3619 (1986).
Korndorfer et al., "Crystallographic analysis of an "anticalin" with tailored specificity for fluorescein reveals high structural plasticity of the lipocalin loop region", Proteins: Structure, Function, and Bioinformatics, 53(1):121-129 (2003).
Kuderova et al., "Characterization of four nucleic acid-binding single-chain Fv fragments by direct and competitive solid-phase radioimmunoassays", J Biol Chem, 269(52): 32957-32962 (1994).
Kuttner et al., "Linker peptide and affinity tag for detection and purification of single-chain FV fragments," BioTechniques, 36: 864-870 (2004).
Landegren et al., "Mechanism of T lymphocyte activation by OKT3 antibodies. A general model for T cell induction", Eur. J. Immunol. 14(4): 325-28 (1984).
Larrick et al., "Polymerase chain reaction using mixed primers: cloning of human monoclonal antibody variable region genes from single hybridoma cells", Bio/Technology 7:934 (1989).

(Continued)

*Primary Examiner* — Phuong Huynh

(57) ABSTRACT

Isolated antigen binding molecules that specifically binds to a molecule comprising an amino acid sequence selected from the group consisting of GGGS (SEQ ID NO: 1), GGGGS (SEQ ID NO: 46) and related sequences are provided. The antigen binding molecules may be used in the methods provided herein.

5 Claims, 10 Drawing Sheets

Specification includes a Sequence Listing.

(56) References Cited

OTHER PUBLICATIONS

Liu et al., "Chimeric mouse-human IgG1 antibody that can mediate lysis of cancer cells", Proc. Nat. Acad. Sci. USA 84:3439 (1987).
Lloyd et al. Protein Engineering, Design & Selection 22:159-168 (Year: 2009).
Lonberg et al., "Antigen-specific human antibodies from mice comprising four distinct genetic modifications", Nature 368: 856-59 (1994).
Lonberg, The pharmacology of monoclonal antibodies, Handbook of Experimental Pharmacology 113: 49-101 (1994).
MacCallum et al., "Antibody-antigen interactions: contact analysis and binding site topography", J. Mol. Biol., 262(5):732-745 (1996).
McPherson, A. "Crystallization of Proteins from Polyethylene Glycol", J Biol Chem, 251(20): 6300-6303 (1976).
McPherson, A. "Current approaches to macromolecular crystallization", Eur J Biochem, 189: 1-23 (1990).
Mendez et al., "Functional transplant of megabase human immunoglobulin loci recapitulates human antibody response in mice", Nat. Genet. 15:146-56 (1997).
Mohammad! et al., "Insilico analysis of three different tag polypeptides with dual roles in scFv antibodies", Journal of Theoretical Biology, 402:100-106 (2016).
Moldenhauer, et al., "Identity of HML-1 antigen on intestinal intraepithelial T cells and of B-ly7 antigen on hairy cell leukaemia", Scand. J. Immunol., 32(2): 77-82 (1990).
Morel et al., "Monoclonal antibodies to bovine serum albumin: affinity and specificity determinations", Molec. Immunol., 25(1): 7-15 (1988).
Neuberger, "Generating high-avidity human Mabs in mice", Nature Biotech 14:826 (1996).
Nicholson et al., "Construction and characterisation of a functional CD19 specific single chain Fv fragment for Immunotherapy of B lineage leukaemia and lymphoma", Mol. Immunol. 34:(16-17) 1157-65 (1997).
Padlan et al., "Identification of specificity-determining residues in antibodies", FASEB J. 9:133-39 (1995).
Perisic et al., "Crystal structure of a diabody, a bivalent antibody fragment" Structure 2(12): 1217-26 (1994).
Poljak et al., "Production and structure of diabodies", Structure 2: 1121-23 (1994).
Riechmann et al., "Reshaping human antibodies for therapy", Nature 332:323 (1988).
Roque et al., "Antibodies and genetically engineered related molecules: production and purification", Biotechnol. Prog. 20:639-654 (2004).
Roversi, P. et al., "Modelling prior distributions of atoms for macromolecular refinement and completion", Acta Crystallogr D Biol Crystallogr, 56(Pt 10): 1316-1323 (2000).
Rudikoff et al., Proc Natl Acad Sci USA vol. 79 p. 1979-1983 (Year: 1982).
Russell et al., "Production of Protective Human Antipneumococcal Antibodies by Transgenic Mice with Human Immunoglobulin Loci", Infect Immun. 68:1820-26 (2000).
Sastry et al., "Cloning of the immunological repertoire in *Escherichia coli* for generation of monoclonal catalytic antibodies: construction of a heavy chain variable region-specific cDNA library", Proc. Natl. Acad. Sci. USA 86:5728-32 (1989).
Schlebusch et al., "Production of a single chain fragment (scFv) of the murine anti-idiotypic antibody ACA125 as phage-displayed and soluble antibody by recombinant phage antibody technique", Hybridoma 16:47-52 (1997).
Seet et al., "Generation of mature T cells from human hematopoietic stem/progenitor cells in artificial thymic organoids", Nature Methods 14(5):521 (2017).
Smallshaw et al., "Synthesis, cloning and expression of the single-chain Fv gene of the HPr-specific monoclonal antibody, Jel42. Determination of binding constants with wild-type and mutant HPrs" Protein Engineering 12(7):623-630 (1999).

Stahli et al., "Distinction of epitopes by monoclonal antibodies", Methods in Enzymology, 92: 242-253 (1983).
Stauber, "Development and Applications of Enhanced Green Fluorescent Protein Mutants", Biotechniques 24:462-471 (1998).
Stocks, "Intrabodies: production and promise", Drug Discovery Today 9(22):960-66 (2004).
Tamura et al., "Structural correlates of an anticarcinoma antibody: identification of specificity-determining residues (SDRs) and development of a minimally immunogenic antibody variant by retention of SDRs only", J. Immunol. 164:1432-41 (2000).
Taylor et al., "A transgenic mouse that expresses a diversity of human sequence heavy and light chain immunoglobulins", Nucleic Acids Research 20:6287-95 (1992).
Taylor et al., "Human immunoglobulin transgenes undergo rearrangement, somatic mutation and class switching in mice that lack endogenous IgM", Intl Immunol 6:579-91 (1994).
Terpe, "Overview of tag protein fusions: from molecular and biochemical fundamentals to commercial systems", Appl Microbiol Biotechnol, 60: 523-533 (2003).
Tomizuka et al., "Double trans-chromosomic mice: Maintenance of two individual human chromosome fragments containing Ig heavy and K loci and expression of fully human antibodies", Proc Nat Acad Sci USA 97:722-27 (2000).
Tomizuka et al., "Functional expression and germline atransmission of a human chromosome fragment in chimaeric mice" Nature Genetics 16:133-43 (1997).
Tramontano, A. et al., "Framework residue 71 is a major determinant of the position and conformation of the second hypervariable region in the VH domains of immunoglobulins", J Mol Biol, 215(1): 175-82 (1990).
Tsuda et al., "Inactivation of the MouseHPRTLocus by a 203-bp Retroposon Insertion and a 55-kb Gene-Targeted Deletion: Establishment of New HPRT-Deficient Mouse Embryonic Stem Cell Lines", Genomics, 42:413-21 (1997).
Tuaillon et al., "Biased utilization of DHQ52 and JH4 gene segments in a human Ig transgenic minilocus is independent of antigenic selection", J Immunol 152:2912-20 (1994).
Tuaillon et al., "Human immunoglobulin heavy-chain minilocus recombination in transgenic mice: gene-segment use in mu and gamma transcripts", Proc Nat Acad Sci USA 90:3720-24 (1993).
Veber and Freidinger, "The design of metabolically-stable peptide analogs", TINS, p. 392 (1985).
Winter et al., "Antibody-based therapy, humanized antibodies", TIPS 14:139 (1993).
Winter et al., "Making antibodies by phage display technology", Ann. Rev. Immunol. 12:433-55 (1994).
Zhang et al., "Humanization of an anti-human TNF-alpha antibody by variable region resurfacing with the aid of molecular modeling", Mol. Immunol. 42(12):1445-1451 (2005).
Al-Lazikani, 8. et al., "Standard conformations for the canonical structures of immunoglobulins", Journal of Molecular Biology, 273(4): 927-948 (1997).
Alting Mees et al., "Monoclonal Antibody Expression Libraries: A Rapid Alternative to Hybridomas", Strategies in Molecular Biology, 3:1-9 (1990).
Arbones et al., "Lymphocyte homing and leukocyte rolling and migration are impaired in L-selectin-deficient mice", Immunity, 1:247-60 (1994).
Baines and Thorpe, "Purification of Immunoglobulin G (IgG)", Methods in Molecular Biology, 10:79-104 (1992).
Bird et al., "Single-chain antigen-binding proteins", Science, 242:423-26 (1988).
Bricogne, G. "[23] Bayesian statistical viewpoint on structure determination: Basic concepts and examples", Meth Enzymol, 276A: 361-423 (1997).
Bricogne, G. "Direct phase determination by entropy maximization and likelihood ranking: status report and perspectives", Acta Crystallogr D Biol Crystallogr 49(Pt 1): 37-60 (1993).
Bruggemann et al., "Production of human antibody repertoires in transgenic mice", Curr. Opin. Biotechnol. 8:455-58 (1997).
Burton et al., "Human antibodies from combinatorial libraries", Adv. Immunol 57:191-280 (1994).

(56) References Cited

OTHER PUBLICATIONS

Campbell et al (in Monoclonal Antibody Technology, Elsevier Science Publisher, New York, NY, p. 1-32 (Year: 1984).
Carrillo et al., "The multiple sequence alignment problem in biology", J. Applied Math. 48:1073 (1988).
Chalfie et al., "Green Fluorescent Protein as a Marker for Gene Expression", Science, 263:802-805 (1994).
Champe, M. et al., "Monoclonal Antibodies That Block the Activity of Leukocyte Function-associated Antigen 1 Recognize Three Discrete Epitopes in the Inserted Domain of CD11a", J Biol Chem, 270(3): 1388-94 (1995).
Chayen, "The role of oil in macromolecular crystallization", Structure 5: 1269-1274 (1997).
Chen et al., "Immunoglobulin gene rearrangement in 8-cell deficient mice generated by targeted deletion of the JH locus", Intl Immunol 5:647-656 (1993).
Cheung et al., "Epitope-specific antibody response to the surface antigen of duck hepatitis B virus in infected ducks", Virology, 176(2): 546-552 (1990).
Choi et al., "Transgenic mice containing a human heavy chain immunoglobulin gene fragment cloned in a yeast artificial chromosome", Nature Genetics 4:117-23 (1993).
Chothia, C. et al., "Canonical structures for the hypervariable regions of immunoglobulins", J Mol Biol, 196: 901-917 (1987).
Chothia, C. et al., "Conformations of immunoglobulin hypervariable regions", Nature, 342: 877-883 (1989).
Chothia, C. et al., "Structural repertoire of the human VH segments" J Mol Biol, 227: 799-817 (1992).
Clark, "Antibody humanization: a case of the 'Emperor's new clothes'?", Immunology Today, 21(8):397-402 (2000).
Cunningham et al., "High-resolution epitope mapping of hGH-receptor interactions by alanine-scanning mutagenesis", Science 244(4908): 1081-85 (1989).
Dall'Acqua et al., "Antibody humanization by framework shuffling", Methods, 36(1):43-60 (2005).
Davies et al., "Affinity improvement of single body VH domains: residues in all three hypervariable regions affect antigen binding", Immunotechnology 2:169-179 (1996).
Davis et al., "Production of human antibodies from transgenic mice", Antibody Engineering: Methods and Protocols, (Lo, ed) Humana Press, NJ, 191-200 (2003).
Davis et al., "Transgenic mice as a source of fully human antibodies for the treatment of cancer", Cancer Metastasis Rev. 18:421-25 (1999).
Dayhoff et al., "Atlas of Protein Sequence and Structure: A Model of Evolutionary Change in Proteins", 5: 345-352 (1978).
Edwards et al., J Mol Biol. 334(1): 103-118 (Year: 2003).
Evans et al., "Design of Nonpeptidal Ligands for a Peptide Receptor: Cholecystokinin Antagonists", J. Med. Chem, 30:1229-39 (1987).
Fauchere, "Elements for the Rational Design of Peptide Drugs", Adv. Drug Res. (Testa, ed.) 15:29-69 (1986).
Fishwild et al., "High-avidity human IgGk monoclonal antibodies from a novel strain of minilocus transgenic mice", Nature Biotechnology, 14:845-51 (1996).
Gallo et al., The human immunoglobulin loci introduced into mice: V (D) and J gene segment usage similar to that of adult humans, Eur J. Immun. 30:534-40 (2000).
Giege, R. et al., "Crystallogenesis of biological macromolecules: facts and perspectives", Acta Crystallogr D Biol Crystallogr, 50(Pt 4): 339-350 (1994).
Green et al., "Antigen-specific human monoclonal antibodies from mice engineered with human Ig heavy and light chain YACs", Nat. Genet. 7:13-21 (1994).
Green et al., "Regulation of B Cell Development by Variable Gene Complexity in Mice Reconstituted with Human Immunoglobulin Yeast Artificial Chromosomes", J Exp Med. 188:483-95 (1998).
Green, "Antibody engineering via genetic engineering of the mouse: XenoMouse strains are a vehicle for the facile generation of therapeutic human monoclonal antibodies", J Immunol Methods 231:11-23 (1999).
Harlow and Lane, "Antibodies, A Laboratory Manual", Cold Spring Harbor Press (1988).
Harris, "Processing of C-terminal lysine and arginine residues of proteins isolated from mammalian cell culture", J Chromatog, 705:129-34 (1995).
Hauser, et al. "kClust: fast and sensitive clustering of large protein sequence databases", BMC Bioinformatics, 248 (2013).
Heim et al., "Engineering green fluorescent protein for improved brightness, longer wavelengths and fluorescence resonance energy transfer", Curr. Biol. 6: 178-182 (1996).
Henikoff et al., "Amino acid substitution matrices from protein blocks", Proc. Natl. Acad. Sci. U.S.A., 89(22):10915-10919 (1992).
Holliger et al., "Diabodies: Small bivalent and bispecific antibody fragments", Proc Natl Acad Sci U.S.A. 90:6444-48, (1993).
Holt et al., "Domain antibodies: proteins for therapy", Trends in Biotechnology 21(11): 484-490 (2003).
Honegger and Pluckthun, "Yet another numbering scheme for immunoglobulin variable domains: an automatic modeling and analysis tool", J Mol Biol 309:657-670 (2001).
Hoogenboom et al., "By-passing immunisation. Human antibodies from synthetic repertoires of germline VH gene segments rearranged in vitro", J. Mol. Biol. 227:381-388 (1992).
Huse et al., "Generation of a large combinatorial library of the immunoglobulin repertoire in phage lambda", Science 246:1275-81 (1989).
Huston et al., "Protein engineering of antibody binding sites: Recovery of specific activity in an anti-digoxin single-chain Fv analogue produced in *Escherichia coli*", Proc. Natl. Acad. Sci. U.S.A. 85:5879-83 (1988).
Hwang et al., "Use of human germline genes in a CDR homology-based approach to antibody humanization" Methods 36(1):35-42 (2005).
Ichiki et al., "Regulation of the expression of human C e germline transcript", J. Immunol. 150:5408-5417 (1993).
Ito et al., FEBS Letters 309(1): 85-88 (Year: 1992).
Anonymous (2006) "Anti-Myc tag antibody ab9106" abcam catalog <Retrieved from the Internet: URL: https://www.abcam.com/products/primary-antibodies/myc-tag-antibody-ab9106.pdf>.
Anonymous (2011) "Pierce Anti-GST Coated Plates" Thermo Scientific catalog <Retrieved from the Internet: URL: https://www.thermofisher.com/documentconnect/document-connect.html?url= https://assets.thermofisher.com/TFS-Assets%2FLSG%2Fmanuals% 2FMAN0011662 Pierce AntiGST CoatPlate_UG.pdf>.
Brinkmann, U. et al. (1997) "Cloning and expression of the recombinant FAb fragment of monoclonal antibody K1 that reacts with mesothelin present on mesotheliomas and ovarian cancers" Int. J. Cancer 71:638-644.
Burrin, J. et al. (1991) "Production and assessment of antibodies" Principles and Practice of Immunoassay:19-52.
Hilpert, K. et al. (2001) "Anti-c-myc antibody 9E10: epitope key positions and variability characterized using peptide spot synthesis on cellulose" Protein Engineering 14(10):803-806.
Lerner, R.A. et al. (1981) "Chemically synthesized peptides predicted from the nucleotide sequence of the hepatitis B virus genome elicit antibodies reactive with he native envelope protein of Dane particles" Proc. Natl. Acad. Scie. USA 78(6):3403-3407.
Niman, H.L. et al. (1983) "Generation of protein-reactive antibodies by short peptides is an event of high frequency: Implications for the structural basis of immune recognition" Proc. Natl. Acad. Scie. USA 80(16):4949-4953.
Sakarellos-Daitsiotis, M. et al. (2006) "Artificial Carriers: A Strategy for Constructing Antigenic/Immunogenic Conjugates" Current Topics in Medicinal Chemistry 6(16):1715-1735.
Walter, G. (1986) "Production and use of antibodies against synthetic peptides" Journal of Immunological Methods 88(2):149-161.
Office Action dated Mar. 27, 2023 for European Appl. No. 18783304. 1.
International Search Report—Written Opinion dated Nov. 27, 2018 for PCT/US2018/052205.

\* cited by examiner

| Clone | CDR1 | CDR2 | CDR3 |
|---|---|---|---|
| 132_VL | QASQSVYNNNRLS<br>SEQ ID NO: 8 | LASTLAS<br>SEQ ID NO: 9 | AGYQYSETDGFA<br>SEQ ID NO: 10 |
| 154_VL | QASQSIGSHLA<br>SEQ ID NO: 11 | GASTLAS<br>SEQ ID NO: 12 | QCTYAGGYYVFA<br>SEQ ID NO: 13 |
| 163_VL | QASEDITNSLA<br>SEQ ID NO: 14 | RASTLAS<br>SEQ ID NO: 15 | QQGYSSTNVDNI<br>SEQ ID NO: 16 |
| 132_VH | SSYYMC<br>SEQ ID NO: 17 | CIDDGGSYTYYASWAK<br>SEQ ID NO: 18 | HVRGADYYNL<br>SEQ ID NO: 19 |
| 154_VH | SSAYMC<br>SEQ ID NO: 20 | CIYGSNSGNTYYANWAK<br>SEQ ID NO: 21 | YAVGSWDYFDL<br>SEQ ID NO: 22 |
| 163_VH | KKYYMC<br>SEQ ID NO: 23 | CVDTGDAFIGYANWAK<br>SEQ ID NO: 24 | GVYPINTGYYYFDL<br>SEQ ID NO: 25 |

Fig. 1A

| Clone | CDR1 | CDR2 | CDR3 |
|---|---|---|---|
| 132_VL | QASQSVYNNNRLS<br>SEQ ID NO: 8 | LASTLAS<br>SEQ ID NO: 9 | AGYQYSETDGFA<br>SEQ ID NO: 10 |
| 154_VL | QASQSIGSHLA<br>SEQ ID NO: 11 | GASTLAS<br>SEQ ID NO: 12 | QCTYAGGYYVFA<br>SEQ ID NO: 13 |
| 163_VL | QASEDITNSLA<br>SEQ ID NO: 14 | RASTLAS<br>SEQ ID NO: 15 | QQGYSSTNVDNI<br>SEQ ID NO: 16 |
| 132_VH | GFSFSSSY<br>SEQ ID NO: 26 | DDGGS<br>SEQ ID NO: 27 | HVRGADYYNL<br>SEQ ID NO: 19 |
| 154_VH | GFSFSSSA<br>SEQ ID NO: 28 | YGSNSG<br>SEQ ID NO: 29 | YAVGSWDYFDL<br>SEQ ID NO: 22 |
| 163_VH | KFSFNKKY<br>SEQ ID NO: 30 | DTGDA<br>SEQ ID NO: 31 | GVYPINTGYYYFDL<br>SEQ ID NO: 25 |

Fig. 1B

| Clone | CDR1 | CDR2 | CDR3 |
|---|---|---|---|
| 132_VL | QSVYNNNR SEQ ID NO: 32 | LASTLAS SEQ ID NO: 9 | AGYQYSETDGFA SEQ ID NO: 10 |
| 154_VL | QSIGSH SEQ ID NO: 33 | GASTLAS SEQ ID NO: 12 | QCTYAGGYYVFA SEQ ID NO: 13 |
| 163_VL | EDITNS SEQ ID NO: 34 | RASTLAS SEQ ID NO: 15 | QQGYSSTNVDNI SEQ ID NO: 16 |
| 132_VH | GFSFSSSYY SEQ ID NO: 35 | IDDGGSY SEQ ID NO: 36 | TRHVRGADYYNL SEQ ID NO: 37 |
| 154_VH | GFSFSSSAY SEQ ID NO: 38 | IYGSNSGN SEQ ID NO: 39 | ARYAVGSWDYFDL SEQ ID NO: 40 |
| 163_VH | KFSFNKKYY SEQ ID NO: 41 | VDTGDAF SEQ ID NO: 42 | ARGVYPINTGYYYFDL SEQ ID NO: 43 |

Fig. 1C

| | |
|---|---|
| 132_VH | METGLRWLLLVAVLKGVQCQEQLEESGGDLVQPEGSLTLTCT ASGFSFSSSYYMCWVRQAPGKGLEWIACIDDGGSYTYYASWA KGRFTISKTSSTTVTLQMTSLTDADTATYFCTRHVRGADYYNL WGPGTLVTVSS (SEQ ID NO: 2) |
| 132_VH | MDTRAPTQLLGLLLLWLPGATFAIVMTQTPSSVSAAVGGTVTI SCQASQSVYNNNRLSWYQQKPGQPPKLLIYLASTLASGVPSRF KGSGSGTQFTLTISDLECDDAATYYCAGYQYSETDGFAFGGGT EVVVK (SEQ ID NO: 3) |
| 154_VH | METGLRWLLLVAVLKGVQCQSLEESGGDLVKPEGSLTLTCTA SGFSFSSSAYMCWVRQAPGKGLEWIACIYGSNSGNTYYANWA KGRFTISKTSSTTVTLQMTSLTAADTATYFCARYAVGSWDYF DLWGPGTLVTASS (SEQ ID NO: 4) |
| 154_VL | MDTRAPTQLLGLLLLWLPGARCDFVMTQTPASVSEPVGGTVT IKCQASQSIGSHLAWYQQKPGQPPKLLIYGASTLASGVPSRFK GSGSGTQFTLTISDLECADAATYYCQCTYAGGYYVFAFGGGT EVVVK (SEQ ID NO: 5) |
| 163_VH | METGLRWLLLVAVLKGVQCQQQLEESGGDLVKPEGSLTLTCT ASKFSFNKKYYMCWVRQAPGKGLEWIGCVDTGDAFIGYANW AKGRFTVSKTSSTTVDLKMTSLTAADTATYFCARGVYPINTGY YYFDLWGPGTLVTVSS (SEQ ID NO: 6) |
| 163_VL | MDTRAPTQLLGLLLLWLPGARCALVMTQTPASVEAAVGGTV TIKCQASEDITNSLAWYQQKPGQPPNLLIYRASTLASGVSSRFK GSRSGTEFTLTISGVECADAATYYCQQGYSSTNVDNIFGGGTE VVVK (SEQ ID NO: 7) |

Fig. 2

SEQUENCE LISTING

<160> NUMBER OF SEQ ID NOS: 62

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Gly Gly Ser
1

<210> SEQ ID NO 2
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Gln
            20                  25                  30

Pro Glu Gly Ser Leu Thr Leu Thr Cys Thr Ala Ser Gly Phe Ser Phe
        35                  40                  45

Ser Ser Ser Tyr Tyr Met Cys Trp Val Arg Gln Ala Pro Gly Lys Gly
    50                  55                  60

Leu Glu Trp Ile Ala Cys Ile Asp Asp Gly Gly Ser Tyr Thr Tyr Tyr
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Asp Ala Asp Thr Ala Thr
            100                 105                 110

Tyr Phe Cys Thr Arg His Val Arg Gly Ala Asp Tyr Tyr Asn Leu Trp
        115                 120                 125

Gly Pro Gly Thr Leu Val Thr Val Ser Ser
    130                 135

```
<210> SEQ ID NO 3
<211> LENGTH: 134
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3
```

Met Asp Thr Arg Ala Pro Thr Gln Leu Leu Gly Leu Leu Leu Leu Trp
1               5                   10                  15

Leu Pro Gly Ala Thr Phe Ala Ile Val Met Thr Gln Thr Pro Ser Ser
            20                  25                  30

Val Ser Ala Ala Val Gly Gly Thr Val Thr Ile Ser Cys Gln Ala Ser
        35                  40                  45

Gln Ser Val Tyr Asn Asn Arg Leu Ser Trp Tyr Gln Gln Lys Pro
    50                  55                  60

Gly Gln Pro Pro Lys Leu Leu Ile Tyr Leu Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Ala Gly Tyr Gln Tyr Ser Glu Thr Asp Gly Phe Ala Phe Gly Gly Gly
        115                 120                 125

Thr Glu Val Val Val Lys
        130

```
<210> SEQ ID NO 4
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Glu Gly Ser Leu Thr Leu Thr Cys Thr Ala Ser Gly Phe Ser Phe Ser
        35                  40                  45

Ser Ser Ala Tyr Met Cys Trp Val Arg Gln Ala Pro Gly Lys Gly Leu
    50                  55                  60

Glu Trp Ile Ala Cys Ile Tyr Gly Ser Asn Ser Gly Asn Thr Tyr Tyr
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Tyr Ala Val Gly Ser Trp Asp Tyr Phe Asp Leu
        115                 120                 125

Trp Gly Pro Gly Thr Leu Val Thr Ala Ser Ser
        130                 135

```
<210> SEQ ID NO 5
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Asp Thr Arg Ala Pro Thr Gln Leu Leu Gly Leu Leu Leu Leu Trp
1               5                   10                  15

Leu Pro Gly Ala Arg Cys Asp Phe Val Met Thr Gln Thr Pro Ala Ser
            20                  25                  30

Val Ser Glu Pro Val Gly Gly Thr Val Thr Ile Lys Cys Gln Ala Ser
        35                  40                  45

Gln Ser Ile Gly Ser His Leu Ala Trp Tyr Gln Gln Lys Pro Gly Gln
    50                  55                  60

Pro Pro Lys Leu Leu Ile Tyr Gly Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Cys
            100                 105                 110

Thr Tyr Ala Gly Gly Tyr Tyr Val Phe Ala Phe Gly Gly Gly Thr Glu
        115                 120                 125

Val Val Val Lys
    130

<210> SEQ ID NO 6
<211> LENGTH: 142
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Asp Leu Val Lys
            20                  25                  30

Pro Glu Gly Ser Leu Thr Leu Thr Cys Thr Ala Ser Lys Phe Ser Phe
        35                  40                  45

Asn Lys Lys Tyr Tyr Met Cys Trp Val Arg Gln Ala Pro Gly Lys Gly
    50                  55                  60

Leu Glu Trp Ile Gly Cys Val Asp Thr Gly Asp Ala Phe Ile Gly Tyr
65                  70                  75                  80

Ala Asn Trp Ala Lys Gly Arg Phe Thr Val Ser Lys Thr Ser Ser Thr
                85                  90                  95

Thr Val Asp Leu Lys Met Thr Ser Leu Thr Ala Ala Asp Thr Ala Thr
            100                 105                 110

Tyr Phe Cys Ala Arg Gly Val Tyr Pro Ile Asn Thr Gly Tyr Tyr Tyr
        115                 120                 125

Phe Asp Leu Trp Gly Pro Gly Thr Leu Val Thr Val Ser Ser
    130                 135                 140
```

```
<210> SEQ ID NO 7
<211> LENGTH: 132
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ala Ser
            20                  25                  30

Val Glu Ala Ala Val Gly Gly Thr Val Thr Ile Lys Cys Gln Ala Ser
        35                  40                  45

Glu Asp Ile Thr Asn Ser Leu Ala Trp Tyr Gln Lys Pro Gly Gln
    50                  55                  60

Pro Pro Asn Leu Leu Ile Tyr Arg Ala Ser Thr Leu Ala Ser Gly Val
65                  70                  75                  80

Ser Ser Arg Phe Lys Gly Ser Arg Ser Gly Thr Glu Phe Thr Leu Thr
                85                  90                  95

Ile Ser Gly Val Glu Cys Ala Asp Ala Ala Thr Tyr Tyr Cys Gln Gln
            100                 105                 110

Gly Tyr Ser Ser Thr Asn Val Asp Asn Ile Phe Gly Gly Gly Thr Glu
        115                 120                 125

Val Val Val Lys
    130

<210> SEQ ID NO 8
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Ala Ser Gln Ser Val Tyr Asn Asn Asn Arg Leu Ser
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Leu Ala Ser Thr Leu Ala Ser
1               5

<210> SEQ ID NO 10
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 10

Ala Gly Tyr Gln Tyr Ser Glu Thr Asp Gly Phe Ala
1               5                   10

<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gln Ala Ser Gln Ser Ile Gly Ser His Leu Ala
1               5                   10

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Ala Ser Thr Leu Ala Ser
1               5

<210> SEQ ID NO 13
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gln Cys Thr Tyr Ala Gly Gly Tyr Tyr Val Phe Ala
1               5                   10

<210> SEQ ID NO 14
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Gln Ala Ser Glu Asp Ile Thr Asn Ser Leu Ala
1               5                   10

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 15

Arg Ala Ser Thr Leu Ala Ser
1               5

<210> SEQ ID NO 16
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gln Gln Gly Tyr Ser Ser Thr Asn Val Asp Asn Ile
1               5                   10

<210> SEQ ID NO 17
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Ser Tyr Tyr Met Cys
1               5

<210> SEQ ID NO 18
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Cys Ile Asp Asp Gly Gly Ser Tyr Thr Tyr Tyr Ala Ser Trp Ala Lys
1               5                   10                  15

<210> SEQ ID NO 19
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

His Val Arg Gly Ala Asp Tyr Tyr Asn Leu
1               5                   10

<210> SEQ ID NO 20
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Ser Ala Tyr Met Cys
1               5
```

```
<210> SEQ ID NO 21
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Cys Ile Tyr Gly Ser Asn Ser Gly Asn Thr Tyr Tyr Ala Asn Trp Ala
1               5                   10                  15
Lys

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Tyr Ala Val Gly Ser Trp Asp Tyr Phe Asp Leu
1               5                   10

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Lys Lys Tyr Tyr Met Cys
1               5

<210> SEQ ID NO 24
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Cys Val Asp Thr Gly Asp Ala Phe Ile Gly Tyr Ala Asn Trp Ala Lys
1               5                   10                  15

<210> SEQ ID NO 25
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Val Tyr Pro Ile Asn Thr Gly Tyr Tyr Tyr Phe Asp Leu
1               5                   10
```

```
<210> SEQ ID NO 26
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Gly Phe Ser Phe Ser Ser Ser Tyr
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Asp Gly Gly Ser
1               5

<210> SEQ ID NO 28
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Phe Ser Phe Ser Ser Ser Ala
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Tyr Gly Ser Asn Ser Gly
1               5

<210> SEQ ID NO 30
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Lys Phe Ser Phe Asn Lys Lys Tyr
1               5

<210> SEQ ID NO 31
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 31

Asp Thr Gly Asp Ala
1               5

<210> SEQ ID NO 32
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Ser Val Tyr Asn Asn Asn Arg
1               5

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Gln Ser Ile Gly Ser His
1               5

<210> SEQ ID NO 34
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Glu Asp Ile Thr Asn Ser
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Phe Ser Phe Ser Ser Ser Tyr Tyr
1               5

<210> SEQ ID NO 36
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 36

Ile Asp Asp Gly Gly Ser Tyr
1               5

<210> SEQ ID NO 37
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Thr Arg His Val Arg Gly Ala Asp Tyr Tyr Asn Leu
1               5                   10

<210> SEQ ID NO 38
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Phe Ser Phe Ser Ser Ser Ala Tyr
1               5

<210> SEQ ID NO 39
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Ile Tyr Gly Ser Asn Ser Gly Asn
1               5

<210> SEQ ID NO 40
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ala Arg Tyr Ala Val Gly Ser Trp Asp Tyr Phe Asp Leu
1               5                   10

<210> SEQ ID NO 41
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Lys Phe Ser Phe Asn Lys Lys Tyr Tyr
1               5

```
<210> SEQ ID NO 42
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Val Asp Thr Gly Asp Ala Phe
1               5

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Arg Gly Val Tyr Pro Ile Asn Thr Gly Tyr Tyr Tyr Phe Asp Leu
1               5                   10                  15

<210> SEQ ID NO 44
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Ser Thr Ser Gly Ser Gly Lys Pro Gly Ser Gly Glu Gly Ser Thr
1               5                   10                  15

Lys Gly

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Gly Gly Gly Ser Gly Gly Gly Gly Ser Gly Gly Gly Gly Ser
1               5                   10                  15

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Gly Gly Gly Ser
1               5
```

```
<210> SEQ ID NO 47
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Gly Gly Ser Gly Lys Pro Gly Ser Gly Glu Gly Gly Gly Ser
1               5                   10                  15

<210> SEQ ID NO 48
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Gly Gly Ser Gly Lys Pro Gly Ser Gly Glu Gly Gly Gly Gly Ser
1               5                   10                  15

<210> SEQ ID NO 49
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Gly Gly Gly Ser Gly Lys Pro Gly Ser Gly Gly Gly Gly Ser
1               5                   10                  15

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Gly Gly Gly Ser Gly Lys Pro Gly Ser Gly Glu Gly Gly Ser
1               5                   10                  15

<210> SEQ ID NO 51
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gly Gly Gly Gly Ser Gly Lys Pro Gly Ser Gly Glu Gly Gly Gly Ser
1               5                   10                  15

<210> SEQ ID NO 52
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 52

Gly Gly Gly Gly Ser Gly Lys Pro Gly Ser Gly Glu Gly Gly Gly Gly
1               5                   10                  15

Ser

<210> SEQ ID NO 53
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Gly Gly Gly Ser Gly Gly Gly Ser Gly Gly Gly Gly Ser Gly
1               5                   10                  15

<210> SEQ ID NO 54
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Gly Gly Gly Gly Gly Ser Gly Gly Gly Ser Gly Gly Gly Gly Ser
1               5                   10                  15

<210> SEQ ID NO 55
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Gly Gly Gly Gly Ser Gly Gly Gly Gly Ser Gly Gly Gly Gly Ser
1               5                   10                  15

<210> SEQ ID NO 56
<211> LENGTH: 414
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56
atggagactg ggctgcgctg gcttctcctg gtcgctgtgc tcaaaggtgt ccagtgtcag     60
gagcagctgg aggagtccgg gggagacctg gtccagcctg agggatccct gacactcacc    120
tgcacagctt ctggattctc cttcagtagc agctactaca tgtgctgggt ccgccaggct    180
ccagggaagg ggctggagtg gatcgcgtgc attgatgatg gtggtagtta tacttactac    240
gcgagctggg cgaaaggccg attcaccatc tccaaaacct cgtcgaccac ggtgactctg    300
```

| | |
|---|---|
| caaatgacca gtctgacaga cgcggacacg gccacttatt tctgtacgag acatgttagg | 360 |
| ggtgctgatt attataattt gtggggccca ggcaccctgg tcaccgtctc ctca | 414 |

<210> SEQ ID NO 57
<211> LENGTH: 402
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

| | |
|---|---|
| atggacacga gggcccccac tcagctgctg gggctcctgc tgctctggct cccaggtgcc | 60 |
| acatttgcca tcgtgatgac ccagactcca tcctccgtgt ctgcagctgt ggaggcaca | 120 |
| gtcaccatca gttgccaggc cagtcagagt gtttataata caaccgctt atcctggtat | 180 |
| cagcagaaac cagggcagcc tcccaagctc ctgatctatc tggcatccac tctggcatct | 240 |
| ggggtcccat cgcggttcaa aggcagtgga tctgggacac agttcactct caccatcagc | 300 |
| gacctggagt gtgacgatgc tgccacttat tattgtgcag gatatcaata tagtgagact | 360 |
| gatggttttg ctttcggcgg agggaccgag gtggtggtca aa | 402 |

<210> SEQ ID NO 58
<211> LENGTH: 417
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 58

| | |
|---|---|
| atggagactg gctgcgctg gcttctcctg gtcgctgtgc tcaaaggtgt ccagtgtcag | 60 |
| tcgttggagg agtccggggg agacctggtc aagcctgagg gatccctgac actcacctgc | 120 |
| acagcctctg gattctcctt cagtagcagc gcctacatgt gctgggtccg ccaggctcca | 180 |
| gggaagggc tggagtggat cgcatgcatt tatggtagta atagtggtaa cacttactac | 240 |
| gcgaactggg cgaaaggccg attcaccatc tccaaaacct cgtcgaccac ggtgactctg | 300 |
| cagatgacca gtctgacagc cgcggacacg gccacctatt tctgtgcgag atatgctgtc | 360 |
| ggtagttggg actattttga cttgtggggc ccaggcaccc tggtcaccgc ctcctca | 417 |

<210> SEQ ID NO 59
<211> LENGTH: 396
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 59

| | |
|---|---|
| atggacacga gggcccccac tcagctgctg gggctcctgc tgctctggct cccaggtgcc | 60 |
| agatgtgatg ttgtgatgac ccagactcca gcctccgtgt ctgaacctgt ggaggcaca | 120 |
| gtcaccatca agtgccaggc cagtcagagc attggtagtc atttagcctg gtatcagcag | 180 |
| aaaccagggc agcctcccaa gctcctgata tatggtgcat ccactctggc atctggggtc | 240 |
| ccatcgcggt tcaaaggcag tggatctggg acacagttca ctctcaccat cagcgacctg | 300 |

```
gagtgtgccg atgctgccac ttactactgt caatgtactt atgctggtgg ttattatgtt    360
tttgccttcg gcggagggac cgaggtggtg gtcaag                              396
```

<210> SEQ ID NO 60
<211> LENGTH: 426
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 60

```
atggagactg gctgcgctg gcttctcctg gtcgctgtgc tcaaaggtgt ccagtgtcag      60
cagcagctgg aggagtccgg gggagacctg gtcaagcctg agggatccct gacactcacc    120
tgcacagctt ctaaattctc cttcaataag aagtattaca tgtgctgggt ccgccaggct    180
ccagggaagg ggctggagtg gatcggatgt gttgatactg gtgatgcttt catcggctac    240
gcgaactggg cgaaaggccg attcaccgtc tccaaaacct cgtcgaccac ggtggatctg    300
aaaatgacca gtctgacagc cgcggacacg gccacctatt tctgtgcgag aggggtttat    360
cctattaata ctggttatta ctactttgac ttgtggggcc aggcaccct ggtcaccgtc     420 tcctca                                                               426
```

<210> SEQ ID NO 61
<211> LENGTH: 396
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 61

```
atggacacga gggcccccac tcagctgctg ggctcctgc tgctctggct cccaggtgcc      60
agatgtgccc ttgtgatgac ccagactcca gcctccgtgg aggcagctgt gggaggcaca    120
gtcaccatca gtgccaggc cagtgaggat attactaatt ctttagcctg gtatcagcag    180
aaaccagggc agcctcccaa cctcctgatc tacagggcat ccactctggc atctggggtc    240
tcatcgcggt tcaaaggcag tagatctggg acagagttca ctctcaccat cagcggcgtg    300
gagtgtgccg atgctgccac ttactactgt caacagggtt atagtagtac taatgttgat    360 aatatttcg gcggagggac cgaggtggtg gtcaaa                               396
```

<210> SEQ ID NO 62
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

```
Ser Thr Ser Gly Ser Gly Lys Pro Gly Ser Gly Glu Gly Ser Thr
1               5                   10                  15
```

ANTIGEN BINDING MOLECULES AND METHODS OF USE THEREOF

CROSS REFERENCE TO RELATED APPLICATIONS

This application is a divisional of U.S. application Ser. No. 16/138,542, filed Sep. 21, 2018, now U.S. Pat. No. 10,844,371, which claims priority to U.S. Provisional Application No. 62/562,231, filed Sep. 22, 2017, both of which are incorporated herein in their entirety.

SEQUENCE LISTING

The instant application contains a Sequence Listing which has been submitted electronically in ASCII format and is hereby incorporated by reference in its entirety. Said ASCII copy, created on Sep. 20, 2018, is named KPI-008US1_ST25.txt and is 24,514 bytes in size.

TECHNICAL FIELD

This disclosure relates to antigen binding molecules, such as antibodies, which specifically bind to the sequence GGGS (SEQ ID NO: 1), GGGGS (SEQ ID NO: 46) or related sequences, molecules comprising these sequences and cells presenting such molecules, polynucleotides encoding such antigen binding molecules, as well as humanized forms of the antigen binding molecules; methods of using the antigen binding molecules are also disclosed.

BACKGROUND

Antigen binding molecules, including antibodies, are used in immunotherapy and solid phase-based applications such as biosensors, affinity chromatography, and immunoassays. These antibodies and antigen binding molecules gain their utility by virtue of their ability to specifically bind their targets.

Linker sequences, which are often peptide-based when employed in biotechnological and biotherapeutic applications, may serve a range of scientifically-relevant applications. For example, a linker may be used as simply a spacer moiety in order to impart a desired structural and/or functional property to a larger molecule. In another example, a linker may impart little or no structural or functional properties to a larger molecule, but may be used as a distinguishing feature (e.g., a "marker" or "biomarker" or "tag"), uniquely identifying a larger molecule. In still another example, a linker may be used to impart a recognizable feature that may serve as a binding site for an antibody directed against a larger molecule comprising the linker sequence.

When a linker sequence is used as a distinguishing, detectable or identifiable feature of a larger molecule, an antibody that specifically binds the linker sequence, to the exclusion of other sequences present in the larger molecule, the antibody may serve as a detection agent. Such antibodies may be labeled with a moiety that is detectable under certain conditions. Additional applications for such an antibody include purification and isolation of a molecule comprising the linker, characterization of a molecule in a particular setting, enrichment of the concentration of a population of molecules comprising and/or presenting the linker, and therapeutic applications as well.

Disclosed herein are antigen binding molecules, including antibodies, that specifically bind the sequence GGGS (SEQ ID NO: 1) and/or GGGGS (SEQ ID NO: 46), molecules comprising these sequences and cells presenting such molecules. Applications and uses thereof are also disclosed.

SUMMARY

In one aspect, the present invention provides an isolated antigen binding molecule that specifically binds to a polypeptide comprising the amino acid sequence GGGS (SEQ ID NO: 1).

In some embodiments, the polypeptide comprising the amino acid sequence GGGS (SEQ ID NO: 1) is a protein. In some embodiments, the polypeptide comprises the amino acid sequence GGGS (SEQ ID NO: 1) at the N-terminus, C-terminus, between domains, or in loops.

In some embodiments, the polypeptide is a chimeric antigen receptor (CAR).

In some embodiments, the antigen binding molecule is a humanized antigen binding molecule. In other embodiments, the antigen binding molecule is selected from the group consisting of an antibody, a scFv, a Fab, a Fab', a Fv, a F(ab')2, a dAb, a human antibody, a humanized antibody, a chimeric antibody, a monoclonal antibody, a polyclonal antibody, a recombinant antibody, an IgE antibody, an IgD antibody, an IgM antibody, an IgA antibody, an IgG1 antibody, an IgG1 antibody having at least one mutation in the hinge region, an IgG2 antibody an IgG2 antibody having at least one mutation in the hinge region, an IgG3 antibody, an IgG3 antibody having at least one mutation in the hinge region, an IgG4 antibody, an IgG4 antibody having at least one mutation in the hinge region, an antibody comprising at least one non-naturally occurring amino acid, and any combination thereof. In certain embodiments, the antigen binding molecule comprises an antibody.

In some embodiments, the antigen binding molecule comprises a heavy chain (HC). In certain embodiments, the antigen binding molecule comprises a heavy chain CDR1 selected from the group consisting of SEQ ID NOs: 26, 28 and 30. In some embodiments, the antigen binding molecule comprises a heavy chain CDR2 selected from the group consisting of SEQ ID NOs: 27, 29 and 31. In some embodiments, the antigen binding molecule comprises a heavy chain CDR3 selected from the group consisting of SEQ ID NOs: 19, 22 and 25.

In some embodiments, the HC comprises a heavy chain variable region (VH) sequence selected from the group consisting of SEQ ID NO: 2, SEQ ID NO: 4, and SEQ ID NO: 6. In some embodiments, the VH amino acid sequence is at least about 70%, at least about 75%, at least about 80%, at least about 85%, at least about 90%, at least about 95%, at least about 96%, at least about 97%, at least about 98%, at least about 99%, or about 100% identical to a VH of an antigen binding molecule comprising SEQ ID NOs: 19, 22 and 25.

In some embodiments, the antigen binding molecule comprises a light chain (LC). In some embodiments, the antigen binding molecule comprises a light chain CDR1 selected from the group consisting of SEQ ID NOs: 8, 11 and 14. In some embodiments, the antigen binding molecule comprises a light chain CDR2 selected from the group consisting of SEQ ID NOs: 9, 12 and 15. In some embodiments, the antigen binding molecule comprises a light chain CDR3 selected from the group consisting of SEQ ID NOs: 10, 13 and 16.

In some embodiments, the LC comprises a light chain variable region (VL) sequence selected from the group consisting of SEQ ID NO: 3, SEQ ID NO: 5, and SEQ ID NO: 7. In some embodiments, the VL amino acid sequence is at least about 70%, at least about 75%, at least about 80%, at least about 85%, at least about 90%, at least about 95%, at least about 96%, at least about 97%, at least about 98%, at least about 99%, or about 100% identical to a VL of an antigen binding molecule comprising a light chain sequence selected from the group consisting of SEQ ID NO: 3, SEQ ID NO: 5, and SEQ ID NO: 7.

In some aspects, the antigen binding molecule comprises: (a) a VH CDR1 region comprising the amino acid sequence of SEQ ID NO: 26; (b) a VH CDR2 region comprising the amino acid sequence of SEQ ID NO: 27; (c) a VH CDR3 region comprising the amino acid sequence of SEQ ID NO: 19; (d) a VL CDR1 region comprising the amino acid sequence of SEQ ID NO: 8; (e) a VL CDR2 region comprising the amino acid sequence of SEQ ID NO: 9; and (f) a VL CDR3 region comprising the amino acid sequence of SEQ ID NO: 10.

In one aspect, the antigen binding molecule comprises: (a) a VH comprising the amino acid sequence of SEQ ID NO: 2; and (b) a VL comprising the amino acid sequence of SEQ ID NO: 3.

In one aspect, the antigen binding molecule comprises: (a) a VH CDR1 region comprising the amino acid sequence of SEQ ID NO: 28; (b) a VH CDR2 region comprising the amino acid sequence of SEQ ID NO: 29; (c) a VH CDR3 region comprising the amino acid sequence of SEQ ID NO: 22; (d) a VL CDR1 region comprising the amino acid sequence of SEQ ID NO: 11; (e) a VL CDR2 region comprising the amino acid sequence of SEQ ID NO: 12; and (f) a VL CDR3 region comprising the amino acid sequence of SEQ ID NO: 13.

In some embodiments, the antigen binding molecule comprises: (a) a VH comprising the amino acid sequence of SEQ ID NO: 4; and (b) a VL comprising the amino acid sequence of SEQ ID NO: 5.

In one aspect, the antigen binding molecule comprises: (a) a VH CDR1 region comprising the amino acid sequence of SEQ ID NO: 30; (b) a VH CDR2 region comprising the amino acid sequence of SEQ ID NO: 31; (c) a VH CDR3 region comprising the amino acid sequence of SEQ ID NO: 25; (d) a VL CDR1 region comprising the amino acid sequence of SEQ ID NO: 14; (e) a VL CDR2 region comprising the amino acid sequence of SEQ ID NO: 15; and (f) a VL CDR3 region comprising the amino acid sequence of SEQ ID NO: 16.

In some embodiments, the antigen binding molecule comprises: (a) a VH comprising the amino acid sequence of SEQ ID NO: 6; and (b) a VL comprising the amino acid sequence of SEQ ID NO: 7.

In some embodiments, the antigen binding molecule binds to a molecule comprising GGGGSGGGGSGGGGS (SEQ ID NO: 45). In some embodiments, the antigen binding molecule binds to a molecule comprising GGGSGKPGSGEGGGS (SEQ ID NO: 47). In some embodiments, the antigen binding molecule binds to a molecule comprising GGGGSGKPGSGEGGGGS (SEQ ID NO: 48). In some embodiments, the antigen binding molecule binds to a molecule comprising GGGGSGKPGSGGGGS (SEQ ID NO:49). In some embodiments, the antigen binding molecule binds to a molecule comprising GGGGSGKPGSGEGGS (SEQ ID NO: 50). In some embodiments, the antigen binding molecule binds to a molecule comprising GGGGSGKPGSGEGGGS (SEQ ID NO: 51). In some embodiments, the antigen binding molecule binds to a molecule comprising GGGGSGKPGSGEGGGGS (SEQ ID NO: 52). In some embodiments, the antigen binding molecule binds to a molecule comprising GGGGSGGGGSGGGGSG (SEQ ID NO: 53). In some embodiments, the antigen binding molecule binds to a molecule comprising GGGGGSGGGGSGGGGS (SEQ ID NO: 54). In some embodiments, the antigen binding molecule binds to a molecule comprising GGGGSGGGGSGGGGGS SEQ ID NO: 55.

In some embodiments, the antigen binding molecule further comprises a detectable label. In certain embodiments, the detectable label is selected from the group consisting of a fluorescent label, a photochromic compound, a proteinaceous fluorescent label, a magnetic label, a radiolabel, and a hapten. In further embodiments, the fluorescent label is selected from the group consisting of an Atto dye, an Alexafluor dye, quantum dots, Hydroxycoumarin, Aminocouramin, Methoxycourmarin, Cascade Blue, Pacific Blue, Pacific Orange, Lucifer Yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhocamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midorishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry.

In one aspect, the present invention provides a composition comprising the antigen binding molecules described herein. In another aspect, the present invention provides a polynucleotide encoding the heavy chain of an antigen binding molecule described herein. In one aspect, the present invention provides a polynucleotide encoding the light chain of an antigen binding molecule described herein. In some embodiments, the present invention provides a vector comprising the polynucleotides described herein.

In some embodiments, the present invention provides a cell comprising a vector described herein. In some embodiments, the cell is selected from the group consisting of a CHO cell, a Sp2/0 cell, a rabbit cell and an *E. coli* cell. In one aspect, the present invention provides a method of making an antigen binding molecule described herein comprising incubating the cell under suitable conditions.

In one aspect, the present invention provides a method of determining a number of cells presenting a polypeptide comprising the amino acid sequence GGGS (SEQ ID NO: 1), wherein the method comprises: (a) providing a sample comprising cells known or suspected to be presenting a polypeptide comprising the amino acid sequence GGGS (SEQ ID NO: 1); (b) contacting the sample with an antigen binding molecule described herein, under conditions that permit binding of the polypeptide and the antigen binding molecule; and (c) determining the number of cells presenting the polypeptide in the sample.

In another aspect, the present invention provides a method of isolating a polypeptide comprising the amino acid sequence GGGS (SEQ ID NO: 1), wherein the method comprises: (a) providing a sample known or suspected to comprise a polypeptide comprising the amino acid sequence GGGS (SEQ ID NO: 1); (b) contacting the sample with an antigen binding molecule of described herein, under conditions that permit binding of the polypeptide and the antigen binding molecule; and (c) separating any unbound molecules.

In still a further aspect, the present invention provides a method of determining the presence or absence of a polypeptide comprising the amino acid sequence GGGS (SEQ ID NO: 1), wherein the method comprises: (a) providing a sample known or suspected to comprise a polypeptide comprising the amino acid sequence GGGS (SEQ ID NO: 1); (b) contacting the sample with an antigen binding molecule described herein, under conditions that permit binding of the polypeptide and the antigen binding molecule; and (c) detecting the presence or absence of a polypeptide:antigen binding molecule complex.

BRIEF DESCRIPTION OF THE FIGURES

FIGS. 1A, 1B and 1C show the complementary determining region of exemplary antigen binding molecules provided herein according to Kabat, Clothia, and IMGT naming conventions, respectively.

FIG. 2 shows the heavy chain variable region and light chain variable region sequences of exemplary antigen binding molecules clone 132, clone 154, and clone 163.

DETAILED DESCRIPTION

Figure 3:
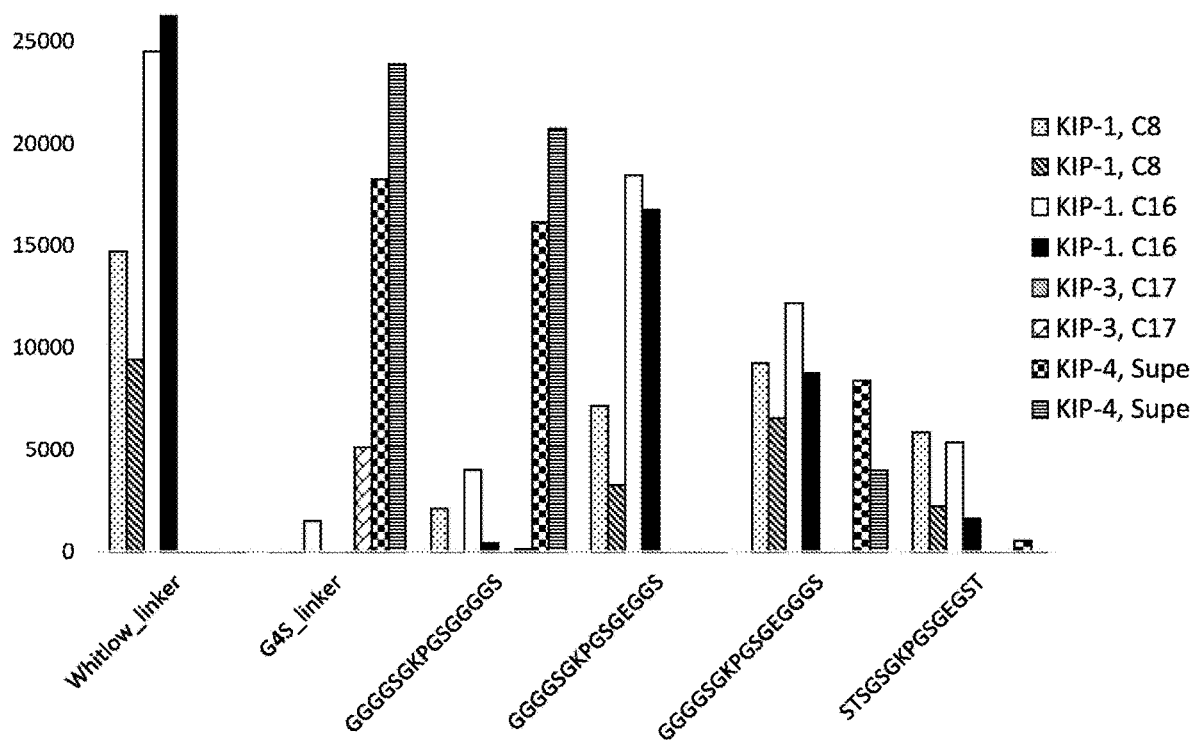
FIG. 3 shows a bar graph of the results of antibody binding profiles of polypeptide linkers (SEQ ID NOs 46, 49-51 and 62, respectively).

The present disclosure relates to antigen binding molecules, including antibodies, which specifically bind a moiety comprising the sequence GGGGS (SEQ ID NO: 46) and subsequences thereof, particularly GGGS (SEQ ID NO: 1), as well as humanized forms of the antigen binding molecules, molecules comprising SEQ ID NOs: 1 and/or 45-55, cells presenting such molecules, polynucleotides encoding the molecules, and vectors comprising the polynucleotides; in vitro cells comprising the polynucleotides and vectors are also disclosed.

In some embodiments, the antigen binding molecules binds to a molecule comprising GGGGSGGGGSGGGGS (SEQ ID NO: 45), GGGGS (SEQ ID NO: 46), GGGSGKPGSGEGGGS (SEQ ID NO: 47), GGGSGKPGSGEGGGGS (SEQ ID NO: 48), GGGGSGKPGSGGGGS (SEQ ID NO: 49), GGGGSGKPGSGEGGS (SEQ ID NO: 50), GGGGSGKPGSGEGGGS (SEQ ID NO: 51), GGGGSGKPGSGEGGGGS (SEQ ID NO: 52), GGGGSGGGGSGGGGSG (SEQ ID NO: 53), GGGGGSGGGGSGGGGS (SEQ ID NO: 54), GGGGSGGGGSGGGGGS (SEQ ID NO: 55), or subsequences thereof.

Methods of using the disclosed antigen binding molecules are provided. The antigen binding molecules, polynucleotides, vectors, in vitro cells and methods described herein may be used in a range of applications, e.g., as reagents to detect the presence of molecules comprising GGGGS (SEQ ID NO: 46) and subsequences thereof, particularly GGGS (SEQ ID NO: 1), and cells presenting such molecules, quantifying the amount of a molecule comprising SEQ ID NOs: 1 and/or 46, molecules and cells presenting such molecules, screening for molecules comprising SEQ ID NOs: 1 and/or 46, and cells presenting such molecules, purifying molecules comprising SEQ ID NOs: 1 and/or 46, and cells presenting such molecules, and biomarker studies focused on molecules comprising SEQ ID NOs: 1 and/or 46, and cells presenting such molecules. Therapeutic uses are also provided, for example applications in which the biological activity of a molecule comprising SEQ ID NOs: 1 and/or 46, and cells presenting such molecules, is modulated (enhanced or repressed), as well as dose ranging studies related to therapeutics comprising SEQ ID NOs: 1 and/or 46, and cells presenting such molecules.

The antigen binding molecules (antibodies) disclosed herein were generated from hybridomas generated using B-cells of rabbit origin, but may be readily humanized using standard methods known to those of skill in the art, as well as those described herein.

I. Definitions

In order that the present disclosure may be more readily understood, certain terms are first defined. As used in this application, except as otherwise expressly provided herein, each of the following terms shall have the meaning set forth below. Additional definitions are set forth throughout the application. The headings provided herein are not limitations of the various aspects of the disclosure, which aspects may be understood by reference to the specification as a whole.

It is understood that wherever aspects are described herein with the language "comprising," otherwise analogous aspects described in terms of "consisting of" and/or "consisting essentially of" are also provided.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, *The Concise Dictionary of Biomedicine and Molecular Biology*, 2$^{nd}$ ed., (2001), CRC Press; *The Dictionary of Cell & Molecular Biology*, 5$^{th}$ ed., (2013), Academic Press; and *The Oxford Dictionary Of Biochemistry And Molecular Biology*, Cammack et al. eds., 2$^{nd}$ ed, (2006), Oxford University Press, provide those of skill in the art with a general dictionary for many of the terms used in this disclosure.

As used herein, the twenty conventional (e.g., naturally occurring) amino acids and their abbreviations follow conventional usage. See, e.g., *Immunology—A Synthesis* (2nd Edition), Golub and Green, eds., Sinauer Assoc., Sunderland, Mass. (1991), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids may also be suitable components for polypeptides of the present invention. Examples of unconventional amino acids include: 4-hydroxyproline, gamma-carboxyglutamate, epsilon-N,N,N-trimethyllysine, e-N-acetyllysine, O-phosphoserine, N-acetylserine, N-formylmethionine, 3-methylhistidine, 5-hydroxylysine, sigma-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As used herein, the term the terms "a" and "an" are used per standard convention and mean one or more, unless context dictates otherwise.

As used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" may mean within one or more than one standard deviation per the practice in the art. Alternatively, "about" or "comprising essentially of" may mean a range of up to 10% (i.e., ±10%). For example, about 5 mg may include any number between 4.5 mg and 5.5 mg. Furthermore, particularly with respect to biological systems or processes, the terms may mean up to an order of magnitude or up to 5-fold of a value. When particular values or compositions are provided in the instant disclosure, unless otherwise stated, the meaning of "about" or "comprising essentially of should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

As used herein, the term "and/or" is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as 'A, B, and/or C" is intended to encompass each of the following aspects: A, B, and C; A, B, or C; A or C; A or B; B or C; A and C; A and B; B and C; A (alone); B (alone); and C (alone).

As used herein, the term the use of the alternative (e.g., "or") should be understood to mean either one, both, or any combination thereof of the alternatives.

As used herein, the term "allogeneic" refers to any material derived from one individual which is then introduced to another individual of the same species, e.g., allogeneic T cell transplantation.

As used herein, the term "antibody" (Ab) includes, without limitation, a glycoprotein immunoglobulin which binds specifically to an antigen. In general, an antibody may comprise at least two heavy (HC) chains and two light (LC) chains interconnected by disulfide bonds, or an antigen binding molecule thereof. Each HC chain comprises a heavy chain variable region (abbreviated herein as VH) and a heavy chain constant region. The heavy chain constant region comprises three constant domains, CH1, CH2 and CH3. Each LC chain comprises a light chain variable region (abbreviated herein as VL) and a light chain constant region. The light chain constant region comprises one constant domain, CL. The VH and VL regions may be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component of the classical complement system (C1q).

The term "antibody" also encompasses an intact immunoglobulin or an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')2, Fv, domain antibodies (dAbs), fragments including complementarity determining regions (CDRs), single-chain antibodies (scFv), chimeric antibodies, diabodies, triabodies, tetrabodies, and polypeptides that contain at least a portion of an immunoglobulin that is sufficient to confer specific antigen binding to the polypeptide.

The term "antibody" includes, both naturally occurring and non-naturally occurring (recombinantly-produced) antibodies, human and non-human antibodies (e.g., camelid, murine, rabbit), monospecific antibodies, multispecific antibodies (including bispecific antibodies), immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies (see, e.g., Stocks, (2004) *Drug Discovery Today* 9(22): 960-66), antibody fusions (which term encompasses antibody-drug conjugates) and which are sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments thereof. In certain embodiments, antibodies described herein refer to polyclonal antibody populations.

A non-human antibody may be humanized using recombinant methods to reduce its immunogenicity in humans, as disclosed herein with respect to antibodies that specifically bind GGGGS (SEQ ID NO: 46) and subsequences thereof, particularly GGGS (SEQ ID NO: 1), molecules comprising this sequence and cells presenting such molecules. Where not expressly stated, and unless the context indicates otherwise, the term "antibody" also includes an antigen-binding fragment of an antigen binding molecule of any of the aforementioned immunoglobulins, and includes a monovalent and a divalent fragment or portion, and a single chain antibody (i.e., a scFv).

In various embodiments, an antibody specifically binds GGGS (SEQ ID NO: 1), molecules comprising this sequence and cells presenting such molecules. In some embodiments, the antibody specifically binds to a CAR (or component thereof) comprising SEQ ID NOs: 1, and/or 45-55, molecules comprising this sequence, and cells presenting such molecules; cells presenting SEQ ID NOs: 1, and/or 45-55 can, but need not be, an immune cell, such as a T cell.

As used herein, the term "antigen" means any molecule that provokes an immune response or is capable of being bound by an antibody or other antigen binding molecule. The immune response may involve either antibody production, or the activation of specific immunologically-competent cells, or both. Those of skill in the art will readily understand that any macromolecule, including virtually all proteins or peptides (including SEQ ID NOs: 1, and/or 45-55), molecules comprising this sequence and cells presenting such molecules), may serve as an antigen. Generally, an antigen may be endogenously expressed, i.e. expressed by genomic DNA, or it may be recombinantly expressed, or it may be chemically synthesized. In one particular embodiment, an antigen comprises all or a portion of GGGGS (SEQ ID NO: 46) and subsequences thereof, particularly GGGS (SEQ ID NO: 1), molecules comprising these sequences, which is optionally conjugated to an adjuvant such as keyhole limpet hemocyanin (KLH).

As used herein, the term "antigen binding molecule" means a protein comprising a portion that binds to an antigen or target protein and, optionally, a scaffold or framework portion that allows the antigen binding portion to adopt a conformation that promotes binding of the antigen binding molecule to the antigen. Examples of the representative types of antigen binding molecules include a scFv, a human, mouse or rabbit antibody; a humanized antibody; a chimeric antibody; a recombinant antibody; a single chain antibody; a diabody; a triabody; a tetrabody; a Fab fragment; a F(ab')2 fragment; an IgD antibody; an IgE antibody; an IgM antibody; an IgG1 antibody; an IgG2 anti-body; an IgG3 antibody; or an IgG4 antibody, and fragments thereof.

An antigen binding molecule may comprise, for example, an alternative protein scaffold or artificial scaffold with grafted complementarity determining regions (CDRs) or CDR derivatives. Such scaffolds include, but are not limited to, antibody-derived scaffolds comprising mutations introduced to, for example, stabilize the three-dimensional structure of the antigen binding molecule as well as wholly synthetic scaffolds comprising, for example, a biocompatible polymer. See, e.g., Komdorfer et al., 2003, *Proteins: Structure, Function, and Bioinformatics,* 53(1):121-129 (2003); Roque et al., *Biotechnol. Prog.* 20:639-654 (2004). In addition, peptide antibody mimetics ("PAMs") may be used, as well as scaffolds based on antibody mimetics utilizing various components (e.g., fibronectin) as a scaffold. An antigen binding molecule may have, for example, the structure of a naturally occurring immunoglobulin.

An antigen binding molecule may have one or more binding sites. If there is more than one binding site, the binding sites may be identical to one another or they may be different. For example, a naturally occurring human immunoglobulin typically has two identical binding sites, while a "bispecific" or "bifunctional" antibody has two different binding sites, and is capable of specifically binding two different antigens (e.g., SEQ ID NOs:1 and/or 45-55) and a cell surface activator molecule.

In various embodiments, an antigen binding molecule is an antibody or fragment thereof, including one or more of the complementarity determining regions (CDRs) disclosed herein and shown in FIGS. 1A, 1B and 1C, which specifically bind GGGGS (SEQ ID NO: 46) and subsequences thereof, particularly GGGS (SEQ ID NO: 1), molecules comprising SEQ ID NOs: 1 and/or 45-55, and cells presenting such molecules. In further embodiments, the antigen binding molecule binds to a CAR comprising the SEQ ID NOs: 1 and/or 45-55, and may be expressed on an immune cell, such as a T cell.

The term "autologous" refers to any material derived from the same individual to which it is later to be re-introduced. For example, the engineered autologous cell therapy (eACT™) methods described herein involve collection of lymphocytes from a patient, which are then engineered to express a construct, e.g., a CAR construct, and then administered back to the same patient.

As used herein, the term "binding affinity" means the strength of the sum total of non-covalent interactions between a single binding site of a molecule (e.g., an antigen binding molecule such as an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y may generally be represented by the dissociation constant ($K_D$). Affinity may be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody-antigen complex. The $k_{on}$ and $k_{off}$ may be determined by standard techniques known to one of ordinary skill in the art, such as BIAcore® or KinExA or surface plasmon resonance.

As used herein, the term "complementarity determining region" or "CDR" means an amino acid sequence that contributes to antigen binding specificity and affinity. Framework regions may aid in maintaining the proper confirmation of the CDRs to promote binding between the antigen binding molecule and an antigen. There are three CDRs in each of the variable regions of the heavy chain and the light chain, which are designated CDR1, CDR2 and CDR3, for each of the variable regions. The exact boundaries of CDRs have been defined differently according to different systems.

A number of definitions of the CDRs are commonly in use: Kabat numbering, Chothia numbering, AbM numbering, or contact numbering. The AbM definition is a compromise between the Kabat and Chothia systems, and is used by Oxford Molecular's AbM antibody modelling software.

The system described by Kabat (Kabat et al., Sequences of Proteins of Immunological Interest (National Institutes of Health, Bethesda, Md. (1987) and (1991)) provides a residue numbering system applicable to any variable region of an antibody, and also provides precise residue boundaries defining the three CDRs.

Chothia and coworkers (Chothia and Lesk, (1987) *J. Mol. Biol.,* 196:901-917; and Chothia et al., (1989) *Nature,* 342: 877-883) found that certain sub-portions within Kabat CDRs adopt nearly identical peptide backbone conformations, despite having great diversity at the level of amino acid sequence. Chothia CDRs have boundaries that overlap with Kabat CDRs. Other boundaries defining CDRs overlapping with the Kabat CDRs have been described by Padlan et al. ((1995) *FASEB J.,* 9:133-139) and MacCallum et al. ((1996) *J. Mol. Biol.,* 262(5):732-745). Still other CDR boundary definitions may not strictly follow one of the described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although exemplary embodiments use Chothia defined CDRs.

Table A defines CDRs using each numbering system. The contact definition is based on an analysis of the available complex crystal structures.

TABLE A

| Loop | Kabat | AbM | Chothia | Contact |
|------|-------|-----|---------|---------|
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B | H26--H35B | H26--H32 . . . 34 | H30--H35B |
| H1 | H31--H35 | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen binding molecule thereof. In certain aspects, the CDRs of an antibody may be determined according to the Kabat numbering system (see, e.g., Kabat et al. in Sequences of *Proteins of Immunological Interest*, 5th Ed., NIH Publication 91-3242, Bethesda MD 1991). Using the Kabat numbering system, CDRs within an antibody heavy chain molecule are typically present at amino acid positions 31 to 35, which optionally may include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein may be described according to the Kabat numbering scheme although they may readily be construed in other numbering systems using Table A.

In certain aspects, the CDRs of an antibody may be determined according to the Chothia numbering scheme, which refers to the location of immunoglobulin structural loops (see, e.g., Chothia C & Lesk A M, (1987), *J Mol Biol* 196: 901-917; Al-Lazikani B et al., (1997) *J Mol Biol* 273: 927-948; Chothia C et al., (1992) *J Mol Biol* 227: 799-817; Tramontano A et al., (1990) *J Mol Biol* 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). See Table A. In a specific embodiment, the CDRs of the antibodies described herein have been determined according to the Chothia numbering scheme, as shown in FIG. 1A.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen binding molecule provided herein (or fragment thereof) may be replaced with an amino acid residue with a similar side chain.

Conservative amino acid substitutions, which are encompassed by the present disclosure, may encompass non-naturally occurring amino acid residues, which are typically incorporated by chemical peptide synthesis rather than by synthesis in biological systems. These include peptidomimetics and other reversed or inverted forms of amino acid moieties. Naturally occurring residues may be divided into classes based on common side chain properties:

hydrophobic: norleucine, Met, Ala, Val, Leu, Ile;
neutral hydrophilic: Cys, Ser, Thr, Asn, Gln;
acidic: Asp, Glu;
basic: His, Lys, Arg;
residues that influence chain orientation: Gly, Pro; and
aromatic: Trp, Tyr, Phe.

Non-conservative substitutions may involve the exchange of a member of one of these classes for a member from another class. Such substituted residues may be introduced, for example, into regions of a human antibody that are homologous with non-human antibodies, or into the non-homologous regions of the molecule. Exemplary conservative amino acid substitutions are set forth in Table B below.

TABLE B

| Original Residues | Exemplary Substitutions | Preferred Substitutions |
|-------------------|-------------------------|-------------------------|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which may exhibit various effector functions, such as interaction with the Fc receptor. The constant region of an immunoglobulin molecule generally has a more conserved amino acid sequence relative to an immunoglobulin variable domain.

As used herein, the term "cross competes" means the situation in which the interaction between an antigen and a first antigen binding molecule or binding fragment thereof blocks, limits, inhibits, or otherwise reduces the ability of a reference antigen binding molecule or binding fragment thereof to interact with the antigen. Cross competition may be complete, e.g., binding of the binding molecule to the antigen completely blocks the ability of the reference binding molecule to bind the antigen, or it may be partial, e.g., binding of the binding molecule to the antigen reduces the ability of the reference binding molecule to bind the antigen. In certain embodiments, an antigen binding molecule that cross competes with a reference antigen binding molecule binds the same or an overlapping epitope as the reference antigen binding molecule. In other embodiments, the antigen binding molecule that cross competes with a reference antigen binding molecule binds a different epitope than the reference antigen binding molecule. Numerous types of competitive binding assays may be used to determine if one antigen binding molecule competes with another, for example: solid phase direct or indirect radioimmunoassay (RIA); solid phase direct or indirect enzyme immunoassay (EIA); sandwich competition assay (Stahli et al., (1983) *Method Enzymol* 9:242-53); solid phase direct biotin-avidin EIA (Kirkland et al., (1986) *J Immunol* 137:3614-19); solid phase direct labeled assay, solid phase direct labeled sandwich assay (Harlow and Lane, 1988, *Antibodies, A Laboratory Manual*, Cold Spring Harbor Press); solid phase direct label RIA using I$^{125}$ label (Morel et al., (1988) *Molec Immunol* 25:7-15); solid phase direct biotin-avidin EIA (Cheung et al., (1990) *Virology* 176:546-52); and direct labeled RIA (Moldenhauer et al., (1990) *Scand J Immunol* 32:77-82).

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding molecule (a derivative) may have a greater circulating half-life than an antigen binding molecule that is not chemically modified. In some embodiments, a derivative antigen binding molecule is covalently modified to include one or more water soluble polymer attachments, including, but not limited to, polyethylene glycol, polyoxyethylene glycol, or polypropylene glycol.

As used herein, the term "diabody" or dAB means bivalent antibodies comprising two polypeptide chains, wherein each polypeptide chain comprises VH and VL domains joined by a linker that is too short to allow for pairing between two domains on the same chain, thus allowing each domain to pair with a complementary domain on another polypeptide chain (see, e.g., Holliger et al., (1993) *Proc Natl Acad Sci U.S.A.* 90:6444-48, Poljak et al., (1994) *Structure* 2: 1121-23, and Perisic et al., (1994) *Structure* 2(12): 1217-26). If the two polypeptide chains of a diabody are identical, then a diabody resulting from their pairing will have two identical antigen binding sites. Polypeptide chains having different sequences may be used to make a diabody with two different antigen binding sites. Similarly, tribodies and tetrabodies are antibodies comprising three and four polypeptide chains, respectively, and forming three and four antigen binding sites, respectively, which may be the same or different.

As used herein, an "epitope" is a term in the art and refers to a localized region of an antigen to which an antibody may specifically bind. An epitope may be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds may be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giege et al., (1994) *Acta Crystallogr D Biol Crystallogr* 50 (Pt 4): 339-350; McPherson, (1990) *Eur J Biochem* 189: 1-23; Chayen, (1997) *Structure* 5: 1269-1274; McPherson, (1976) *J Biol Chem* 251: 6300-6303). Antibody:antigen crystals may be studied using well known X-ray diffraction techniques and may be refined using computer software such as X-PLOR (Yale University, 1992, distributed by Molecular Simulations, Inc.; see, e.g., *Meth Enzymol* (1985) Vols 114 & 115, eds Wyckoff et al.), and BUSTER (Bricogne, (1993) *Acta Crystallogr D Biol Crystallogr* 49 (Pt 1): 37-60; Bricogne, (1997) *Meth Enzymol* 276A: 361-423, ed. Carter; Roversi et al., (2000) *Acta Crystallogr D Biol Crystallogr* 56 (Pt 10): 1316-1323). Mutagenesis mapping studies may be accomplished using any method known to one of skill in the art. See, e.g., Champe et al., (1995) *J Biol Chem* 270: 1388-94 and Cunningham & Wells, (1989) *Science* 244: 1081-85 for a description of mutagenesis techniques, including alanine and arginine scanning mutagenesis techniques.

As used herein, the term "Fab fragment" means is a monovalent fragment having the VL, VH, CL and CH1 domains; a "F(ab')2 fragment" is a bivalent fragment having two Fab fragments linked by a disulfide bridge at the hinge region; a "Fv fragment" has the VH and VL domains of a single arm of an antibody; and a "dAb fragment" has a VH domain, a VL domain, or an antigen-binding fragment of a VH or VL domain.

As used herein, the terms "immunospecifically binds," "immunospecifically recognizes," "specifically binds," and "specifically recognizes" are analogous terms and are used interchangeably in the context of antigen binding molecules, and means that a given molecule preferentially binds to an antigen (e.g., epitope or immune complex) as such binding is understood by one skilled in the art. For example, an antigen binding molecule that specifically binds to an antigen may bind to other peptides or polypeptides, but with a comparatively lower affinity as determined by, e.g., immunoassays, BIAcore®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, molecules that specifically bind to an antigen (e.g., GGGGS (SEQ ID NO: 46) and subsequences thereof, particularly GGGS (SEQ ID NO: 1), molecules comprising this sequence and cells presenting such molecules) bind with a dissociation constant ($K_d$) of about $1 \times 10^{-7}$ M. In some embodiments, the antigen binding molecule specifically binds an antigen (e.g., SEQ ID NOs: 1 and/or 46, molecules comprising this sequence and cells presenting such molecules) with "high affinity" when the $K_d$ is about $1 \times 10^{-9}$ M to about $5 \times 10^{-9}$ M. In some embodiments, the antigen binding molecule specifically binds an antigen (e.g., SEQ ID NOs: 1 and/or 46, molecules comprising this sequence and cells presenting such molecules) with "very high affinity" when the $K_d$ is $1 \times 10^{-10}$ M to about $5 \times 10^{-10}$ M.

In still another embodiment, molecules that specifically bind to an antigen (e.g., SEQ ID NOs: 1 and/or 46, molecules comprising these sequences and cells presenting such molecules) do not cross react with other proteins under similar binding conditions. In another specific embodiment, molecules that specifically bind to an antigen (e.g., SEQ ID NOs: 1 and/or 46, molecules comprising these sequences and cells presenting such molecules) do not cross react with other proteins that do not comprise SEQ ID NOs: 1, and/or 46, molecules comprising these sequences and cells presenting such molecules. In a specific embodiment, provided herein is an antibody or fragment thereof that binds to SEQ ID NOs: 1 and/or 46, molecules comprising these sequences and cells presenting such molecules, with higher affinity than to another unrelated antigen. In certain embodiments, provided herein is an antigen binding molecule (e.g., an antibody) or fragment thereof that binds to SEQ ID NOs: 1 and/or 46, molecules comprising these sequences and cells presenting such molecules as molecules comprising this sequence and cells presenting such molecules, with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an antigen binding molecule, antibody or antigen binding fragment thereof that specifically binds SEQ ID NOs: 1 and/or 46, molecules comprising these sequences and cells presenting such molecules, described herein compared to an unrelated protein which does not comprise SEQ ID NOs: 1, and/or 46, is less than 10%, 15%, or 20% of the binding of the antibody to linker fragment protein as measured by, e.g., a radioimmunoassay.

As used herein, the term "heavy chain" when used in reference to an antibody may refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG$_1$, IgG$_2$, IgG$_3$ and IgG$_4$.

As used herein, the term "immunoglobulin" means an immune molecule from any of the commonly known isotypes, including but not limited to IgA, secretory IgA, IgG and IgM. IgG subclasses are also well known to those in the art and include but are not limited to human IgG1, IgG2, IgG3 and IgG4. Many of the molecules described herein are immunoglobulins. As used herein, "isotype" means the antibody class or subclass (e.g., IgM or IgG1) that is encoded by the heavy chain constant region genes.

An immunoglobulin is a tetrameric molecule, normally composed of two identical pairs of polypeptide chains, each pair having one "light" (about 25 kDa) and one "heavy" chain (about 50-70 kDa). The amino-terminal portion of each chain includes a variable region of about 100 to 130 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, or IgE, respectively. Within light and heavy chains, the variable and constant regions are joined by a "J" region of about 12 or more amino acids, with the heavy chain also including a "D" region of about 10 more amino acids. See generally, Berzofsky & Berkower, in *Fundamental Immunology* (Paul, (ed), Lippincott Williams & Wilkins (2012); which chapter and volume is incorporated by reference in its entirety for all purposes). The variable regions of each light/heavy chain pair form the antibody binding site such that an intact immunoglobulin has two primary binding sites.

Naturally occurring immunoglobulin chains exhibit the same general structure of relatively conserved framework regions (FR) joined by three hypervariable regions, also called complementarity determining regions or "CDRs." From N-terminus to C-terminus, both light and heavy chains comprise the domains FR1, CDR1, FR2, CDR2, FR3, CDR3 and FR4. The assignment of amino acids to each domain may be done in accordance with the definitions of Kabat (see, e.g., Kabat et al. in *Sequences of Proteins of Immunological Interest*, 5th Ed., NIH Publication 91-3242, Bethesda MD (1991)) or Chothia (Chothia, used herein, (see, e.g., Chothia & Lesk (1987), *J. Mol. Biol.* 196:901-917; Chothia et al., 1989, *Nature* 342:878-883 or Honegger & Pluckthun (2001), *J Mol Biol* 309:657-670). The Kabat, Chothia and Abm (Oxford Molecular) numbering systems are described more fully herein.

As used herein, the term "in vitro cell" refers to any cell that is cultured ex vivo. An in vitro cell may include a human cell such as a T cell or dendritic cell, or it may include CHO, sP2/0, rabbit and other non-human cells.

As used herein, the term "light chain" when used in reference to an antibody may refer to any distinct type, e.g., kappa (κ) or lambda (λ) based on the amino acid sequence of the constant domains. Light chain amino acid sequences are known in the art. In specific embodiments, the light chain is a human light chain.

The term "neutralizing" refers to an antigen binding molecule, scFv, antibody, or a fragment thereof, that binds to a ligand (e.g., a moiety comprising SEQ ID NOs: 1 and/or 46) and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "patient" means any human who is being treated for an abnormal physiological condition, such as cancer or has been formally diagnosed with a disorder, those without formally recognized disorders, those receiving medical attention, those at risk of developing the disorders, etc. The terms "subject" and "patient" are used interchangeably herein and include both human and non-human animal subjects.

As used herein, the terms "peptide," "polypeptide," and "protein" are used interchangeably herein, and mean a compound comprising amino acid residues covalently linked by peptide bonds. A polypeptide, protein or peptide must contain at least two amino acids, but no limitation is placed on the maximum number of amino acids that may comprise a protein's or peptide's amino acid sequence. As used herein, the term refers to both short chains, which also commonly are referred to as peptides, oligopeptides and oligomers, and to longer chains, which generally are referred to as proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The term "polypeptide" includes natural peptides, recombinant peptides, synthetic peptides, or a combination thereof.

In some aspects, the polypeptides and/or proteins have deletions from, additions to, and/or substitutions of one or more amino acids of antigen binding molecule. Useful polypeptide fragments may include immunologically functional fragments of antigen binding molecules, including not limited to one or more CDR regions, variable domains of a heavy and/or light chain, a portion of other portions of an antibody chain, and the like. Moieties that may be substituted for one or more amino acids of an antigen binding molecule include, e.g., D or L forms of amino acids, an amino acid different from the amino acid normally found in the same position of an antigen binding molecule, deletions, non-naturally occurring amino acids, and chemical analogs of amino acids.

Peptide analogs are commonly used in the pharmaceutical industry as non-peptide drugs with properties analogous to those of the template peptide and form an aspect of the instant disclosure. These types of non-peptide compound are termed "peptide mimetics" or "peptidomimetics." See, e.g., Fauchere, (1986) *Adv. Drug Res.* (Testa, ed.) 15:29-69; Veber & Freidinger, (1985) *TINS*, p. 392; and Evans et al., (1987) *J. Med. Chem,* 30:1229-39, which are incorporated herein by reference for any purpose.

Polypeptides, peptides, proteins and analogous molecules comprising SEQ ID NOs: 1 and/or 46, molecules comprising these sequences and cells presenting such molecules, are specifically encompassed by the terms.

As used herein, the term "percent identity" means the percent of identical residues between the amino acids or nucleotides in the compared molecules. For these calculations, gaps in alignments (if any) must be addressed by a particular mathematical model or computer program (i.e., an "algorithm"). Methods that may be used to calculate the identity of the aligned nucleic acids or polypeptides include those described in *Computational Molecular Biology*, (Lesk, ed.), (1988) New York: Oxford University Press; *Biocomputing Informatics and Genome Projects*, (Smith, ed.), 1993, New York: Academic Press; *Computer Analysis of Sequence Data, Part I*, (Griffin and Griffin, eds.), 1994, New Jersey: Humana Press; von Heinje, (1987) *Sequence Analysis in Molecular Biology*, New York: Academic Press; *Sequence Analysis Primer*, (Gribskov and Devereux, eds.), 1991, New York: M. Stockton Press; and Carillo et al., (1988) *J. Applied Math.* 48:1073.

In calculating percent identity, the sequences being compared are aligned in a way that gives the largest match between the sequences. The computer program used to determine percent identity may be, e.g., MOE (Chemical Computing Group) or DNASTAR (University of Wisconsin, Madison, WI). The computer algorithm GAP may be used to align the two polypeptides or polynucleotides for which the percent sequence identity is to be determined. The sequences are aligned for optimal matching of their respective amino acid or nucleotide (the "matched span," as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. In certain embodiments, a standard comparison matrix (see, e.g., Dayhoff et al., (1978) *Atlas of Protein Sequence and Structure* 5:345-352 for the PAM 250 comparison matrix; Henikoff et al., (1992) *Proc. Nat. Acad. Sci. U.S.A.* 89: 10915-10919 for the BLOSUM 62 comparison matrix) is also used by the algorithm.

Certain alignment schemes for aligning two amino acid sequences may result in matching of only a short region of the two sequences, and this small aligned region may have very high sequence identity even though there is no significant relationship between the two full-length sequences. Accordingly, the selected alignment method (e.g., the GAP program) may be adjusted if desired to result in an alignment that spans at least 50 contiguous amino acids of the target polypeptide.

As used herein, the terms "single-chain antibody" and "single chain fragment variable (scFv)" are used interchangeably and mean an antigen binding molecule in which a VL and a VH region are joined via a linker to form a continuous protein chain wherein the linker is long enough to allow the protein chain to fold back on itself and form a monovalent antigen binding site (see, e.g., Bird et al., (1988) *Science* 242:423-26 and Huston et al., (1988) *Proc. Nat. Acad. Sci. U.S.A.* 85:5879-83 (1988). FMC63 (Nicholson et al., (1997) *Mol. Immunol.* 34:(16-17) 1157-65) is a specific example of a scFv, and is specific for CD19.

A "therapeutically effective amount," "effective dose," "effective amount," or "therapeutically effective dosage" of a therapeutic agent, (e.g., a moiety comprising SEQ ID NOs: 1, and/or 46, molecules comprising these sequences and cells presenting such molecules), is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression may be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Hartl and Jones (1997) *Genetics: Principles and Analysis,* 4$^{th}$ ed, Jones & Bartlett). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

As used herein, the terms "variable region" or "variable domain" are used interchangeably and mean a portion of an antibody, generally, a portion of a light or heavy chain, typically the amino-terminal end of the antibody, and comprising about 100-130 amino acids in the heavy chain and about 90 to 115 amino acids in the light chain, which differ extensively in sequence among antibodies and are used in the binding and specificity of a particular antibody for a particular antigen. The variability in sequence is concentrated in those regions called complementarity determining regions (CDRs) while the more highly conserved regions in the variable domain are called framework regions (FR). The CDRs of the light and heavy chains are primarily responsible for the interaction and specificity of the antibody with antigen.

In certain embodiments, the variable region of an antigen binding molecule is a human variable region. In further embodiments, the variable region comprises rodent, human or murine CDRs and human framework regions (FRs). In further embodiments, the variable region is a primate (e.g., a non-human primate) variable region. In yet further embodiments, the variable region is a rabbit variable region. In other embodiments, the variable region comprises human CDRs and non-human (e.g., rabbit, murine, rat or non-human primate) framework regions (FRs). In other embodiments, the variable region comprises non-human (e.g., rabbit, murine, rat or non-human primate) CDRs and human framework regions (FRs).

The terms "VH," "VH domain" and "VH chain" are used interchangeably and mean the heavy chain variable region of an antigen binding molecule, antibody or an antigen binding fragment thereof.

The terms "VL," "VL domain" and "VL chain" are used interchangeably and mean the light chain variable region of an antigen binding molecule, antibody or an antigen binding fragment thereof.

Various aspects of the invention are described in further detail in the following subsections.

II. Antigen Binding Molecules and Polynucleotides Encoding the Same

The present disclosure is directed to antigen binding molecules, including antibodies, that specifically bind GGGGS (SEQ ID NO: 46) and subsequences thereof, particularly GGGS (SEQ ID NO: 1), molecules comprising these sequences and cells presenting such molecules, and/or antigen binding molecules which cross compete with one or more antigen binding molecules described herein (i.e., one or more of those described in FIG. 2 and/or disclosed in the appended Sequence Listing). Polynucleotides encoding the antigen binding molecules are also provided, and form an aspect of the instant disclosure.

An antibody or antigen binding molecule encoded of the present invention may be single chained or double chained. In some embodiments, the antibody or antigen binding molecule is single chained. In certain embodiments, the antigen binding molecule is selected from the group consisting of a scFv, a Fab, a Fab', a Fv, a F(ab')2, a dAb, and any combination thereof. In one particular embodiment, the antibody or antigen binding molecule comprises a scFv.

In certain embodiments, an antigen binding molecule such as an antibody comprises a single chain, wherein the heavy chain variable region and the light chain variable region are connected by a linker (a scFv). In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises between about 8 amino acids and about 18 amino acids (e.g., 10 amino acids).

In some embodiments, the antigen binding molecules of the present invention specifically bind to GGGGS (SEQ ID NO: 46) and subsequences thereof, particularly GGGS (SEQ ID NO: 1), molecules comprising these sequences and cells presenting such molecules. In certain embodiments, an antigen binding molecule of the present disclosure specifically binds SEQ ID NOs: 1, and/or 46, as well as molecules comprising these sequences and cells presenting such molecules, with a $K_D$ of less than $1\times10^{-6}$ M, less than $1\times10^{-7}$ M, less than $1\times10^{-8}$ M, or less than $1\times10^{-9}$ M. In one particular embodiment, an antigen binding molecule specifically binds to SEQ ID NOs: 1, and/or 46, as well as molecules comprising these sequences and cells presenting such molecules, with a $K_D$ of less than $1\times10^{-7}$ M. In another embodiment, an antigen binding molecule specifically binds SEQ ID NOs: 1, and/or 46, as well as molecules comprising these sequences and cells presenting such molecules, with a $K_D$ of less than $1\times10^{-8}$ M. In some embodiments, an antigen binding molecule binds the scFv FMC63, as well as molecules comprising this sequence and cells presenting such molecules, with a $K_D$ of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-8}$ M, about $2\times10^{-8}$ M, about $3\times10^{-8}$ M, about $4\times10^{-8}$ M, about $5\times10^{-8}$ M, about $6\times10^{-8}$ M, about $7\times10^{-8}$ M, about $8\times10^{-8}$ M, about $9\times10^{-8}$ M, about $1\times10^{-9}$ M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$ M, about $9\times10^{-9}$ M, about $1\times10^{-10}$ M, or about $5\times10^{-10}$ M. $K_D$ may be calculated using standard methodologies, as described herein.

In specific embodiments, an antigen binding molecule of the instant disclosure is an antibody identified herein as Clone 132, Clone 154 and Clone 163 and each comprises the following heavy and light chain amino acid, coding, variable, and CDR sequences (according to Clothia), as provided and labeled:

```
Clone 132 VH DNA Coding Sequence
                                          (SEQ ID NO: 56)
ATGGAGACTGGGCTGCGCTGGCTTCTCCTGGTCGCTGTGCTCAAAGGTGTCCAGTGTCA

GGAGCAGCTGGAGGAGTCCGGGGGAGACCTGGTCCAGCCTGAGGGATCCCTGACACTCA

CCTGCACAGCTTCTGGATTCTCCTTCAGTAGCAGCTACTACATGTGCTGGGTCCGCCAG

GCTCCAGGGAAGGGGCTGGAGTGGATCGCGTGCATTGATGATGGTGGTAGTTATACTTA

CTACGCGAGCTGGGCGAAAGGCCGATTCACCATCTCCAAAACCTCGTCGACCACGGTGA
```

-continued
CTCTGCAAATGACCAGTCTGACAGACGCGGACACGGCCACTTATTTCTGTACGAGACAT

GTTAGGGGTGCTGATTATTATAATTTGTGGGGCCCAGGCACCCTGGTCACCGTCTCCTC

A

Clone 132 VH AA (CDRs underlined)
(SEQ ID NO: 2)
METGLRWLLLVAVLKGVQCQEQLEESGGDLVQPEGSLTLTCTA<u>SGFSFSSSY</u>YMCWVRQA PGKGLEWIACI<u>DDGGS</u>YTYYASWAKGRFTISKTSSTTVTLQMTSLTDADTATYFCTR<u>HVR GADYYNL</u>WGPGTLVTVSS Clone 132 VH CDR1 AA
(SEQ ID NO: 26)
GFSFSSSY Clone 132 VH CDR2 AA
(SEQ ID NO: 27)
DDGGS Clone 132 VH CDR3 AA
(SEQ ID NO: 19)
HVRGADYYNL Clone 132 VL DNA Coding Sequence
(SEQ ID NO: 57)
ATGGACACGAGGGCCCCCACTCAGCTGCTGGGGCTCCTGCTGCTCTGGCTCCCAGGTGC

CACATTTGCCATCGTGATGACCCAGACTCCATCCTCCGTGTCTGCAGCTGTGGGAGGCA

CAGTCACCATCAGTTGCCAGGCCAGTCAGAGTGTTTATAATAACAACCGCTTATCCTGG

TATCAGCAGAAACCAGGGCAGCCTCCCAAGCTCCTGATCTATCTGGCATCCACTCTGGC

ATCTGGGGTCCCATCGCGGTTCAAAGGCAGTGGATCTGGGACACAGTTCACTCTCACCA

TCAGCGACCTGGAGTGTGACGATGCTGCCACTTATTATTGTGCAGGATATCAATATAGT

GAGACTGATGGTTTTGCTTTCGGCGGAGGGACCGAGGTGGTGGTCAAA

Clone 132 VL AA (CDRs underlined)
(SEQ ID NO: 3)
MDTRAPTQLLGLLLLWLPGATFAIVMTQTPSSVSAAVGGTVTISC<u>QASQSVYNNNRLS</u>W YQQKPGQPPKLLIY<u>LASTLAS</u>GVPSRFKGSGSGTQFTLTISDLECDDAATYYC<u>AGYQYS ETDGFA</u>FGGGTEVVVK Clone 132 VL CDR1 AA
(SEQ ID NO: 8)
QASQSVYNNNRLS Clone 132 VL CDR2 AA
(SEQ ID NO: 9)
LASTLAS Clone 132 VL CDR3 AA
(SEQ ID NO: 10)
AGYQYSETDGFA Clone 154 VH DNA Coding Sequence
(SEQ ID NO: 58)
ATGGAGACTGGGCTGCGCTGGCTTCTCCTGGTCGCTGTGCTCAAAGGTGTCCAGTGTCA

GTCGTTGGAGGAGTCCGGGGGAGACCTGGTCAAGCCTGAGGGATCCCTGACACTCACC

TGCACAGCCTCTGGATTCTCCTTCAGTAGCAGCGCCTACATGTGCTGGGTCCGCCAGGC

TCCAGGGAAGGGGCTGGAGTGGATCGCATGCATTTATGGTAGTAATAGTGGTAACACTT

ACTACGCGAACTGGGCGAAAGGCCGATTCACCATCTCCAAAACCTCGTCGACCACGGT

GACTCTGCAGATGACCAGTCTGACAGCCGCGGACACGGCCACCTATTTCTGTGCGAGAT

ATGCTGTCGGTAGTTGGGACTATTTTGACTTGTGGGGCCCAGGCACCCTGGTCACCGCC

TCCTCA

-continued

Clone 154 VH AA (CDRs underlined)
(SEQ ID NO: 4)
METGLRWLLLVAVLKGVQCQSLEESGGDLVKPEGSLTLTCTASGFSFSSSAYMCWVRQAP

GKGLEWIACIYGSNSGNTYYANWAKGRFTISKTSSTTVTLQMTSLTAADTATYFCARYAV

GSWDYFDLWGPGTLVTASS

Clone 154 VH CDR1 AA
(SEQ ID NO: 28)
GFSFSSSA

Clone 154 VH CDR2 AA
(SEQ ID NO: 29)
YGSNSG

Clone 154 VH CDR3 AA
(SEQ ID NO: 22)
YAVGSWDYFDL

Clone 154 VL DNA Coding Sequence
(SEQ ID NO: 59)
ATGGACACGAGGGCCCCCACTCAGCTGCTGGGGCTCCTGCTGCTCTGGCTCCCAGGTGC

CAGATGTGATGTTGTGATGACCCAGACTCCAGCCTCCGTGTCTGAACCTGTGGGAGGCA

CAGTCACCATCAAGTGCCAGGCCAGTCAGAGCATTGGTAGTCATTTAGCCTGGTATCAG

CAGAAACCAGGGCAGCCTCCCAAGCTCCTGATATATGGTGCATCCACTCTGGCATCTGG

GGTCCCATCGCGGTTCAAAGGCAGTGGATCTGGGACACAGTTCACTCTCACCATCAGCG

ACCTGGAGTGTGCCGATGCTGCCACTTACTACTGTCAATGTACTTATGCTGGTGGTTAT

TATGTTTTTGCCTTCGGCGGAGGGACCGAGGTGGTGGTCAAG

Clone 154 VL AA (CDRs underlined)
(SEQ ID NO: 5)
MDTRAPTQLLGLLLLWLPGARCDFVMTQTPASVSEPVGGTVTIKCQASQSIGSHLAWYQQ

KPGQPPKLLIYGASTLASGVPSRFKGSGSGTQFTLTISDLECADAATYYCQCTYAGGYYV

FAFGGGTEVVVK

Clone 154 VL CDR1 AA
(SEQ ID NO: 11)
QASQSIGSHLA

Clone 154 VL CDR2 AA
(SEQ ID NO: 12)
GASTLAS

Clone 154 VL CDR3 AA
(SEQ ID NO: 13)
QCTYAGGYYVFA

Clone 163 VH DNA Coding Sequence
(SEQ ID NO: 60)
ATGGAGACTGGGCTGCGCTGGCTTCTCCTGGTCGCTGTGCTCAAAGGTGTCCAGTGTC

AGCAGCAGCTGGAGGAGTCCGGGGGAGACCTGGTCAAGCCTGAGGGATCCCTGACACT

CACCTGCACAGCTTCTAAATTCTCCTTCAATAAGAAGTATTACATGTGCTGGGTCCGC

CAGGCTCCAGGGAAGGGGCTGGAGTGGATCGGATGTGTTGATACTGGTGATGCTTTCA

TCGGCTACGCGAACTGGGCGAAAGGCCGATTCACCGTCTCCAAAACCTCGTCGACCAC

GGTGGATCTGAAAATGACCAGTCTGACAGCCGCGGACACGGCCACCTATTTCTGTGCG

AGAGGGGTTTATCCTATTAATACTGGTTATTACTACTTTGACTTGTGGGGCCCAGGCA

CCCTGGTCACCGTCTCCTCA

Clone 163 VH AA (CDRs underlined)
(SEQ ID NO: 6)
METGLRWLLLVAVLKGVQCQQQLEESGGDLVKPEGSLTLTCTASKFSFNKKYYMCWVRQ

APGKGLEWIGCVDTGDAFIGYANWAKGRFTVSKTSSTTVDLKMTSLTAADTATYFCARG

VYPINTGYYYFDLWGPGTLVTVSS

```
Clone 163 VH CDR1 AA
                                                       (SEQ ID NO: 30)
KFSFNKKY Clone 163 VH CDR2 AA
                                                       (SEQ ID NO: 31)
DTGDA Clone 163 VH CDR3 AA
                                                       (SEQ ID NO: 25)
GVYPINTGYYYFDL Clone 163 VL DNA Coding Sequence
                                                       (SEQ ID NO: 61)
ATGGACACGAGGGCCCCCACTCAGCTGCTGGGGCTCCTGCTGCTCTGGCTCCCAGGTGC

CAGATGTGCCCTTGTGATGACCCAGACTCCAGCCTCCGTGGAGGCAGCTGTGGGAGGCA

CAGTCACCATCAAGTGCCAGGCCAGTGAGGATATTACTAATTCTTTAGCCTGGTATCAG

CAGAAACCAGGGCAGCCTCCCAACCTCCTGATCTACAGGGCATCCACTCTGGCATCTGG

GGTCTCATCGCGGTTCAAAGGCAGTAGATCTGGGACAGAGTTCACTCTCACCATCAGCG

GCGTGGAGTGTGCCGATGCTGCCACTTACTACTGTCAACAGGGTTATAGTAGTACTAAT

GTTGATAATATTTTCGGCGGAGGGACCGAGGTGGTGGTCAAA

Clone 163 VL AA (CDRs underlined)
                                                       (SEQ ID NO: 7)
MDTRAPTQLLGLLLLWLPGARCALVMTQTPASVEAAVGGTVTIKCQASEDITNSLAWYQQ

KPGQPPNLLIYRASTLASGVSSRFKGSRSGTEFTLTISGVECADAATYYCQQGYSSTNVD

NIFGGGTEVVVK

Clone 163 VL CDR1 AA
                                                       (SEQ ID NO: 14)
QASEDITNSLA Clone 163 VL CDR2 AA
                                                       (SEQ ID NO: 15)
RASTLAS Clone 163 VL CDR3 AA
                                                       (SEQ ID NO: 16)
QQGYSSTNVDNI
```

In one embodiment, the antigen binding molecules of the present disclosure are antibodies and antigen binding fragments thereof. In one embodiment, the antibodies of the present disclosure comprise at least one CDR set forth in FIG. 1A, 1B or 1C. In another aspect, the present disclosure provides hybridomas capable of producing the antibodies disclosed herein and methods of producing antibodies from hybridomas, as described herein and as known in the art.

Humanized antibodies are described herein and may be prepared by known techniques. In one embodiment, a humanized monoclonal antibody comprises the variable domain of a murine or rabbit antibody (or all or part of the antigen binding site thereof) and a constant domain derived from a human antibody. Alternatively, a humanized antibody fragment may comprise an antigen binding site of a murine or rabbit monoclonal antibody and a variable domain fragment (lacking the antigen binding site) derived from a human antibody. Procedures for the production of engineered monoclonal antibodies include those described in Riechmann et al., (1988) Nature 332:323, Liu et al., (1987) Proc. Nat. Acad. Sci. USA 84:3439, Larrick et al., (1989) Bio/Technology 7:934, and Winter et al., (1993) TIPS 14:139. In one embodiment, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557; Padlan et al., (1995) FASEB J. 9:133-39; Tamura et al., (2000) J. Immunol. 164:1432-41; Zhang et al., (2005) Mol. Immunol. 42(12): 1445-1451; Hwang et al., Methods. (2005) 36(1):35-42; Dall'Acqua et al., (2005) Methods 36(1):43-60; and Clark, (2000) Immunology Today 21(8):397-402.

An antigen binding molecule of the present invention may also be a fully human monoclonal antibody. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., (1997) *Curr. Opin. Biotechnol.* 8:455-58).

Examples of techniques for production and use of transgenic animals for the production of human or partially human antibodies are described in U.S. Pat. Nos. 5,814,318, 5,569,825, and 5,545,806; Davis et al., *Antibody Engineering: Methods and Protocols*, (Lo, ed) Humana Press, NJ, 191-200 (2003); Kellermann et al., (2002) *Curr Opin Biotechnol.* 13:593-97; Russel et al., (2000) *Infect Immun.* 68:1820-26; Gallo et al., (2000) *Eur J. Immun.* 30:534-40; Davis et al., (1999) *Cancer Metastasis Rev.* 18:421-25; Green, (1999) *J Immunol Methods* 231:11-23; Jakobovits, (1998) *Advanced Drug Delivery Reviews* 31:33-42; Green et al., (1998) *J Exp Med.* 188:483-95; Jakobovits, (1998) *Exp. Opin. Invest. Drugs.* 7:607-14; Tsuda et al., (1997) *Genomics*, 42:413-21; Mendez et al., (1997) *Nat. Genet.* 15:146-56; Jakobovits, (1994) *Curr Biol.* 4:761-63; Arbones et al., (1994) *Immunity* 1:247-60; Green et al., (1994) *Nat. Genet.* 7:13-21; Jakobovits et al., (1993) *Nature* 362:255-58; Jakobovits et al., (1993) *Proc Natl Acad Sci USA* 90:2551-55; Chen et al., (1993) *Intl Immunol* 5:647-656; Choi et al., (1993) *Nature Genetics* 4:117-23; Fishwild et al., (1996) *Nature Biotechnology* 14:845-51; Lonberg et al., (1994) *Nature* 368: 856-59; Lonberg, (1994) *Handbook of Experimental Pharmacology* 113: 49-101; Neuberger, (1996) *Nature Biotech* 14:826; Taylor et al., (1992) *Nucleic Acids Research* 20:6287-95; Taylor et al., (1994) *Intl Immunol* 6:579-91; Tomizuka et al., (1997) *Nature Genetics* 16:133-43; Tomizuka et al., (2000) *Proc Nat Acad Sci USA* 97:722-27; Tuaillon et al., (1993) *Proc Nat Acad Sci USA* 90:3720-24; Tuaillon et al., (1994) *J Immunol* 152:2912-20; Lonberg et al., (1994) *Nature* 368:856; Taylor et al., (1994) *Intl Immunol* 6:579; U.S. Pat. No. 5,877,397; Bruggemann et al., (1997) *Curr. Opin. Biotechnol.* 8:455-58; Jakobovits et al., (1995) *Ann. N.Y. Acad. Sci.* 764:525-35.

An additional method for obtaining antigen binding molecules of the invention is by the use of phage display, which is well-established for this purpose. See, e.g., Winter et al., (1994) *Ann. Rev. Immunol.* 12:433-55; Burton et al., (1994) *Adv. Immunol* 57:191-280. Human or murine immunoglobulin variable region gene combinatorial libraries may be created in phage vectors that may be screened to select Ig fragments (Fab, Fv, sFv, or multimers thereof) that bind the scFv FMC63, as well as molecules comprising this sequence and cells presenting such molecules. See, e.g., U.S. Pat. No. 5,223,409; Huse et al., (1989) *Science* 246:1275-81; Sastry et al., (1989) *Proc. Natl. Acad. Sci. USA* 86:5728-32; Alting-Mees et al., (1990) *Strategies in Molecular Biology* 3:1-9; Kang et al., (1991) *Proc. Natl. Acad. Sci. USA* 88:4363-66; Hoogenboom et al., (1992) *J. Mol. Biol.* 227:381-388; Schlebusch et al., (1997) *Hybridoma* 16:47-52 and references cited therein. For example, a library containing a plurality of polynucleotide sequences encoding Ig variable region fragments may be inserted into the genome of a filamentous bacteriophage, such as M13 or lambda phage (λImmunoZap™(H) and λImmunoZap™(L) vectors (Stratagene, La Jolla, Calif) may also be used in this approach) or a variant thereof, in frame with the sequence encoding a phage coat protein.

Briefly, mRNA is isolated from a B-cell population, and used to create heavy and light chain immunoglobulin cDNA expression libraries in the λImmunoZap™(H) and λImmunoZap™(L) and similar vectors. These vectors may be screened individually or co-expressed to form Fab fragments or antibodies. Positive plaques may subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers may be synthesized by one of ordinary skill in the art, or may be purchased from commercial sources, which also sell primers for mouse and human variable regions including, among others, primers for $V_H$, $V_L$, CH and CL regions). These primers may be used to amplify heavy or light chain variable regions, which may then be inserted into vectors. These vectors may then be introduced into *E. coli*, yeast, or mammalian-based systems for expression. Large amounts of a single-chain protein containing a fusion of the $V_H$ and $V_L$ domains may be produced using these methods.

Once cells producing the antigen binding molecules provided herein have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

It will be understood by those of skill in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in, e.g., Harris, (1995) *J Chromatog* 705:129-34).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies may be isolated and purified by a variety of well-established techniques. Such isolation techniques include affinity chromatography with Protein-A Sepharose, size-exclusion chromatography, and ion-exchange chromatography (see, e.g., Baines and Thorpe, (1992) in *Methods in Molecular Biology*, 10:79-104 (The Humana Press). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anti-constant region (light chain or heavy chain) antibody, and an anti-idiotype antibody.

Although the disclosed antigen binding molecules were produced in a rabbit system, human, partially human, or humanized antibodies may be suitable for many applications, particularly those involving administration of the antibody to a human subject, other types of antigen binding molecules will be suitable for certain applications. Such antibodies may be prepared as described herein and form an aspect of the instant disclosure.

The instant disclosure provides antigen binding molecules that specifically bind to GGGGS (SEQ ID NO: 46) and subsequences thereof, particularly GGGS (SEQ ID NO: 1), molecules comprising this sequence and cells presenting such molecules. Antigen binding molecules that cross compete with the antigen binding molecules disclosed herein form another aspect of the instant disclosure.

In certain embodiments, the antigen binding molecule cross competes with a reference antigen binding molecule comprising a one or more CDRs provided in FIG. 1A, 1B or 1C. In some embodiments, the antibody or antigen binding molecule that specifically binds SEQ ID NOs: 1, and/or 46 binds the same or an overlapping epitope as a reference antigen binding molecule disclosed herein (e.g., those comprising sequences presented in FIGS. 1A-C). In certain embodiments, the antibody or antigen binding molecule binds the same or an overlapping epitope as a reference antibody.

IIa. Clone 132

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR1 comprising, consisting of, or consisting essentially of the amino acid sequence GFSFSSSY (SEQ ID NO: 26).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR2 comprising, consisting of, or consisting essentially of the amino acid sequence DDGGS (SEQ ID NO: 27).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR3 comprising, consisting of, or consisting essentially of the amino acid sequence HVRGADYYNL (SEQ ID NO: 19).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a heavy chain VH comprising: (a) a VH CDR1 comprising, consisting of, or consisting essentially of the amino acid sequence; and/or (b) a VH CDR2 comprising, consisting of, or consisting essentially of the amino acid sequence); and/or (c) a VH CDR3 comprising, consisting of, or consisting essentially of the amino acid sequence In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 1A-C.

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a heavy chain variable region sequence comprising an amino acid sequence of (SEQ ID NO: 2).

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:2.

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VL CDR1 comprising, consisting of, or consisting essentially of the amino acid sequence QASQSVYNNNRLS (SEQ ID NO: 8).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VL CDR2 comprising, consisting of, or consisting essentially of the amino acid sequence LASTLAS (SEQ ID NO: 9).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a VL CDR3 comprising, consisting of, or consisting essentially of the amino acid sequence AGYQYSETDGFA (SEQ ID NO: 10).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a light chain VL comprising: (a) a VL CDR1 comprising, consisting of, or consisting essentially of the amino acid sequence QASQSVYNNNRLS (SEQ ID NO: 8); and/or (b) a VL CDR2 comprising, consisting of, or consisting essentially of the amino acid sequence LASTLAS (SEQ ID NO: 9); and/or (c) a VL CDR3 comprising, consisting of, or consisting essentially of the amino acid sequence AGYQYSETDGFA (SEQ ID NO: 10).

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a light chain variable region sequence comprising an amino acid sequence of SEQ ID NO: 3.

In various embodiments, the light chain variable region is 80%, 85%, 90%, 91%, 92%, 93%, 94%, 95%, 96%, 97%, 98% or 99% identical to the light chain variable region sequence of SEQ ID NO: 3.

In some embodiments, the antibody or antigen binding molecule that specifically binds to the GGGGS (SEQ ID NO: 46) and subsequences thereof, particularly GGGS (SEQ ID NO: 1), molecules comprising this sequence and cells presenting such molecules, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule that specifically binds to the GGGGS (SEQ ID NO: 46) and subsequences thereof, particularly GGGS (SEQ ID NO: 1), molecules comprising this sequence and cells presenting such molecules, comprises: (a) VH CDR1 region comprising the amino acid sequence of SEQ ID NO: 26; (b) a VH CDR2 region comprising the amino acid sequence of SEQ ID NO: 27; (c) a VH CDR3 region comprising the amino acid sequence of SEQ ID NO: 19; (d) a VL CDR1 region comprising the amino acid sequence of SEQ ID NO: 8; (e) a VL CDR2 region comprising the amino acid sequence of SEQ ID NO: 9; and (f) a VL CDR3 region comprising the amino acid sequence of SEQ ID NO: 10.

In one embodiment, the antibody or antigen binding molecule comprises: (a) a heavy chain variable region comprising the amino acid sequence of SEQ ID NO: 2; and (b) a light chain variable region comprising the amino acid sequence of SEQ ID NO: 3. Nucleotide sequences encoding the heavy chain variable region and the light chain variable region are SEQ ID NO: 56 and SEQ ID NO: 57, respectively.

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 2; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 3.

IIb. Clone 154

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR1 comprising, consisting of, or consisting essentially of the amino acid sequence GFSFSSSA (SEQ ID NO: 28).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR2 comprising, consisting of, or consisting essentially of the amino acid sequence YGSNSG (SEQ ID NO: 29).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR3 comprising, consisting of, or consisting essentially of the amino acid sequence YAVGSWDYFDL (SEQ ID NO: 22).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a heavy chain VH comprising: (a) a VH CDR1 comprising, consisting of, or consisting essentially of the amino acid sequence SEQ ID NO: 28; and/or (b) a VH CDR2 comprising, consisting of, or consisting essentially of the amino acid sequence SEQ ID NO: 29; and/or (c) a VH CDR3 comprising, consisting of, or consisting essentially of the amino acid sequence SEQ ID NO: 22

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 1A-C.

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a heavy chain variable region sequence comprising an amino acid sequence of (SEQ ID NO: 4).

In various embodiments, the heavy chain variable region is 80%, 85%, 90%, 91%, 92%, 93%, 94%, 95%, 96%, 97%, 98% or 99% identical to the heavy chain variable region sequence of SEQ ID NO: 4.

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VL CDR1 comprising, consisting of, or consisting essentially of the amino acid sequence QASQSIGSHLA (SEQ ID NO: 11)

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VL CDR2 comprising, consisting of, or consisting essentially of the amino acid sequence GASTLAS (SEQ ID NO: 12).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a VL CDR3 comprising, consisting of, or consisting essentially of the amino acid sequence QCTYAGGYYVFA (SEQ ID NO: 13).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a light chain VL comprising: (a) a VL CDR1 comprising, consisting of, or consisting essentially of the amino acid sequence QASQSIGSHLA (SEQ ID NO: 11); and/or (b) a VL CDR2 comprising, consisting of, or consisting essentially of the amino acid sequence GASTLAS (SEQ ID NO: 12); and/or (c) a VL CDR3 comprising, consisting of, or consisting essentially of the amino acid sequence QCTYAGGYYVFA (SEQ ID NO: 13).

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a light chain variable region sequence comprising an amino acid sequence of SEQ ID NO: 5.

In various embodiments, the light chain variable region is 80%, 85%, 90%, 91%, 92%, 93%, 94%, 95%, 96%, 97%, 98% or 99% identical to the light chain variable region sequence of SEQ ID NO: 5.

In some embodiments, the antibody or antigen binding molecule that specifically binds to the GGGGS (SEQ ID NO: 46) and subsequences thereof, particularly GGGS (SEQ ID NO: 1), molecules comprising this sequence and cells presenting such molecules, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule that specifically binds to the GGGGS (SEQ ID NO: 46) and subsequences thereof, particularly GGGS (SEQ ID NO: 1), molecules comprising this sequence and cells presenting such molecules, comprises: (a) a VH CDR1 region comprising the amino acid sequence of SEQ ID NO: 28; (b) a VH CDR2 region comprising the amino acid sequence of SEQ ID NO: 29; (c) a VH CDR3 region comprising the amino acid sequence of SEQ ID NO: 22; (d) a VL CDR1 region comprising the amino acid sequence of SEQ ID NO: 11; (e) a VL CDR2 region comprising the amino acid sequence of SEQ ID NO: 12; and (f) a VL CDR3 region comprising the amino acid sequence of SEQ ID NO: 13.

In one embodiment, the antibody or antigen binding molecule comprises: (a) a heavy chain variable region comprising the amino acid sequence of SEQ ID NO: 4; and (b) a light chain variable region comprising the amino acid sequence of SEQ ID NO: 5. Nucleotide sequences encoding the heavy chain variable region and the light chain variable region are SEQ ID NO: 58 and SEQ ID NO: 59, respectively.

In one embodiment, the antibody or antigen binding molecule comprises: (a) a heavy chain comprising the amino acid sequence of SEQ ID NO: 4; and (b) a light chain comprising the amino acid sequence of SEQ ID NO: 5.

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 4; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 5.

IIb. Clone 163

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR1 comprising, consisting of, or consisting essentially of the amino acid sequence KFSFNKKY (SEQ ID NO: 30).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR2 comprising, consisting of, or consisting essentially of the amino acid sequence DTGDA (SEQ ID NO: 31).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VH CDR3 comprising, consisting of, or consisting essentially of the amino acid sequence GVYPINTGYYYFDL (SEQ ID NO: 25).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a heavy chain VH comprising: (a) a VH CDR1 comprising, consisting of, or consisting essentially of the amino acid sequence KFSFNKKY (SEQ ID NO: 30); and/or (b) a VH CDR2 comprising, consisting of, or consisting essentially of the amino acid sequence DTGDA (SEQ ID NO: 31); and/or (c) a VH CDR3 comprising, consisting of, or consisting essentially of the amino acid sequence GVYPINTGYYYFDL (SEQ ID NO: 25).

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a VH CDR1, a VH CDR2, and VH CDR3, wherein the VH CDR1, VH CDR2, and VH CDR3 comprise the amino acid sequence of the VH CDR1, VH CDR2, and VH CDR3 sequences presented in FIGS. 1A-C.

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a heavy chain variable region sequence comprising an amino acid sequence of (SEQ ID NO: 6).

In various embodiments, the heavy chain variable region is 80%, 85%, 90%, 91%, 92%, 93%, 94%, 95%, 96%, 97%, 98% or 99% identical to the heavy chain variable region sequence of SEQ ID NO:6.

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VL CDR1 comprising, consisting of, or consisting essentially of the amino acid sequence QASEDITNSLA (SEQ ID NO: 14).

In some embodiments, an antigen binding molecule or antibody that specifically binds to GGGGS (SEQ ID NO: 46) and subsequences thereof, particularly GGGS (SEQ ID NO: 1), molecules comprising this sequence and cells presenting such molecules, comprises a VL CDR2 comprising, consisting of, or consisting essentially of the amino acid sequence RASTLAS (SEQ ID NO: 15).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a VL CDR3 comprising, consisting of, or consisting essentially of the amino acid sequence QQGYSSTNVDNI (SEQ ID NO: 16).

In some embodiments, an antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a light chain VL comprising: (a) a VL CDR1 comprising, consisting of, or consisting essentially of the amino acid sequence QASEDITNSLA (SEQ ID NO: 14); and/or (b) a VL CDR2 comprising, consisting of, or consisting essentially of the amino acid sequence RASTLAS (SEQ ID NO: 15); and/or (c) a VL CDR3 comprising, consisting of, or consisting essentially of the amino acid sequence QQGYSSTNVDNI (SEQ ID NO: 16).

In some embodiments, the antigen binding molecule or antibody that specifically binds to the GGGGS (SEQ ID NO: 46) and subsequences thereof, particularly GGGS (SEQ ID NO: 1), molecules comprising this sequence and cells presenting such molecules, comprises a light chain variable region sequence comprising an amino acid sequence of SEQ ID NO: 7.

In various embodiments, the light chain variable region is 80%, 85%, 90%, 91%, 92%, 93%, 94%, 95%, 96%, 97%, 98% or 99% identical to the light chain variable region sequence of SEQ ID NO: 7.

In some embodiments, the antibody or antigen binding molecule that specifically binds to the GGGGS (SEQ ID NO: 46) and subsequences thereof, particularly GGGS (SEQ ID NO: 1), molecules comprising this sequence and cells presenting such molecules, comprises any one, two, and/or three VH CDR sequences disclosed herein. In certain embodiments, the antibody or antigen binding molecule comprises a VH CDR1, a VH CDR2, and a VH CDR3 having the amino acid sequence of any VH CDR1, VH CDR2, and VH CDR3 disclosed herein, respectively. In some embodiments, the antibody or antigen binding molecule comprises any one, two, and/or three VL CDR sequences disclosed herein. In certain embodiments, the antibody or antigen binding molecule comprises a VL CDR1, a VL CDR2, and a VL CDR3 having the amino acid sequence of any VL CDR1, VL CDR2, and VL CDR3 disclosed herein, respectively.

In one embodiment, the antibody or antigen binding molecule that specifically binds to the GGGGS (SEQ ID NO: 46) and subsequences thereof, particularly GGGS (SEQ ID NO: 1), molecules comprising this sequence and cells presenting such molecules, comprises: (a) a VH CDR1 region comprising the amino acid sequence of SEQ ID NO: 30; (b) a VH CDR2 region comprising the amino acid sequence of SEQ ID NO: 31; (c) a VH CDR3 region comprising the amino acid sequence of SEQ ID NO: 25; (d) a VL CDR1 region comprising the amino acid sequence of SEQ ID NO: 14; (e) a VL CDR2 region comprising the amino acid sequence of SEQ ID NO: 15; and (f) a VL CDR3 region comprising the amino acid sequence of SEQ ID NO: 16.

In one embodiment, the antibody or antigen binding molecule comprises: (a) a heavy chain variable region comprising the amino acid sequence of SEQ ID NO: 6; and (b) a light chain variable region comprising the amino acid sequence of SEQ ID NO: 7. Nucleotide sequences encoding the heavy chain variable region and the light chain variable region are SEQ ID NO: 60 and SEQ ID NO: 61, respectively.

In one embodiment, the antibody or antigen binding molecule comprises: (a) a heavy chain comprising the amino acid sequence of SEQ ID NO: 6; and (b) a light chain comprising the amino acid sequence of SEQ ID NO: 7.

In one embodiment, the antibody or antigen binding molecule comprises: (a) a heavy chain comprising an amino acid sequence that is 80%, 85%, 90%, 91%, 92%, 93%, 94%, 95%, 96%, 97%, 98% or 99% identical to the amino acid sequence of SEQ ID NO: 6; and (b) a light chain comprising an amino acid sequence that is 80%, 85%, 90%, 91%, 92%, 93%, 94%, 95%, 96%, 97%, 98% or 99% identical to the amino acid sequence of SEQ ID NO: 7.

IV. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding an antibody or antigen binding molecule that specifically bind to GGGGS (SEQ ID NO: 46) and/or GGGS (SEQ ID NO: 1), and molecules comprising these sequences and cells presenting such molecules, as described herein.

Any vector known in the art may be suitable for expressing the antibodies and antigen binding molecules of the present invention. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In other aspects, provided herein are cells comprising a polynucleotide or a vector of the present invention. In some embodiments, the present invention is directed to cells, in vitro cells, comprising a polynucleotide encoding an antigen binding molecule, as described herein. In some embodiments, the present invention is directed to cells, e.g., in vitro cells, comprising a polynucleotide encoding an antibody or an antigen binding molecule thereof that specifically binds to GGGGS (SEQ ID NO: 46) and/or GGGS (SEQ ID NO: 1), molecules comprising these sequences and cells presenting such molecules, as disclosed herein.

Any cell may be used as a host cell for the polynucleotides and vectors encoding all or a fragment of the antibodies and antigen binding molecules of the present invention. In some embodiments, a host cell may be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, *Enterobacteriaceae* such as *Escherichia*, e.g., *E. coli*; *Bacilli* such as *B. subtilis* and *B. licheniformis*; *Pseudomonas* such as *P. aeruginosa*; and *Streptomyces*. In some embodiments, a host cell is a mammalian cell, such as a human cell. In some embodiments, a host cell is a CHO cell and in other embodiments, a host cell is a sP2/0 or other murine cell. A host cell of the present invention may be obtained through any source known in the art.

Other aspects of the present invention are directed to compositions comprising a polynucleotide described herein, a vector described herein, an antibody an antigen binding molecule described herein, and/or an in vitro cell described herein. In some embodiments, the composition comprises a pharmaceutically acceptable carrier, diluent, solubilizer, emulsifier, preservative and/or adjuvant. In some embodiments, the composition comprises an excipient.

In one embodiment, the composition comprises a polynucleotide encoding an antibody or antigen binding molecule that specifically binds to that specifically binds to GGGGS (SEQ ID NO: 46) and/or GGGS (SEQ ID NO: 1), and molecules comprising these sequences and cells presenting such molecules. In another embodiment, the composition comprises an antigen binding molecule that specifically binds to SEQ ID NOs: 1 and/or 46, and molecules comprising these sequences and cells presenting such molecules. In another embodiment, the composition comprises an in vitro cell comprising a polynucleotide encoding an antibody or an antigen binding molecule thereof encoded by a polynucleotide disclosed herein.

In some embodiments, the composition comprises more than one different antibody or antigen binding molecule that specifically binds to GGGGS (SEQ ID NO: 46) and/or GGGS (SEQ ID NO: 1), and molecules comprising these sequences and cells presenting such molecules. In some embodiments, the composition includes more than one antibody or antigen binding molecule that specifically binds to SEQ ID NOs: 1 and/or 46, and molecules comprising these sequences and cells presenting such molecules, wherein the antibodies or antigen binding molecules bind more than one epitope. In some embodiments, the antibodies or antigen binding molecules will not compete with one another for binding to that epitope. In some embodiments, two or more of the antibodies or antigen binding molecules provided herein are combined together in a pharmaceutical composition. Preferably such a composition will be suitable for administration to a subject, including a human.

V. Exemplary Methods

The following section describes various exemplary methods of using the disclosed antigen binding molecules herein. Any of the antigen binding molecules, and fragments thereof, disclosed herein (including those provided by the Figures and the attached Sequence Listing) may be employed in the disclosed methods.

In some of the disclosed methods T cells may be employed. Such T cells may come from any source known in the art. For example, T cells may be differentiated in vitro from a hematopoietic stem cell population, or T cells may be obtained from a subject. T cells may be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells may be derived from one or more T cell lines available in the art. T cells may also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

In view of the above description of antigen binding molecules that may be employed in the disclosed methods, representative methods will now be discussed in more detail.

Va. Method of Administering a Dose of a Medicament to a Subject

In one aspect, a method of administering a dose of a medicament to a subject, the dose comprising a preselected number of cells presenting a therapeutic molecule comprising an amino acid sequence selected from the group consisting of GGGGS (SEQ ID NO: 46), and GGGS (SEQ ID NO: 1) is provided.

In specific embodiments, the dose comprises $0.5 \times 10^6$ cells per kilogram of the subject, $1.0 \times 10^6$ cells per kilogram of the subject, $2.0 \times 10^6$ cells per kilogram of the subject, $3.0 \times 10^6$ cells per kilogram of the subject, $4.0 \times 10^6$ cells per kilogram of the subject, or $5.0 \times 10^6$ cells per kilogram of the subject, although the method may be employed using any dose. $1.0 \times 10^6$ cells per kilogram of the subject is a preferred dose.

Consistent with the definition provided herein, in various embodiments, a subject is a human or non-human subject. When the subject is a human, the subject may be, e.g., any human who is being treated for an abnormal physiological condition, such as cancer or has been formally diagnosed with a disorder, those without formally recognized disorders, those receiving medical attention, those at risk of developing the disorders, those being studied for the presence or absence of a disorder, etc.

Initially, a sample comprising a population comprising a known number of cells, the population known or suspected to be expressing a therapeutic molecule comprising an amino acid sequence selected from the group consisting of GGGGS (SEQ ID NO: 46), and GGGS (SEQ ID NO: 1), is provided.

In one embodiment, the selected amino acid sequence comprises GGGGS (SEQ ID NO: 46); in another embodiment, the selected amino acide sequence comprises and GGGS (SEQ ID NO: 1).

Consistent with the definition provided herein, in various embodiments, a subject is a human or non-human subject. When the subject is a human, the subject may be, e.g., any human who is being treated for an abnormal physiological condition, such as cancer or has been formally diagnosed with a disorder, those without formally recognized disorders, those receiving medical attention, those at risk of developing the disorders, those being studied for the presence or absence of a disorder, etc.

Initially, a sample of known volume comprising a population comprising a known number of cells, which cells are known or suspected to be presenting a molecule comprising the selected amino acid sequence (i.e., SEQ ID Nos: 1 or 46) is provided. The number of cells may be determined using any known method. In preferred embodiments, the population is determined by counting the cells in the sample using an automated apparatus, such as a cell sorter (e.g., a FACS), however traditional non-automated cell counting methods may also be employed.

The cells of the method may comprise any type of cell, with immune cells (e.g., B lymphocytes, monocytes, dendritic cells, Langerhans cells, keratinocytes, endothelial cells, astrocytes, fibroblasts, and oligodendrocytes) being preferred. T cells (including T cytotoxic, T helper and Treg cells) are especially preferred. In specific embodiments, the cells are T cells, which may be obtained as described herein and by methods known in the art. Any type of cell may be employed in the method, and the cell may be a human or non-human cell (including both prokaryotic and eukaryotic cells). Exemplary cells include, but are not limited to immune cells such as T cells, tumor infiltrating lymphocytes (TILs), NK cells, TCR-expressing cells, dendritic cells, and NK-T cells. A T cell may be autologous, allogeneic, or heterologous, or it may be an in vivo T cell or an in vitro T cell, and may be a CD4+ T cell or a CD8+ T cell. In additional embodiments, the cells are T cells presenting a CAR. Moreover, the cells may be disposed in, or isolated from, any environment capable of maintaining the cells in a viable form, such as blood, tissue or any other sample obtained from a subject, cell culture media, tissue grown ex vivo, etc. Gradient purification, cell culture selection and/or cell sorting may be useful in obtaining cells.

The therapeutic molecule expressed by the cell may comprise any molecule known or suspected to provide a therapeutic benefit to a subject to which is it administered. Thus, a therapeutic molecule may be a peptide or polypeptide of any structure or design. Preferably the portion of the therapeutic molecule comprising the selected amino acid sequence (i.e., SEQ ID NO: 1 or 46) is expressed or disposed, at least in part, extracellularly, i.e., to a degree that it may be recognized by an extracellular interaction partner such as the antigen binding molecules of the instant disclosure.

In specific embodiments, the therapeutic molecule is a CAR. When the therapeutic molecule is a CAR it may comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29

(ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

Continuing, an aliquot of the sample comprising a population of cells presenting a molecule comprising the selected amino acid sequence is provided. The aliquot may be obtained using any convenient means, such as by a cell sorter, by a simply pipetting of material out of the sample, etc.

Further, an antigen binding molecule that specifically binds the selected amino acid sequence and comprises a detectable label is provided. The antigen binding molecule is preferably an antigen binding molecule disclosed herein, e.g., in the Figures, Sequence Listing or the instant disclosure. Any detectable label may be employed in the method, and suitable labels may be selected using a desired set of criteria. Examples of types of detectable labels include a fluorescent dye, which may be selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. Other types of detectable labels include optical dyes, which are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I) photochromic compounds, magnetic labels (e.g., DYNABEADS), etc. Strategies for the labeling of proteins are known in the art and may be employed in the disclosed method.

The label may be associated with the antigen binding molecule at any position in the molecule, although it is preferable to associate the label with the molecule at a position (or positions, if multiple labels are employed) at a point such that the binding properties of the molecule are not modified, unless such modified binding activity is desired. Any antigen binding molecule that specifically binds the selected amino acid sequence (i.e., SEQ ID NO: 1 or 46) may be employed. Examples of suitable antigen binding molecules and components thereof are provided herein, e.g., an isolated antigen binding molecule that specifically binds to a polypeptide comprising the amino acid sequence GGGS (SEQ ID NO: 1) or GGGGS (SEQ ID NO: 46).

The antigen binding molecule may be disposed on any surface, or no surface at all. For example, the antigen binding molecule may be present in a buffer and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

Continuing, the aliquot of the sample is contacted with the antigen binding molecule under conditions that permit the formation of a binding complex comprising a cell present in the sample and the antigen binding molecule. Thus, the result of this step of the method is the formation of a binding complex in which the antigen binding molecule, with which a detectable label is associated, is bound to the cell expressing the therapeutic molecule, which comprises the selected amino acid sequence (i.e., SEQ ID NO: 1 or 46). Thus, the binding complex itself is detectable. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

The fraction of cells present in a binding complex with the antigen binding molecule in the aliquot is determined. This calculation may be performed by comparing the number of cells bearing the detectable label to those that do not, and may be represented as percentage. The number of cells in binding complexes may be determined. The specific method employed to determine the number of cells present in a binding complex will be dependent on the nature of the label selected. For example, FACS may be employed when a fluorescent label is selected; when an isotope label is selected mass spectrometry, NMR or other technique may be employed; magnetic-based cell sorting may be employed when a magnetic label is chosen; microscopy may also be employed. The number of cells in the sample is known ab initio and thus the fraction of cells present in a binding complex may be easily determined.

Continuing, the concentration of cells in the initial sample expressing a molecule comprising the selected amino acid sequence (i.e., SEQ ID NO: 1 or 46) is determined; the determination is based on the fraction of cells determined to be present in the binding complex, and thus expressing the therapeutic protein bearing a detectable label.

The fraction of cells presenting the therapeutic protein is known, and the volume of the aliquot is known; thus a simple comparison of the number of cells in the sample from which the aliquot was taken that are expressing the therapeutic molecule to the volume of the larger sample provides the fraction of the cells in the sample bearing the therapeutic molecule on a therapeutic molecule/volume basis (i.e., the concentration of cells bearing the therapeutic molecule in the larger sample).

The volume of the sample that comprises the selected number of cells is determined, by extrapolation based on the concentration of cells bearing therapeutic molecule present in the sample.

Finally, the volume of sample comprising the desired number of cells is administered to the subject. The administration may comprise an aspect of a therapeutic regimen based on the therapeutic molecule present in the sample and expressed by the cells in the sample.

Although the administration may be performed one time or more than one time, an advantage of the method is that by administering a dose comprising the preselected number of cells, which number of cells will be determined based on a known or expected efficacy, unnecessary administration of cells presenting the therapeutic molecule is avoided; i.e., the subject receives the correct number of cells to provide a desired therapeutic benefit and is not too many or too few cells.

Vb. Method of Activating Cells

The disclosed methods of activating an immune cell may be employed in connection with any immune cell presenting a molecule comprising a sequence selected from the group consisting of GGGGS (SEQ ID NO: 46) and GGGS (SEQ ID NO: 1). In the context of the disclosed methods, T cells (including T cytotoxic, T helper and Treg cells) presenting such molecules are preferred and will be used to exemplify the disclosed methods, however other immune cells presenting such molecules (e.g., lymphocytes such as tumor infiltrating lymphocytes (TILs), cytotoxic T lymphocytes, tumor infiltrating lymphocytes, neutrophils, basophils, or T helper cells, Treg cells, dendritic cells, B cells, hematopoietic stem cells, macrophages, monocytes, Langerhans cells, keratinocytes, endothelial cells, astrocytes, fibroblasts, and oligodendrocytes and NK cells) may also be employed in the disclosed methods.

Activation (which term is used interchangeably with the term "stimulation") of T cells is dependent upon signals transferred through antigen-specific T cells receptor recognition and accessory receptors on the T cell. For example, clustering of CD3gamma, CD3delta, CD3epsilon and CD3zeta proteins, further associate with other components of the T cell Receptor (TCR), induces activation of the T cell and makes it immunocompetent. Thus, "activation" or "stimulation" as used herein, refers to a primary response induced by binding of a molecule with a ligand (which may be another copy of the same molecule, e.g., CD3zeta associating with another copy of CD3zeta), wherein the binding mediates a signal transduction event.

In one embodiment, T cells are activated in vitro by means of an antigen binding molecule provided herein, and the T cells activated in accordance with the methods of the instant disclosure may be subsequently expanded ex vivo and used in a variety of applications, including those disclosed herein.

In another embodiment, activation occurs in vivo, by means of an antigen binding molecule provided herein, and the T cells activated in accordance with the methods of the instant disclosure; expansion occurs within the organism in which the activated cells are disposed. In vivo activation may form a component of a therapeutic regime, examples of which are described herein.

Prior to activation, immune cells, such as T cells, are obtained from a subject (e.g., a mammal such as a human, dog, cat, mouse, rat, rabbit or transgenic species thereof; cells derived from an artificial system such as an artificial thymic organoid (ATO; see, e.g., Seet et al., Nature Methods 14(5):521 (2017), incorporated by reference herein) may also be employed in the disclosed in vivo and in vitro activation methods). Immune cells, including T cells, may be obtained from a number of sources, as described herein, including PBMCs, bone marrow, lymph node tissue, cord blood, thymus tissue, tissue from a site of infection, spleen tissue, tumors or T cell lines. T cells may also be obtained from a volume of blood collected from a subject using any number of techniques known to the skilled artisan, such as FICOLL separation. Gradient purification, cell culture selection and/or cell sorting may also be employed.

In view thereof, a method of activating an immune cell, such as a T cell, presenting a molecule comprising an amino acid sequence selected from the group consisting of GGGGS (SEQ ID NO: 46) and GGGS (SEQ ID NO: 1), is provided.

Initially, a sample comprising an immune cell known or suspected to be presenting a molecule comprising an amino acid sequence selected from the group consisting of GGGGS (SEQ ID NO: 46) and GGGS (SEQ ID NO: 1) is provided. In specific embodiments, the selected amino acid sequence is GGGGS (SEQ ID NO: 46); in other embodiments the selected amino acid sequence is GGGS (SEQ ID NO: 1).

In specific embodiments, the cells are T cells, which may be obtained as described herein and by methods known in the art. The cell may be a human or non-human cell. The T cells may be autologous, allogeneic, or heterologous. When a T cell is employed in the disclosed methods, the T cell may be an in vivo T cell or an in vitro T cell. Moreover, the cells may be disposed in, or isolated from, any environment capable of maintaining the cells in a viable form, such as blood, tissue or any other sample obtained from a subject, cell culture media, tissue grown ex vivo, a suitable buffer, etc.

In specific embodiments, the molecule comprising the selected amino acid sequence (i.e., SEQ ID NO: 1 or 46) is a CAR. When the molecule is a CAR it may comprise a molecule, or fragment thereof, selected from the group consisting of CD2, CD3 delta, CD3 epsilon, CD3 gamma, CD4, CD7, CD8a, CD8, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336

(NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule is then contacted with the sample, under conditions that permit the formation of a binding complex comprising the antigen binding molecule and two molecules comprising the selected amino acid sequence (i.e., SEQ ID NO: 1 or 46), wherein the molecules comprising the selected amino acid sequence are disposed on two different immune cells. The binding event has the effect of bringing both immune cells into closer proximity to one another, with multiple cells being clustered together following multiple binding events. Additionally, the binding event has the effect of clustering receptors on a cell which may be more important for cell signaling.

The antigen binding molecule is preferably an antigen binding molecule (or fragment thereof) disclosed herein, e.g., in the Figures, Sequence Listing or the instant section of the disclosure. Any antigen binding molecule that specifically binds the selected amino acid sequence (i.e., SEQ ID NO: 1 or 46) can be employed. Multiple examples of suitable antigen binding molecules are provided herein, e.g., those having one or more of the CDRs shown in FIGS. 1A-C. The molecules comprising the selected sequences that are present on each immune cell of a binding complex may be the same or they may be different, so long as they are specifically recognized by the antigen binding molecule.

The antigen binding molecule may be disposed on any surface, or no surface at all. For example, in in vivo applications the antigen binding molecule may be present in a buffer and the contacting may be achieved by injecting the antigen binding molecule into the body of a subject, whereupon activation will occur when the antigen binding molecule contacts a cell presenting the molecule comprising the amino acid sequence selected from the group consisting of GGGGS (SEQ ID NO: 46) and GGGS (SEQ ID NO: 1).

The precise amount of antigen binding molecule that will achieve a desired level of activation may be determined empirically, and will depend on various subject-specific criteria. For in vivo activation, the amount of antigen binding molecule may be, for example, 100 µg/kg/day, 75 µg/kg/day, 50 µg/kg/day, 25 µg/kg/day, 20 µg/kg/day, 15 µg/kg/day, 10 µg/kg/day or 5 µg/kg/day. The antigen binding molecule may administered to a subject for a desired number days, for example 5, 4, 3, 2 or 1 day. Other activating antibodies may be used as a guide when determining how much antigen binding molecule to administer to a subject. For example, the clinical experiences with anti-CD3 activating antibody OKT3 may be illustrative and beneficial when performing the disclosed method.

Those of skill in the art will recognize that a specific therapeutic regime may be tailored to a given subject, and dosing amounts and conditions may depend on a variety of factors normally considered by clinicians. Examples that may be considered when determining a suitable dose of antigen binding molecule for an in vivo activation include the overall health and strength of a subject, the subject's weigh, a desired overall degree of activation, the efficacy and in vivo efficacy of the cells presenting the molecule having the selected sequence, In an in vitro activation, the antigen binding molecule may be present in a buffer and the buffer-antigen binding molecule may be contacted with the sample. Alternatively, in some embodiments, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

In practice, when the binding of the antigen binding molecule specifically binds to the molecules comprising the selected amino acid sequence (i.e., SEQ ID NO: 1 or 46), one molecule on each of two different immune cells, the two cells are drawn closer to one another. This close proximity, or clustering, has the effect of activating the immune cells. Additionally, when the binding of the antigen binding molecule specifically binds to the molecules comprising the selected amino acid sequence (i.e., SEQ ID NO: 1 or 46), CAR molecules clustering on the surface of a T cell. This clustering provides both signal 1 and 2 for T-cell stim, since the CARs have CD3z signaling and a costimulating domain. This happens when the Mab or Ag-binding molecules are on beads, or on a plate or other surface.

Vc. Method of Determining a Number of Cells Presenting a Molecule of Interest

There are situations in which it may be desirable to determine the number of cells present in a sample that are expressing a molecule of interest. For example, it may be desirable to determine the number of immune cells present a sample obtained from a subject that are expressing a molecule of interest. Or it may be desirable to determine the number of cells transfected and expressing a molecule of interest, which may be used as a measure of the level of efficiency of the transfection. The disclosed method may be employed in these and other applications in which it is desirable to determine the number of cells present in a sample that are expressing a molecule of interest.

Thus, a method of determining a number of cells presenting a molecule in a sample wherein the molecule comprises an amino acid sequence selected from the group consisting of GGGGS (SEQ ID NO: 46) and GGGS (SEQ ID NO: 1) is provided.

In on embodiment, a sample comprising cells known or suspected to be expressing a molecule of interest comprising an amino acid sequence selected from the group consisting of GGGGS (SEQ ID NO: 46) and GGGS (SEQ ID NO: 1) is provided.

In specific embodiments, the selected amino acid sequence is GGGS (SEQ ID NO: 1); in other embodiments the selected amino acid sequence is GGGGS (SEQ ID NO: 46).

The cell may be of any type, and may be human or non-human (e.g., mouse, rate, rabbit, hamster, etc). In a preferred embodiment, the cell is an immune cell. An immune cell of the method may be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which may be obtained as described herein and by methods known in the art. Any type of immune cell may be employed in this embodiment of the disclosed method. Exemplary cells include, but are not limited to immune cells such as T cells, tumor infiltrating lymphocytes (TILs), NK cells, TCR-expressing cells, dendritic cells, and NK-T cells. The T cells may be autologous, allogeneic, or heterologous. The T cells may be CD4+ T cells or CD8+ T cells. When a T cell is employed in the disclosed methods, the T cell may be an in vivo T cell or an in vitro T cell. Moreover, the cells may be disposed in, or isolated from, any environment capable of maintaining the cells in a viable form, such as blood, tissue or any other sample obtained from a subject, cell culture media, tissue grown ex vivo, a suitable buffer, etc.

In specific embodiments, the molecule of interest is a CAR. When the molecule is a CAR, it may comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

The sample is then contacted with an antigen binding molecule that specifically binds the molecule of interest and comprises a detectable label, under conditions that permit the formation of a binding complex comprising a cell present in the sample and the antigen binding molecule. The antigen binding molecule is preferably an antigen binding molecule (or fragment thereof) disclosed herein, e.g., in the Figures, Sequence Listing or the instant section of the disclosure. Any antigen binding molecule that specifically binds the selected amino acid sequence (i.e., SEQ ID NO: 1 or 46) may be employed in the disclosed method. Multiple examples of suitable antigen binding molecules are provided herein, e.g., those having one or more of the CDRs shown in FIGS. 1A-C.

Any detectable label may be employed in the method, and suitable labels may be selected using a desired set of criteria. Examples of types of detectable labels include a fluorescent dye, which may be selected from the group consisting of an Atto dye, an Alexafluor dye, quantum dots, Hydroxycoumarin, Aminocoumarin, Methoxycoumarin, Cascade Blue, Pacific Blue, Pacific Orange, Lucifer yellow, NBD, R-Phycoerythrin (PE), PE-Cy5 conjugates, PE-Cy7 conjugates, Red 613, PerCP, TruRed, FluorX, Fluorescein, BODIPY-FL, Cy2, Cy3, Cy3B, Cy3.5, Cy5, Cy5.5, Cy7, TRITC, X-Rhodamine, Lissamine Rhodamine B, Texas Red, Allophycocyanin (APC), APC-Cy7 conjugates, Indo-1, Fluo-3, Fluo-4, DCFH, DHR, SNARF, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AmCyan1, mTFP1, GFP (S65A mutation), Midoriishi Cyan, Wild Type GFP, GFP (S65C mutation), TurboGFP, TagGFP, GFP (S65L mutation), Emerald, GFP (S65T mutation), EGFP, Azami Green, ZsGreen1, TagYFP, EYFP, Topaz, Venus, mCitrine, YPet, TurboYFP, ZsYellow1, Kusabira Orange, mOrange, Allophycocyanin (APC), mKO, TurboRFP, tdTomato, TagRFP, DsRed monomer, DsRed2 ("RFP"), mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll (PerCP), mKate (TagFP635), TurboFP635, mPlum, and mRaspberry. Other types of detectable labels include optical dyes, which are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I) photochromic compounds, magnetic labels (e.g., DYNABEADS), etc. Strategies for the labeling of proteins are known in the art and may be employed in the disclosed method.

The label may be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule or fragment thereof that specifically binds the molecule of interest comprising the selected amino acid sequence (i.e., SEQ ID NO: 1 or 46) may be employed in the disclosed method.

The antigen binding molecule may be disposed on any surface, or no surface at all. For example, the antigen binding molecule may be present in a buffer and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method.

Continuing, the number of cells present in a binding complex in the sample is determined. The specific method employed to determine the number of cells present in a binding complex will be dependent on the nature of the label selected. For example, FACS may be employed when a fluorescent label is selected; when an isotope label is selected mass spectrometry, NMR or other technique may be employed; magnetic-based cell sorting may be employed when a magnetic label is chosen; microscopy may also be employed. The output of these detection methods may be in the form of a number of cells or the output may be of a form that allows the calculation of the number of cells based on the output.

Vd. Method of Isolating a Molecule

It is of tremendous value to have the ability to separate populations of different molecules, and particularly biologically-relevant molecules, from one another. Using the antigen binding molecules provided herein, such separation may be achieved and employed in a range of biotechnological, biopharmaceutical and therapeutic applications.

In one aspect of the instant disclosure, a method of isolating a molecule comprising an amino acid sequence selected from the group consisting of GGGGS (SEQ ID NO: 46) and GGGS (SEQ ID NO: 1) is provided.

In one embodiment, the method comprises providing a sample known or suspected to comprise a molecule comprising an amino acid sequence selected from the group consisting of GGGGS (SEQ ID NO: 46) and GGGS (SEQ ID NO: 1).

In specific embodiments, the selected amino acid sequence is GGGS (SEQ ID NO: 1); in other embodiments the selected amino acid sequence is GGGGS (SEQ ID NO: 46).

In specific embodiments, the molecule of interest is a CAR. When the molecule is a CAR it may comprise a molecule, or fragment thereof, selected from the group consisting of CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule that specifically binds the selected amino acid sequence (i.e., SEQ ID NO: 1 and/or 46) and optionally comprises a detectable label is provided. When it is decided to employ a detectable label, any detectable label may be employed in the method, as described herein, and suitable labels may be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques*, 11$^{th}$ Edition, Life Technologies, (2010), hereby expressly incorporated by reference, radiolabels (e.g., isotope markers such as $^{3}$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I). Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus,* or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNA-BEADS), etc may also be employed. Strategies for the labeling of proteins are well known in the art and may be employed in the disclosed method.

The label may be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule, or fragment thereof, that specifically binds the selected amino acid sequence (i.e., SEQ ID NO: 1 or 46) may be employed, such as those disclosed herein, e.g., those having one or more of the CDRs shown in FIGS. 1A-1C.

The antigen binding molecule may be disposed on any surface, or no surface at all. For example, the antigen binding molecule may be present in a buffer and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

The sample is contacted with the antigen binding molecule, under conditions that permit the formation of a binding complex comprising a molecule comprising the selected amino acid sequence and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex may be disposed on surfaces as described herein, formed binding complexes may also be disposed on surfaces.

At this stage, no binding complexes may have formed, or a plurality of binding complexes comprising one or more antigen binding molecules bound to a molecule comprising the selected amino acid sequence (i.e., SEQ ID NO: 1 or 46)

may have formed. Unbound molecules comprising the selected amino acid sequence and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture may be washed away using a solution that leaves formed binding complexes intact. If a binding complex is disposed on a bead, the bead itself may be situated in a column or other structure and the same approach may be used.

The solution used to induce the formation of binding complexes may be used, for example, as a wash solution to remove unbound components. Any suitable buffer or solution that does not disrupt formed binding complexes may be used. Typically, buffers having high salt concentrations, non-physiological pH, containing chaotropes or denaturants, are preferably avoided when performing this step of the method.

A formed binding complex is then separated into (a) a molecule comprising the selected amino acid sequence (i.e., SEQ ID NO: 1 or 46), and (b) an antigen binding molecule. The separation may be achieved using standard methodologies known to those of skill in the art. For example, a solution containing free peptide may be used to separate the antigen binding complex. A solution of suitable pH and composition may be washed over the complexes. A solution that is commonly employed for this purpose is 0.1 M glycine HCl, pH 2.5-3.0, and this solution may be employed to achieve the separation. Other solutions that may be employed include 100 mM citric acid, pH 3.0, 50-100 mM triethylamine or triethanolamine, pH 11.5; 150 mM ammonium hydroxide, pH 10.5; 0.1 M glycine-NaOH, pH 10.0; 5 M lithium chloride, 3.5 M magnesium or potassium chloride, 3.0 M potassium chloride, 2.5 M sodium or potassium iodide, 0.2-3.0 M sodium thiocyanate, 0.1 M Tris-acetate with 2.0 M NaCl, pH 7.7; 2-6 M guanidine HCl, 2-8 M urea, 1.0 M ammonium thiocyanate, 1% sodium deoxycholate 1% SDS; and 10% dioxane 50% ethylene glycol, pH 8-11.5. Any suitable buffer or solution that disrupts formed binding complexes may also be used. Typically, buffers having high salt concentrations, non-physiological pH, containing chaotropes or denaturants, may be used when performing this step of the method.

Following the separation, if the molecule comprising the selected amino acid sequence (i.e., SEQ ID NO: 1 or 46) is of primary interest it may be collected; alternatively, if the antigen binding molecule is of primary interest it may be collected.

Ve. Method of Determining the Presence or Absence of a Molecule

As disclosed herein, it may sometimes be desirable to isolate a molecule comprising an amino acid sequence selected from the group consisting of SEQ ID NO: 1 or 46. In other cases, simply knowing whether a molecule comprising an amino acid sequence selected from the group consisting of SEQ ID NO: 1, or 46, is present or absent from a sample is enough information. For example, it may be beneficial to know that such a molecule is being expressed, regardless of the level of expression. In other cases, it may be desirable to know if a purification process or step designed to remove such a molecule has been effectively. Thus, the qualitative determination of the presence or absence of a molecule comprising an amino acid sequence selected from the group consisting of SEQ ID NO: 1 or 46, may be useful in multiple applications.

In view thereof, a method of determining the presence or absence in a sample of a molecule comprising an amino acid selected from the group consisting of GGGGS (SEQ ID NO: 46) and GGGS (SEQ ID NO: 1), in a sample is provided.

In one embodiment, the method comprises providing a sample known or suspected to comprise a molecule comprising an amino acid sequence selected from the group consisting of GGGGS (SEQ ID NO: 46) and GGGS (SEQ ID NO: 1).

In specific embodiments the selected amino acid sequence is GGGS (SEQ ID NO: 1); and in other embodiments the selected amino acid sequence is GGGGS (SEQ ID NO: 46).

In specific embodiments, the molecule comprising the selected amino acid sequence (i.e., SEQ ID NO: 1 or 46) is a CAR. When the molecule is a CAR it may comprise a molecule, or fragment thereof, selected from the group consisting of CD2, CD3 delta, CD3 epsilon, CD3 gamma, CD4, CD7, CD8a, CD8, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule comprising a detectable label, which antigen binding molecule specifically binds the selected amino acid sequence (i.e., SEQ ID NO: 1 or 46) is provided. Suitable labels may be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes*

Handbook: *A Guide to Fluorescent Probes and Labeling Techniques*, 11th Edition, Life Technologies, (2010), hereby expressly incorporated by reference, radiolabels (e.g., isotope markers such as $^3$H, C, $^{14}$C, $^{15}$N, $^{18}$F, $^{35}$, $^{64}$CU, $^{90}$Y $^{99}$Tc, $^{111}$In, $^{124}$I, $^{125}$I, $^{131}$I) Photochromic compounds, a Halo-tag, Atto dyes, Tracy dyes, proteinaceous fluorescent labels (e.g., proteinaceous fluorescent labels also include, but are not limited to, green fluorescent protein, including a *Renilla*, *Ptilosarcus*, or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc may also be employed. Strategies for the labeling of proteins are well known in the art and may be employed in the disclosed method. The label may be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds a molecule comprising the selected amino acid sequence (i.e., SEQ ID NO: 1 or 46) may be employed, such as those disclosed herein, e.g., those having one or more of the CDRs shown in FIGS. 1A-C.

Continuing, the sample is contacted with the antigen binding molecule under conditions that permit the formation of a binding complex comprising a cell present in the sample and the antigen binding molecule. The antigen binding molecule may be disposed on any surface, or no surface at all. For example, the antigen binding molecule may be present in a buffer and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

The sample is contacted with the antigen binding molecule, under conditions that permit the formation of a binding complex comprising a molecule comprising the molecule comprising the selected amino acid sequence (i.e., SEQ ID NO: 1 or 46) and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex may be disposed on surfaces as described herein, formed binding complexes may also be disposed on surfaces.

At this stage, no binding complexes may have formed, or a plurality of binding complexes comprising one or more antigen binding molecules bound to a molecule comprising the selected amino acid sequence (i.e., SEQ ID NO: 1 or 46) (or one or more molecules comprising the selected amino acid sequence bound to an antigen binding molecule) may have formed. Unbound molecules comprising the selected amino acid sequence (i.e., SEQ ID NO: 1 or 46) and/or unbound antigen binding molecules may also be present in the local environment of any formed binding complexes.

Any molecules not part of a binding complex are then separated from any formed binding complexes. The method of the removal will depend on the structure and/or local environment of the binding complexes. For example, if the antigen binding molecule is disposed on a bead, plate or bag the unbound components of the reaction mixture may be washed away using a solution that leaves formed binding complexes intact. If a binding complex is disposed on a bead, the bead itself may be situated in a column or other structure and the same approach may be used.

In some embodiments, separation of the binding complex is not required for detection.

The solution used to induce the formation of binding complexes may be used, for example, as a wash solution to remove unbound components. Any suitable buffer or solution that does not disrupt formed binding complexes may also be used. Typically, buffers having high salt concentrations, non-physiological pH, containing chaotropes or denaturants, should be avoided when performing this step of the method.

Lastly, the presence or absence of a binding complex—which will comprise a molecule comprising the selected amino acid sequence (i.e., SEQ ID NO: 1 or 46) and an antigen binding molecule—is detected. The specific method employed to detect the presence or absence of a binding complex will be dependent on the nature of the label selected. For example, FACS may be employed when a fluorescent label is selected; when an isotope label is selected mass spectrometry, NMR or other technique may be employed; magnetic-based cell sorting may be employed when a magnetic label is chosen; microscopy may also be employed. The end result of the method is a qualitative assessment of the presence or absence of the antigen binding molecule comprising the detectable label, and thus, the presence or absence of its binding partner, the molecule comprising the selected amino acid sequence (i.e., SEQ ID NO: 1 or 46).

As is the case with all of the disclosed methods, the molecule comprising the selected amino acid sequence (i.e., SEQ ID NO: 1 or 46) may be disposed in any environment. In some embodiments, the molecule comprising the selected amino acid sequence (i.e., SEQ ID NO: 1 or 46) is expressed on the surface of a cell. In this embodiment, the cell may be of any type, and may be human or non-human (e.g., mouse, rate, rabbit, hamster, etc). In a preferred embodiment, the cell is an immune cell. An immune cell of the method may be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which may be obtained as described herein and by methods known in the art. Any type of immune cell may be employed in this embodiment of the disclosed method, and the cell may be a human or non-human cell. Exemplary cells include, but are not limited to immune cells such as T cells, tumor infiltrating lymphocytes (TILs), NK cells, TCR-expressing cells, dendritic cells, and NK-T cells. The T cells may be autologous, allogeneic, or heterologous. In additional embodiments, the cells are T cells presenting a CAR. The T cells may be CD4+ T cells or CD8+ T cells. When a T cell is employed in the disclosed methods, the T cell may be an in vivo T cell or an in vitro T cell.

In additional embodiment, the cell may be disposed in, or isolated from, any environment capable of maintaining the cell in a viable form, such as blood, tissue or any other sample obtained from a subject, cell culture media, tissue grown ex vivo, a suitable buffer, etc.

Vf. Method of Increasing the Concentration of a Molecule

Very often a molecule of interest is present in a sample in lower-than-desired levels. For example, when a cell is transfected with a foreign gene expression levels of the protein(s) encoded by the foreign gene are low. The same may be true for molecules secreted from a cell; such molecules are often present in low quantities (but may still be detected using the methods provided herein, if the molecule comprises one of the disclosed amino acid sequences of SEQ ID NO: 1 or 46). One solution to the problem of low expression levels is to increase the concentration of the molecule of interest, which may be free in solution, or expressed on the surface of a cell. The concentration of intracellularly-expressed molecules of interest may also be enhanced, however the cells must first be lysed to release the molecule.

To address this problem, a method of increasing the concentration of cells presenting a molecule comprising an amino acid sequence selected from the group consisting of GGGGS (SEQ ID NO: 46) and GGGS (SEQ ID NO: 1) is provided.

In one embodiment, the method comprises providing a sample comprising cells known or suspected to comprise a molecule comprising an amino acid sequence selected from the group GGGGS (SEQ ID NO: 46) and GGGS (SEQ ID NO: 1).

In specific embodiments, the selected amino acid sequence is GGGS (SEQ ID NO: 1); and in other embodiments the selected amino acid sequence is GGGGS (SEQ ID NO: 46).

In specific embodiments, the molecule comprising the selected amino acid sequence (i.e., SEQ ID NO: 1 or 46) is a CAR. When the molecule is a CAR it may comprise a molecule, or fragment thereof, selected from the group consisting of CD2, CD3 delta, CD3 epsilon, CD3 gamma, CD4, CD7, CD8a, CD8, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

An antigen binding molecule that specifically binds the selected amino acid sequence (i.e., SEQ ID NO: 1 or 46) and optionally comprises a detectable label is provided. When it is preferable to employ a detectable label, any detectable label may be employed in the method, as described herein, and suitable labels may be selected using a desired set of criteria. Examples of types of detectable labels include fluorescent labels (e.g., fluorescein, rhodamine, tetramethylrhodamine, eosin, erythrosin, coumarin, methyl-coumarins, pyrene, Malachite green, stilbene, Lucifer Yellow, Cascade Blue, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 647, Alexa Fluor 660, Alexa Fluor 680), Cascade Blue, Cas-cade Yellow and R-phycoerythrin (PE) (Molecular Probes), FITC, Rhodamine, and Texas Red (Pierce), Cy5, Cy5.5, Cy7 (Amersham Life Science)). Suitable optical dyes, including fluorophores, are described in Johnson, *Molecular Probes Handbook: A Guide to Fluorescent Probes and Labeling Techniques*, 11th Edition, Life Technologies, (2010), hereby expressly incorporated by reference, radiolabels (e.g., isotope markers such as $^3$H, $^{11}$C, $^{14}$C, $^{15}$N, $^{18}$F, $^{35}$S, $^{64}$CU, $^{90}$Y, $^{99}$Tc, $^{111}$In, $^{124}$I, $^{125}$I, $^{131}$I). Photochromic compounds, a Halo-tag, Atto dyes, Tracy dyes, proteinaceous fluorescent labels (e.g., proteinaceous fluorescent labels also include, but are not limited to, green fluorescent protein, including a *Renilla, Ptilosarcus*, or *Aequorea* species of GFP (Chalfie et al., (1994) *Science* 263:802-805), EGFP (Clon-tech Labs., Inc., Genbank Accession Number U55762), blue fluorescent protein (BFP, Quantum Biotechnologies, Inc; Stauber, (1998) *Biotechniques* 24:462-471; Heim et al., (1996) *Curr. Biol.* 6: 178-182), enhanced yellow fluorescent protein (Clontech Labs., Inc.), luciferase (Ichiki et al., (1993) *J. Immunol.* 150:5408-5417), magnetic labels (e.g., DYNABEADS), etc. may also be employed. Strategies for the labeling of proteins are well known in the art and may be employed in the disclosed method.

The label may be associated with the antigen binding molecule at any position in the molecule, although it is preferable to associate the label with the molecule at a position (or positions, if multiple labels are employed) at a point such that the binding properties of the molecule are not modified (unless such modified binding activity is desired). Any antigen binding molecule that specifically binds the molecule comprising the selected amino acid sequence (i.e., SEQ ID NO: 1 or 46; or one or more molecules comprising the selected amino acid sequence bound to an antigen binding molecule or fragment thereof) may be employed, such as those disclosed herein, e.g., those having one or more of the CDRs shown in FIGS. 1A-C.

The antigen binding molecule may be disposed on any surface, or no surface at all. For example, the antigen binding molecule may be present in a buffer and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

A cell expressing a molecule comprising the selected amino acid sequence (i.e., SEQ ID NO: 1 or 46) may be of any type, and may be human or non-human (e.g., mouse, rate, rabbit, hamster, etc). In a preferred embodiment, the cell is an immune cell. An immune cell of the method may be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which may be obtained as described herein and by methods known in the art. Any type of immune cell may be employed, and the cell may be a human or non-human cell. Exemplary cells include, but are not limited to immune cells such as T cells, tumor infiltrating lymphocytes (TILs), NK cells, TCR-expressing cells, dendritic cells, and NK-T cells. The T cells may be autologous, allogeneic, or heterologous. In additional embodiments, the cells are T cells presenting a CAR. The T cells may be CD4+ T cells or CD8+ T cells. When a T cell is employed in the disclosed methods, the T cell may be an in vivo T cell or an in vitro T cell. Moreover, the cells may be disposed in, or isolated from, any environment capable of maintaining the cells in a viable form, such as blood, tissue or any other sample obtained from a subject, cell culture media, tissue grown ex vivo, a suitable buffer, etc.

The sample comprising cells is contacted with the antigen binding molecule, under conditions that permit the formation of a binding complex comprising a molecule comprising the selected amino acid sequence (i.e., SEQ ID NO: 1 or 46) and the antigen binding molecule. Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex may be disposed on surfaces as described herein, formed binding complexes may also be disposed on surfaces.

At this stage, no binding complexes may have formed, or a plurality of binding complexes comprising one or more antigen binding molecules bound to a molecule comprising the selected amino acid sequence (i.e., SEQ ID NO: 1 or 46) may have formed. Unbound molecules comprising the selected amino acid sequence (i.e., SEQ ID NO: 1 or 46) and/or unbound antigen binding molecules may also be present in the local environment of any formed binding complexes.

Any molecules or cells not part of a binding complex are then separated from any formed binding complexes. The method of the removal will depend on the structure and/or local environment of the binding complexes. For example, if the antigen binding molecule is disposed on a bead, plate or bag the unbound components of the reaction mixture may be washed away using a solution that leaves formed binding complexes intact. If a binding complex is disposed on a bead, the bead itself may be situated in a column or other structure and the same approach may be used.

The solution used to induce the formation of binding complexes may be used, for example, as a wash solution to remove unbound components. Any suitable buffer or solution that does not disrupt formed binding complexes may also be used. Typically, buffers having high salt concentrations, non-physiological pH, containing chaotropes or denaturants, should be avoided when performing this step of the method.

At this stage of the method, a population of cells presenting a molecule comprising the selected amino acid sequence (i.e., SEQ ID NO: 1 or 46) will be present. If a detectable label was employed, the concentration of the cells may be easily determined, consistent with the nature of the label. Cells not expressing the molecule comprising the selected amino acid sequence (i.e., SEQ ID NO: 1 or 46) will be absent, and thus the population (or concentration) of cells presenting a molecule comprising the selected amino acid sequence (i.e., SEQ ID NO: 1 or 46) will be increased compared to the levels prior to performing the method.

If the concentration of the molecule comprising the selected amino acid sequence (i.e., SEQ ID NO: 1 or 46) is not at a desired level, the above steps may be repeated a desired number of times. In the context of this step of the method, a desired number of times may also be zero, if the desired concentration of cells is already present.

Vg. Method of Depleting a Population of Immune Cells

When a subject has an immune cell-mediated condition, it may be of significant importance that the condition be controlled in a timely fashion so as to prevent harm to the subject. For example, when a subject has an autoimmune reaction it may be desirable to suppress an immune cell-mediated response by depleting a population of immune cells, in an effort to prevent harm. In another example, a subject receiving immunotherapy may react too strongly to the therapy and be at risk of harm; depleting the population of immune cells administered to the subject may be an effective approach to mitigating the subject's reaction to the immunotherapy. In view of the need for a method of controlling a subject's immune cell-mediated response, a method of depleting a population of immune cells presenting a molecule comprising an amino acid sequence selected from the group consisting of GGGGS (SEQ ID NO: 46) and GGGS (SEQ ID NO: 1) is provided, such as those provided herein, e.g., those having one or more of the CDRs shown in FIGS. 1A-C, may be employed in the disclosed method.

In one embodiment, the method comprises providing a population of immune cells to be depleted, wherein the cells are known or suspected to be presenting a molecule comprising an amino acid sequence selected from the group consisting of GGGS (SEQ ID NO: 1), and GGGGS (SEQ ID NO: 46).

In specific embodiments, the selected amino acid sequence is GGGS (SEQ ID NO: 1); and in other embodiments the selected amino acid sequence is GGGGS (SEQ ID NO: 46).

In specific embodiments, the molecule comprising the selected amino acid sequence (i.e., SEQ ID NO: 1 or 46) is a CAR. When the molecule is a CAR it may comprise a molecule, or fragment thereof, selected from the group consisting of CD2, CD3 delta, CD3 epsilon, CD3 gamma, CD4, CD7, CD8a, CD8, CD11a (ITGAL), CD11b (ITGAM), CD11c (ITGAX), CD11d (ITGAD), CD18 (ITGB2), CD19 (B4), CD27 (TNFRSF7), CD28, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353

(SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, a Toll-like receptor, and combinations thereof.

In some embodiments, it may be beneficial to kill cells expressing a molecule, such as a CAR. As described above, in some embodiments, a therapeutic cell, such as a CAR T-cell may be used therapeutically and, subsequently, need to be depleted in a patient. In one embodiment, the present invention provides a method of removing these CAR-expressing T-cells using other T-cells. A cell presenting a molecule comprising a specific epitope recognized by a specific antigen binding molecule, such as those disclosed herein (i.e. anti-linker Clone 132, 154 and/or 163, and fragments thereof) may be killed using a diabody, a bispecific molecule comprising a human CD3-binding scFv linked to a specific antigen-binding scFv, such as those composed of fragments of Clone 132, 154, and/or 163, as described herein). In certain embodiments, the diabody binds to a cell expressing a molecule comprising GGGS (SEQ ID NO: 1) or GGGGS (SEQ ID NO 46) and to a human T-cell to form an immunological synapse and facilitate cell death.

An immune cell presenting a molecule comprising the selected amino acid sequence (i.e., SEQ ID NO: 1 or 46) may be of any type, and may be human or non-human (e.g., mouse, rate, rabbit, hamster, etc). An immune cell of the method may be any type of immune cell (e.g., B lymphocytes, monocytes, dendritic cells, Langerhans cells, keratinocytes, endothelial cells, astrocytes, fibroblasts, and oligodendrocytes). T cells (including T cytotoxic, T helper and Treg cells) are especially preferred. In specific embodiments, the cells are T cells, which may be obtained as described herein and by methods known in the art. Any type of immune cell may be employed in this embodiment of the disclosed method, and the cell may be a human or non-human cell. Exemplary cells include, but are not limited to immune cells such as T cells, tumor infiltrating lymphocytes (TILs), NK cells, TCR-expressing cells, dendritic cells, and NK-T cells. The T cells may be autologous, allogeneic, or heterologous. In additional embodiments, the cells are T cells presenting a CAR. The T cells may be CD4+ T cells or CD8+ T cells. When a T cell is employed in the disclosed methods, the T cell may be an in vivo T cell or an in vitro T cell. Moreover, the cells may be disposed in, or isolated from, any environment capable of maintaining the cells in a viable form, such as blood, tissue or any other sample obtained from a subject, cell culture media, tissue grown ex vivo, a suitable buffer, etc. As the disclosed method may be employed in therapeutic settings, in preferred embodiments the population of immune cells are disposed in a subject, and more preferably a human subject.

Continuing, immune cells are contacted with an antigen binding molecule that specifically binds to (a) the molecule comprising the selected amino acid sequence (i.e., SEQ ID NO: 1 or 46), and (b) an activating molecule expressed on the surface of an immune cell not expressing the molecule comprising the selected amino acid sequence, under conditions that permit the formation of a ternary binding complex comprising the molecule comprising the selected amino acid sequence (i.e., SEQ ID NO: 1 or 46), the activating molecule and the antigen binding molecule. The antigen binding molecule may be disposed on any surface, or no surface at all. In some embodiments, CAR T cells are able to kill other CAR T cells. In some embodiments, non-expressing cells and CAR-expressing cells are both able to kill CAR-expressing cells.

For example, the antigen binding molecule (which may also comprise the population of immune cells to be depleted and/or may be present in a buffer) and the buffer-antigen binding molecule may be contacted with the sample. Alternatively, the antigen binding molecule may be associated with a surface. Suitable surfaces include agarose beads, magnetic beads such as DYNABEADS, or a plastic, glass or ceramic plate such as a welled plate, a bag such as a cell culture bag, etc. The surface may itself be disposed in another structure, such as a column.

The immune cells are contacted with the antigen binding molecule, under conditions that permit the formation of a ternary binding complex comprising a molecule comprising the selected amino acid sequence (i.e., SEQ ID NO: 1 or 46), the antigen binding molecule and an activating molecule expressed on the surface of an immune cell not expressing the molecule comprising the selected amino acid sequence (i.e., SEQ ID NO: 1 or 46). Conditions that permit the formation of a binding complex will be dependent on a variety of factors, however generally aqueous buffers at physiological pH and ionic strength, such as in phosphate-buffered saline (PBS), will favor formation of binding complexes and are preferred in the disclosed method. Since the component parts of a binding complex may be disposed on surfaces as described herein, formed binding complexes may also be disposed on surfaces.

In preferred embodiments, the contacting is performed by administering the antigen binding molecule directly to a subject. In this embodiment, the subject will already have a population of cells to be depleted, wherein the cells express a molecule comprising the selected amino acid sequence (i.e., SEQ ID NO: 1 or 46). Thus, these cells, as well as cells presenting an activating molecule, will be present in the subject prior to the administration of the antigen binding molecule to the subject. The human blood, lymph and tissue environment will permit the formation of ternary binding complexes. The binding of the antigen binding molecule with the molecule comprising the selected amino acid sequence (i.e., SEQ ID NO: 1 or 46) serves to "tag" those cells presenting the molecule comprising the selected amino acid sequence (i.e., SEQ ID NO: 1 or 46) (i.e., the cells to be depleted). This binding event may or may not lead to depletion on its own. When the antigen binding molecule binds the activating molecule to form the ternary binding complex, however, this binding event brings both cells (i.e., the cell expressing the molecule comprising the selected amino acid sequence (i.e., SEQ ID NO: 1 or 46), and the cell expressing the activating molecule) together into proximity. The physiological result of the binding event is the killing of the cell expressing the molecule comprising the selected amino acid sequence (i.e., SEQ ID NO: 1 or 46). Thus, with multiple binding events occurring throughout the subject the population of immune cells bearing the molecule comprising the selected amino acid sequence (i.e., SEQ ID NO: 1 or 46) are depleted and the risk of harm to the subject decreases.

Vh. Method of Monitoring a Molecule In Vivo

Positron emission tomography (PET) imaging is often used in oncology research and patient care. For space-occupying lesions in the head, chest, abdomen and pelvis, one of the best documented applications of PET is in the discrimination of benign from malignant causes. Particularly, $^{18}$F-fluorodeoxyglucose (FDG) has been used to image the distribution of glucose uptake in all of these applications. In addition, the development of other radiotracers which image different aspects of tumor metabolism and growth add a further dimension of capabilities. These tracers include $^{11}$C-methionine to measure amino acid incorporation, $^{18}$F-thymidine to measure nucleotide incorporation (a measure of cell proliferation), and $^{18}$F-fluoromisonidazole to measure tissue hypoxia.

The present invention provides the use of antigen binding molecules in PET analysis to increase specificity of FDG uptake. In particular, the methods provided herein may be used to assess changes early after treatment with CAR cells, in addition to monitoring, detection, stimulation, activation, or depletion of CAR T-cells. Specifically, the methods provided herein may facilitate the use of PET for whole-body scans. Using this technique to stage cancer, occult metastatic disease in almost any region of the body may potentially be detected by increased FDG accumulation.

In some embodiments, the present invention provides an in vivo method of detecting a molecule comprising an amino acid sequence selected from the group consisting of SEQ ID NO: 1, or 46. For example, in particular embodiments, the antigen binding molecules may be used to follow or monitor the presence or absence of a molecule comprising an amino acid sequence selected from the group consisting of SEQ ID NO: 1 or 46 in a living subject. In some embodiments, the living subject is a human. In some embodiments, the molecule comprising an amino acid sequence selected from the group consisting of SEQ ID NO: 1 or 46 is provided to a living subject and the presence or absence of said molecule is determined using an antigen binding molecule provided herein and a positron emission tomography (PET) scan.

In some embodiments, antigen binding molecules provided herein may be used to control CAR T-cells in vivo. In some embodiments, the antigen binding molecules provided herein may be used to activate or stimulate CAR T-cells in vivo. In some embodiments, the antigen binding molecules provided herein may be used to deplete CAR T-cells in vivo. In some embodiments, the antigen binding molecules provided herein may be used to monitor CAR T-cells in vivo. Specifically, when combined with PET, antigen binding molecules provided herein (e.g., anti-linker antibodies) may be used to monitor or follow the distribution of cells expressing a molecule comprising a selected amino acid sequence (e.g., SEQ ID NO: 1 or 46) in vivo.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The foregoing written specification is considered to be sufficient to enable one skilled in the art to practice the invention. The foregoing description and Examples that follow detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

The present invention is further illustrated by the following examples which should not be construed as further limiting. The contents of all references cited throughout this application are expressly incorporated herein by reference.

Example 1: Generation of Antigen Binding Molecules

Monoclonal antibodies were generated through immunization of rabbits using the 15 mer peptide, GGGGSGGGGSGGGGS (SEQ ID NO: 45), conjugated to the carrier protein KLH as immunogen. Titer was determined via screening polyclonal sera by ELISA using the full-length linker peptide, GGGGSGGGGSGGGGS (SEQ ID NO: 45), conjugated to ovalbumin. A secondary screen was performed using CAR T cells assayed via flow cytometry. Once titer was achieved, the immunized rabbits were sacrificed and monoclonals were derived using standard hybridoma generation and subcloning techniques. The final screening of the hybridoma subclones was accomplished via additional rounds of flow cytometry and immunohistochemistry (IHC) of proliferating CAR T cells or fixed cell pellets derived from CAR T cells, respectively. The sequences of the final three subclones selected were determined by standard Sanger sequencing of the hybridomas subclones.

Example 2: Immunohistochemistry (IHC)

The candidate antibodies may be screened for their utility in immunohistochemistry. To create the fixed cell pellets for IHC staining, ~2e6 CAR T cells may be centrifuged and washed with PBS. The cells may be resuspended in PBS containing 0.45% paraformaldehyde (PFA) and incubated on a shaking platform for 2 hours at room temperature. After the incubation, the cells may be washed once more with PBS and resuspended in PBS with 5% BSA. CAR transduced cells may be positively recognized by exemplary anti-linker antibodies provided herein.

Example 3: Epitope Mapping

The antibodies (i.e., antigen binding molecules) may be epitope mapped via ELISA using the full-length peptide, GGGGSGGGGSGGGGS (SEQ ID NO: 45), and variants truncated on either the N- or C-terminus and containing either a biotin moiety on the N-terminus, or a lysine residue with a biotin moiety on the C-terminus. The antibodies may be captured in 96-well plate format using plates pre-coated with Protein G (Pierce). The plates were washed 6× in PBST buffer followed by incubation with target peptides. An additional 6× wash was performed with PBST and the antibodies may be further incubated with streptavidin-HRP. Upon a final 6× wash in PBST, signal may be detected and quantified via enhanced chemiluminesense kit (ECL, from GE Healthcare) and a Varioskan Flash plate reader (Thermo Fisher).

Example 4: Generation of Humanized Sequences from Rabbit Antibodies Clone 132, Clone 154, and Clone 163

The Molecular Operating Environment (MOE) software developed by Chemical Computing Group (CCG) are used to generate alignments between the rabbit antibody clone 132, clone 154 and clone 163 and pairs of variable light and heavy chains, VL and VH, respectively from two databases:

(1) The Abysis human database: a database of about 2000 known human VL/VH sequence pairs from IMGT-LigM DB; and (2) A human germline database: a database of germline sequences.

Humanized models show the best sequence alignments (highest identity to both the VL and VH domains) with fewest gaps. The top 100 antibody pairs from each human database are exported and clustered using kClust (Hauser, Mayer, & Soding, (2013) *BMC Bioinformatics*, 248).

Example 5: Use of an Anti-Linker Antibody for Purifying Macromolecules and Cells The antigen binding molecules disclosed herein are antigen binding molecules, such as antibodies, which specifically bind to the sequence GGGGS (SEQ ID NO: 46) and subsequences thereof, particularly GGGS (SEQ ID NO: 1), molecules comprising these sequences and cells presenting such molecules, polynucleotides encoding such antigen binding molecules, as well as humanized forms of the antigen binding molecules. An antigen binding molecule (e.g., an antibody) disclosed herein may thus be used to purify a molecule, such as, macromolecule, polymer, cell, material, etc., displaying an epitope that is recognized by the antigen binding molecules disclosed herein (e.g., GGGGS (SEQ ID NO: 46) and subsequences thereof, particularly GGGS (SEQ ID NO: 1)).

In one embodiment, an antigen binding molecule disclosed herein (e.g., Clones 132, 154, 163 and fragments thereof) may be attached to beads, attached to or associated with a resin, which may be disposed in a column or other structure. A sample comprising a molecule comprising all or a fragment GGGGS (SEQ ID NO: 46) and subsequences thereof, particularly GGGS (SEQ ID NO: 1)) may then be contacted with the beads, resin, etc. to which the antigen binding molecule was attached or with which an antigen binding molecule was associated. This allows the formation of an association or binding complex comprising the antigen binding molecule and the molecule comprising all or a fragment of GGGGS (SEQ ID NO: 46) and subsequences thereof, particularly GGGS (SEQ ID NO: 1). The beads or resin may then be washed with a suitable solution, such as a buffer solution (e.g., PBS, HEPES, MOPS, Tris, Tricine, etc) having a pH selected to maintain the stability of the molecule comprising all or a fragment of GGGGS (SEQ ID NO: 46) and subsequences thereof, particularly GGGS (SEQ ID NO: 1). The washing may remove unwanted and unbound components of the sample. Following the washing step, the molecule comprising all or a fragment of the GGGGS (SEQ ID NO: 46) and subsequences thereof, particularly GGGS (SEQ ID NO: 1) may then be eluted from the antigen binding molecules using an elution buffer and conditions selected to disrupt any association or binding complexes formed. Examples of suitable elution buffers include incubation with peptide epitope in molar excess, 0.1M glycine, pH 2.5-3.0, and 0.1M citric acid, pH 3.0, 50-100 mM triethylamine or triethanolamine, pH 11.5, 3.5-4.0M magnesium chloride, pH 7.0 in 10 mM Tris, 2-6M guanidine, and 2-8M urea, or a buffer solution around pH 7-8, including, but not limited to, 10 mM Tris, HEPES, or 1×PBS, containing free peptide GGGGS (SEQ ID NO: 46) and subsequences thereof, particularly GGGS (SEQ ID NO: 1). During the elution step, eluted molecules, cells and moieties of interest comprising all or a fragment of GGGGS (SEQ ID NO: 46) and subsequences thereof, particularly GGGS (SEQ ID NO: 1) is collected, and purity may be subsequently checked by running a sample on an SDS polyacrylamide gel.

In another embodiment, an antigen binding molecule may be disposed in solution with any molecular entity displaying the epitope, and purified from a mixed population of molecules, cells, etc. and eluted from the beads, resin, or free antibody by washing with 300-500 mM sodium chloride or lowering the pH and neutralizing with 1 M Tris, for proteins, or phosphate buffer, or with buffer containing free peptide, such as GGGGS (SEQ ID NO: 46) and subsequences thereof, particularly GGGS (SEQ ID NO: 1). Subsequently, dialysis may be used to return materials to desired buffer conditions.

In a specific embodiment, cells displaying a molecule comprising all or a fragment of GGGGS (SEQ ID NO: 46) and subsequences thereof, particularly GGGS (SEQ ID NO: 1) may be incubated with magnetic beads (e.g., DYNABEADS) with which an antigen binding molecule disclosed herein has been associated. Preferably the incubation is performed under conditions that both allow for the formation of binding complexes/associations, such as under physiological conditions, in the presence of a media selected for this purpose (e.g., RPMI-1640).

Cells bound by the beads (which will be presenting molecules comprising GGGGS (SEQ ID NO: 46) and subsequences thereof, particularly GGGS (SEQ ID NO: 1)) are then separated from cells not displaying a molecule comprising GGGGS (SEQ ID NO: 46) and subsequences thereof, particularly GGGS (SEQ ID NO: 1). In one embodiment, the beads may be washed with media, such as RPMI-1640 supplemented with 10% FBS, in the presence of a magnet.

Selected cells, i.e., those presenting molecules that comprise GGGGS (SEQ ID NO: 46) and subsequences thereof, particularly GGGS (SEQ ID NO: 1) may then be separated from the beads: First, selected cells are grown out in media. After growing out cells for 48 hours, the magnetic beads may be separated from cells in solution and discarded, leaving a pure population of cells presenting desired molecule.

In an alternative embodiment, the beads are not magnetic, and in this embodiment, the above steps may also be followed and adapted to maintain cell integrity, but also to allow separation of bead-bound cells from non-bead bound cells.

In an alternative embodiment, an antigen binding molecule disclosed herein (e.g., Clones 132, 154, and 163 and fragments thereof) may be His-tagged (i.e., labeled with a short polyhistidine sequence), thereby facilitating the separation of cells using a resin comprising a transition metal ion such as $Ni^{2+}$, $Co^{2+}$, $Cu^{2+}$ or $Zn^{2+}$, which are immobilized on the resin. The antigen binding molecules may then be incubated with cells known or suspected to be presenting a molecule GGGGS (SEQ ID NO: 46) and subsequences thereof, particularly GGGS (SEQ ID NO: 1) under conditions suitable for the formation of complexes comprising the cells and the antigen binding molecules. Following the incubation, the cells are contacted with the resin, which may be disposed in a solid structure such as a welled plate, column or other structure. The antigen binding molecule-cell complexes may then be separated from one another by washing with imidazole, which will be of a higher concentration than any imidazole included in any solutions used in the formation of the binding complexes. Eluted cells may then be spun down, washed in RPMI or other suitable media, and then resuspended in media.

Example 6: Sorting of CAR-Positive T Cells

PBMCs may be isolated from healthy donor leukopaks (Hemacare™) using Ficoll-Paque density centrifugation per manufacturer's instructions. PBMCs may be stimulated using OKT3 (50 ng/ml, Miltenyi Biotec™) in R10 media+ IL-2 (300 IU/ml, Proleukin®, Prometheus® Therapeutics and Diagnostics). Two days after stimulation, CAR T cells are generated through viral transduction of these activated primary human T cells. Transduction may be performed using either a retro- (pMSVG vector) or lentivirus (pGAR vector) depending upon the origin of the CARs used in the screening. Confirmation of CAR construct expression and viral transduction efficiency may be determined using Protein L conjugated to phycoerythrin (PE) or fluorescein isothiocyanate (FITC).

Cultured CAR T-cells were removed from culture, washed with PBS, and incubated with the anti-linker antibody described herein may be conjugated to PE for 30 minutes in stain buffer comprising PBS pH 7.4, 0.2% (w/v) bovine serum albumin, and 0.09% sodium azide. Cells may be washed two times in stain buffer, resuspended and sorted with a BD Aria cell sorter. Negatively- and positively-gated cells may be analyzed post sort for composition.

Example 7: Stimulating/Activating CAR-Positive T Cells Using an Antigen Binding Molecule T-cells are often stimulated through their T-cell receptors (TCR) using an anti-CD3 antibody, such as clone OKT3, a mouse anti-CD3 antibody, along with an anti-CD28 antibody to provide a second signal or costimulatory signal. CAR T-cells, upon interaction with cognate antigen may provide both signals through their intracellular CD3zeta and costimulatory domain, such as CD28.

Accordingly, also provided is a method of activating CAR-positive T cells presenting a molecule comprising a specific epitope recognized by a specific antigen binding molecule (e.g., an antigen binding molecule, that recognizes a molecule comprising GGGGS (SEQ ID NO: 46) and subsequences thereof, particularly GGGS (SEQ ID NO: 1)), such as those disclosed herein: Clone 132, 154, or 163 and fragments thereof). This method may be adapted for any antibody recognizing a protein of interest on a T cell containing an activation domain, such as a chimeric antigen receptor (CAR) comprising GGGGS (SEQ ID NO: 46) and subsequences thereof, particularly GGGS (SEQ ID NO: 1). Activation may be achieved using plate-bound, bead-bound, polymer-bound, or other form of the antibody that specifically recognizes an extracellular component of the CAR or similar molecule.

In this Example, CAR positive (CAR+) T-cells may be selectively stimulated in vitro with an anti-linker antibody, such as those provided herein. For purposes of comparison, OKT3 antibodies, which are commonly used to activate T cells in vitro (see, e.g., Landegren et al., (1984) *Eur. J. Immunol.* 14(4):325-28) may be used to stimulate all T-cells. Bags, flasks, plates, or other vessels for growing T-cells may be used for the stimulation or, as described herein, welled plates may also be used for the stimulation.

In one instance, CAR-T cells are sorted, as described in EXAMPLE 6, and mixed to form populations of cells at fixed percentages of CAR-positive cells; these cells may then be allowed to recover from sort for 24 hours at 37° C. in OpTmizer media. 12-well tissue culture treated plates may be incubated with either OKT3 or anti-linker antibody at 1.5 µg/mL in HBSS for 2 hours at 37° C., and washed three times with HBSS. 0.5e6 T-cells of defined populations may be added in 2 mL of OpTmizer media with IL-2 to the plates pre-coated with antibody and cells are incubated for up to 1 week at 37° C. and sampled at various time points.

Samples may be analyzed by flow cytometry to check for presence of CAR and various activation markers, including CD25, CD69, and 4-1BB. Over time, it may be observed that OKT3 antibodies stimulate all T-cells, and the percentage of CAR-positive cells may be unchanged. In contrast, when incubated with the anti-linker antibody, T-cells that are CAR-positive receive stimulation and proliferate, becoming a larger percentage of the population.

Thus, cells presenting a molecule comprising GGGGS (SEQ ID NO: 46) and subsequences thereof, particularly GGGS (SEQ ID NO: 1), may be selectively stimulated in vitro.

Example 8: Stimulating/Activating CAR-Positive T Cells Using an Antigen Binding Molecule In Vivo In this example, CAR+ T-cells may be selectively stimulated in vivo with an anti-linker antibody, provided herein. CAR-T cells comprising the peptide GGGGS (SEQ ID NO: 46) and subsequences thereof, particularly GGGS (SEQ ID NO: 1) may be injected on Day 6. On Day 13, fludeoxy-glucose positron emission tomography (FDG-PET) experiments may be performed to assess baseline metabolism. Clone 132, 154, or 163 anti-linker antibodies may be injected into each mouse and the FDG-PET experiment repeated after 24 hours.

Example 9: Depletion of Cells Expressing Molecules Containing Specific Peptides Using a Diabody In this Example, cells expressing a molecule comprising GGGGS (SEQ ID NO: 46) and subsequences thereof, particularly GGGS (SEQ ID NO: 1) (e.g., CAR+ T-cells) may be selectively killed in vitro with an anti-linker/anti-human CD3 diabody, comprising an anti-linker binding moiety, such as in Clone 132, 154, 163. T-cells transduced with a CAR comprising the specific epitope GGGGS (SEQ ID NO: 46) and subsequences thereof, particularly GGGS (SEQ ID NO: 1), a CAR not containing the epitope, or not transduced (Mock) may be grown in 96-well U-bottom in OpTmizer media with T-cell supplements, penicillin, streptomycin, glutamine, and IL-2. Each well may contain 20,000 T-cells. The diabody may be added to each CAR- and Mock-transduced T-cell samples at concentrations from 1.28 pM to 100 nM. After 16 hours, cells may be stained with Live/Dead Violet (Molecular Probes) and recombinant protein L/streptavidin-PE to assess the number of dead cells and percentage of CAR+ T-cells as a function of the concentration of the diabody. The amount of dye that binds to cells with ruptured membranes may be increased in the CAR comprising the specific epitope GGGGS (SEQ ID NO: 46) and subsequences thereof, particularly GGGS (SEQ ID NO: 1) samples, whereas the expression of a control CAR or no CAR may not lead to a significant increase in dye fluorescence. Thus, cells presenting a molecule comprising GGGGS (SEQ ID NO: 46) and subsequences thereof, particularly GGGS (SEQ ID NO: 1), may be selectively depleted in vitro with a diabody specific for T-cells and the specific peptide.

Example 10: Antibody Binding Profile of Exemplary Linker Sequences

The specific binding of a panel of antibodies raised against a CAR comprising the linker sequence of GST-SGSGKPGSGEGSTKG (SEQ ID NO: 44), the linker sequence GGGGSGGGGSGGGGS (SEQ ID NO: 45), or the or the anti-CD19 scFv clone FMC63 were used to determine the antibody binding profile of exemplary linker sequences from the KIP-1, KIP-4, and KIP-3 antibodies respectively. KIP-4 is an exemplary antibody that specifically binds to peptides comprising the amino acid sequence GGGGS (SEQ ID NO: 46) or GGGS (SEQ ID NO: 1) as described herein. The antibodies were captured in 96-well plate format using plates pre-coated with Protein G (Pierce). The plates were washed 6× in PBST buffer followed by incubation with target peptides. An additional 6× wash was performed with PBST and the antibodies were further incubated with streptavidin-HRP. Upon a final 6× wash in PBST, signal was detected and quantified via enhanced chemiluminescense kit (ECL, from GE Healthcare) and a Varioskan Flash plate reader (Thermo Fisher). The results of the antibody profile ELISA experiments, shown in FIG. 3 demonstrate the breadth of antibody binding of linkers according to the present invention.

Figure 4:
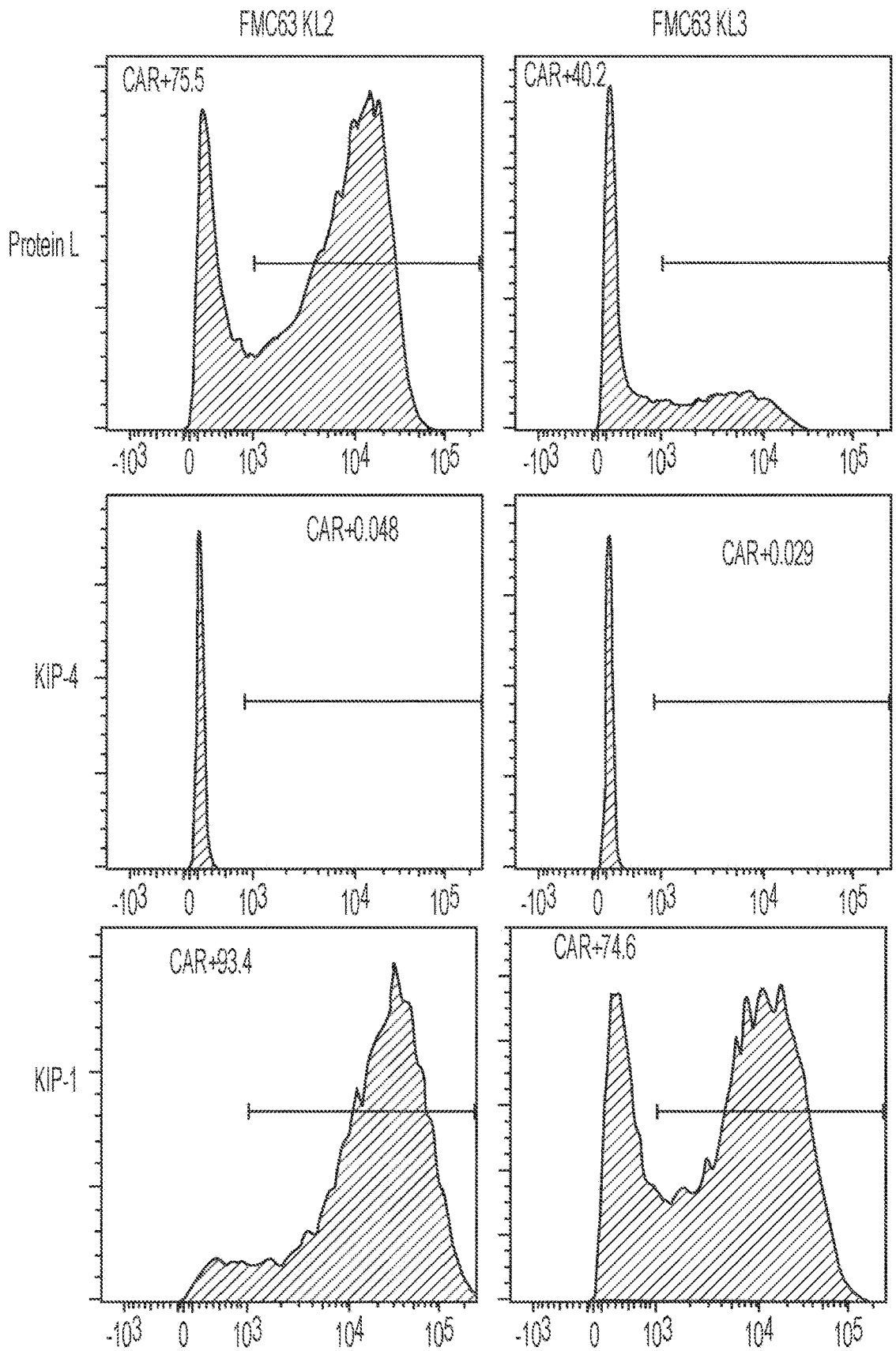
FIG. 4 is a series of plots showing the results of flow cytometry experiments performed using cells presenting a chimeric antigen receptor (CAR) comprising the linker peptide KL2 (SEQ ID NO: 50), KL3 (SEQ ID NO: 51), KL4 (SEQ ID NO: 47), KL5 (SEQ ID NO: 52), KL6 (SEQ ID NO: 48), and G4S2 (SEQ ID NO: 53).
Figure 4:
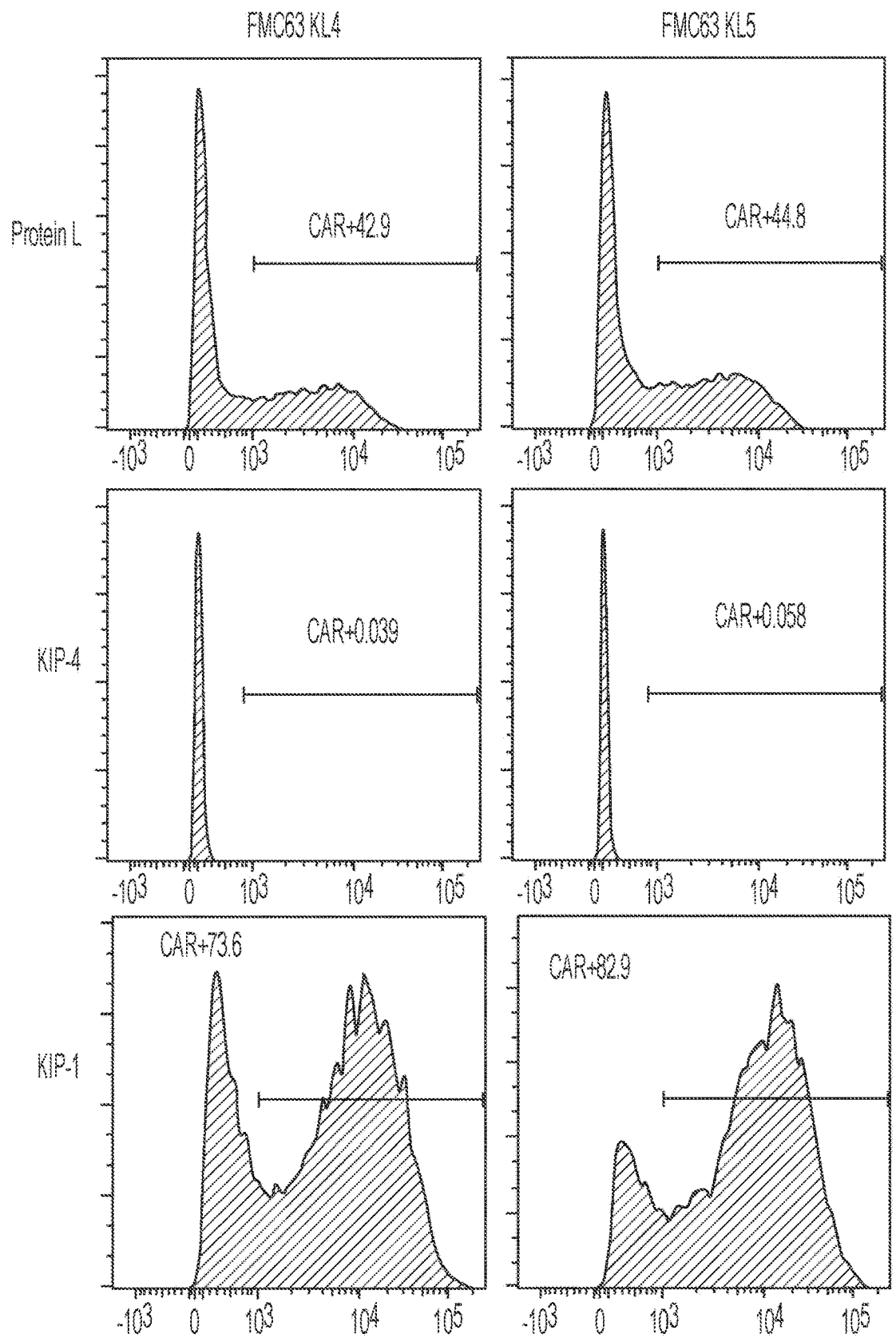
Figure 4:
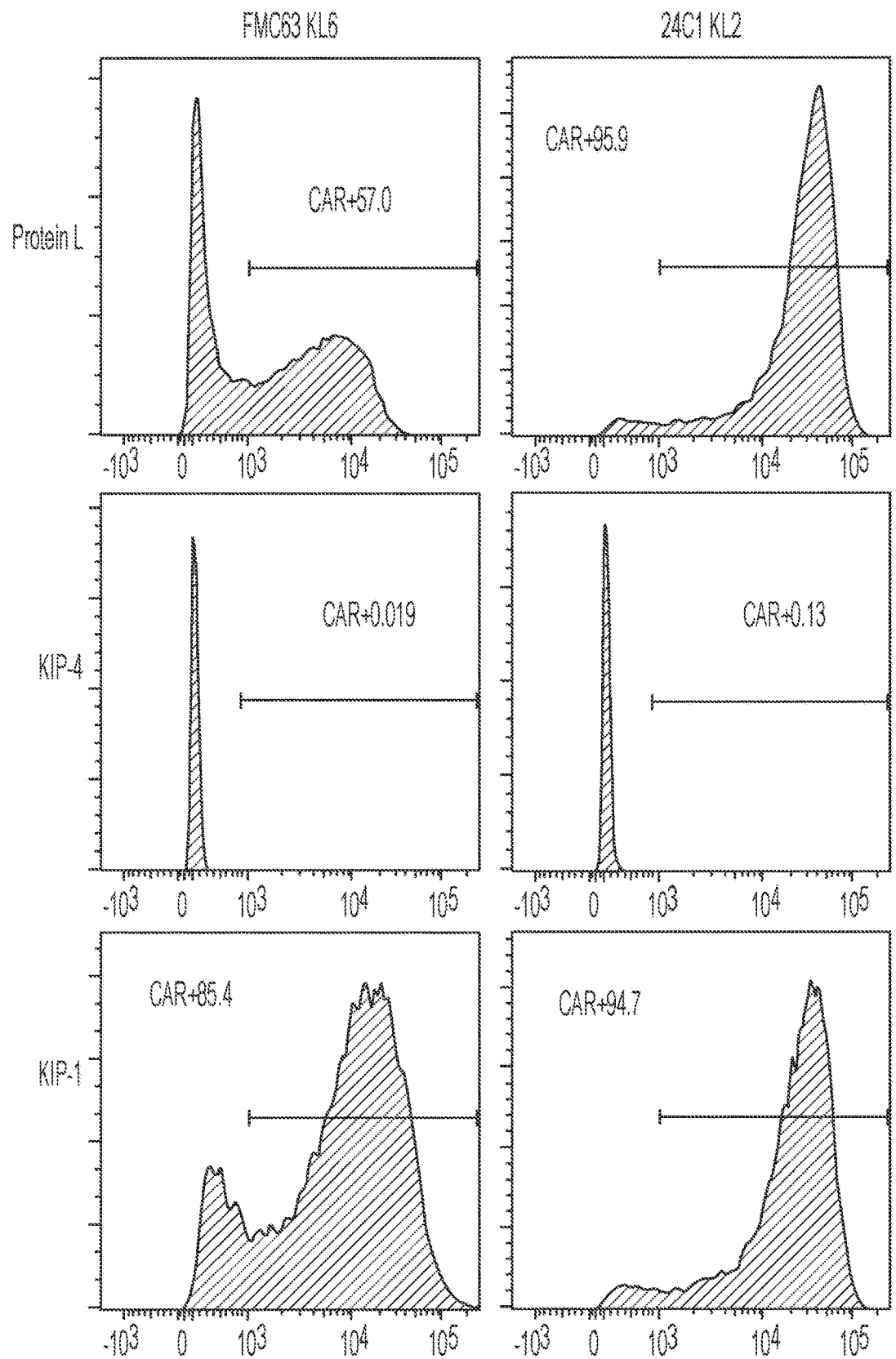
Figure 4:
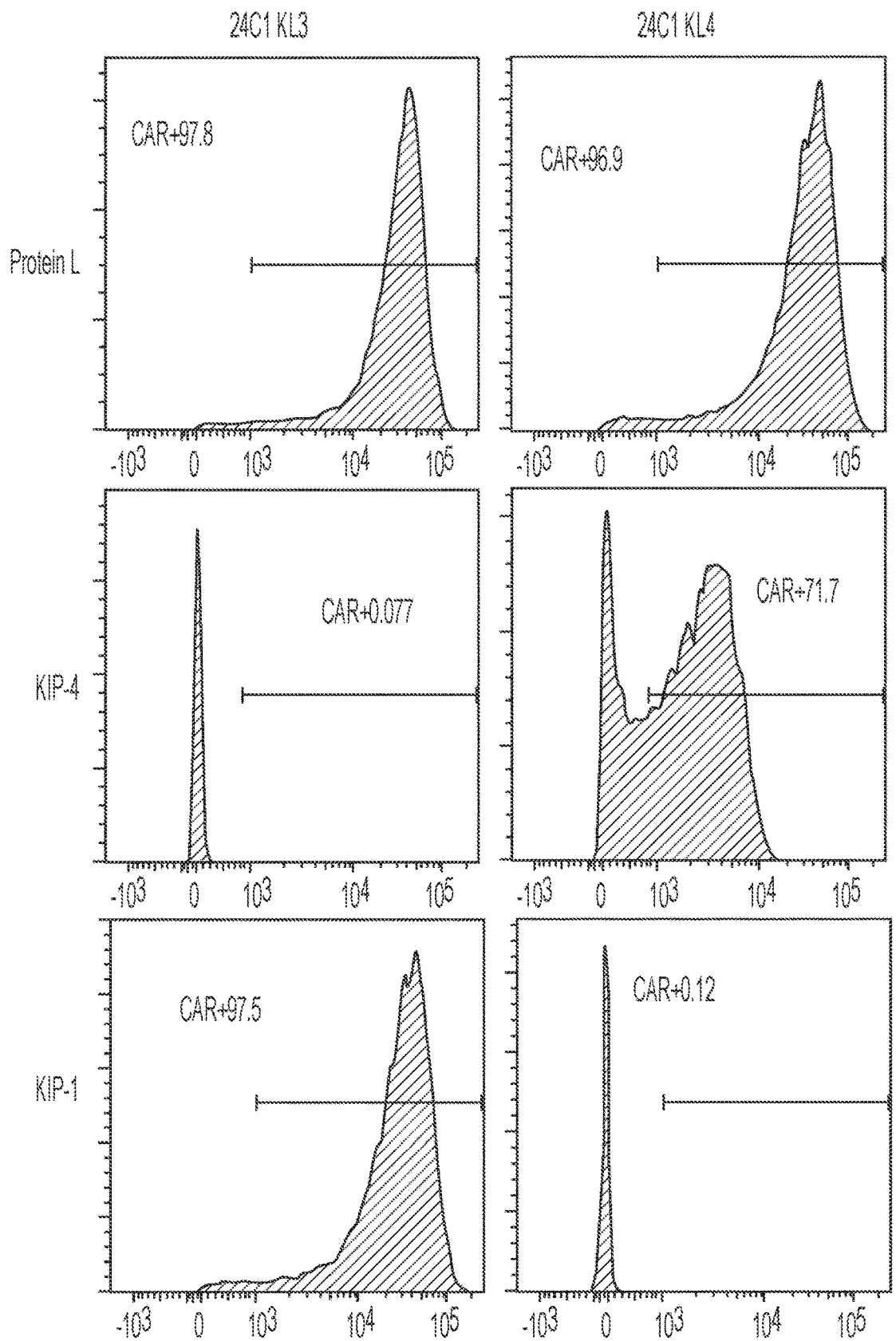
Figure 4:
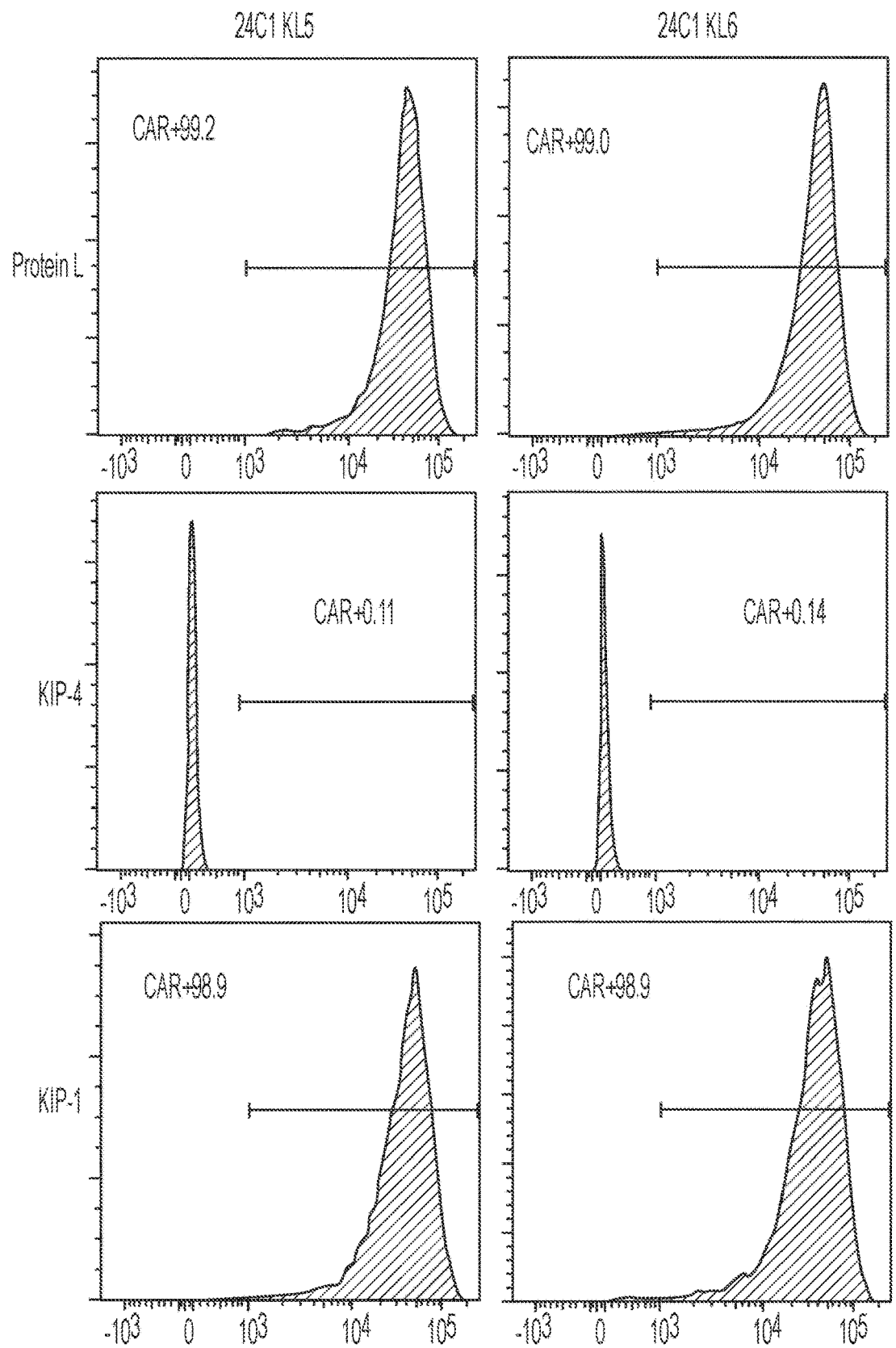
Figure 4:
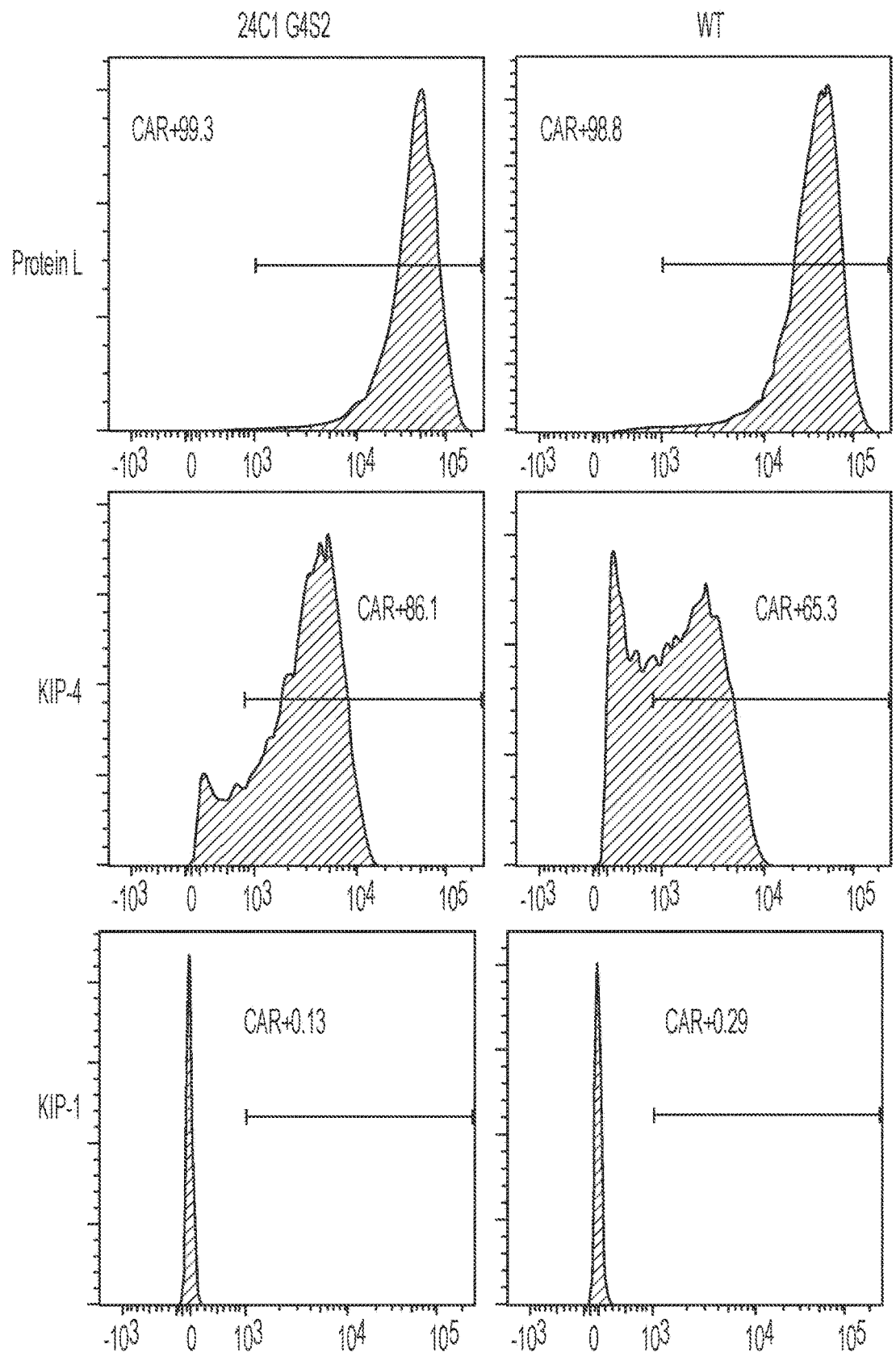
Figure 4:
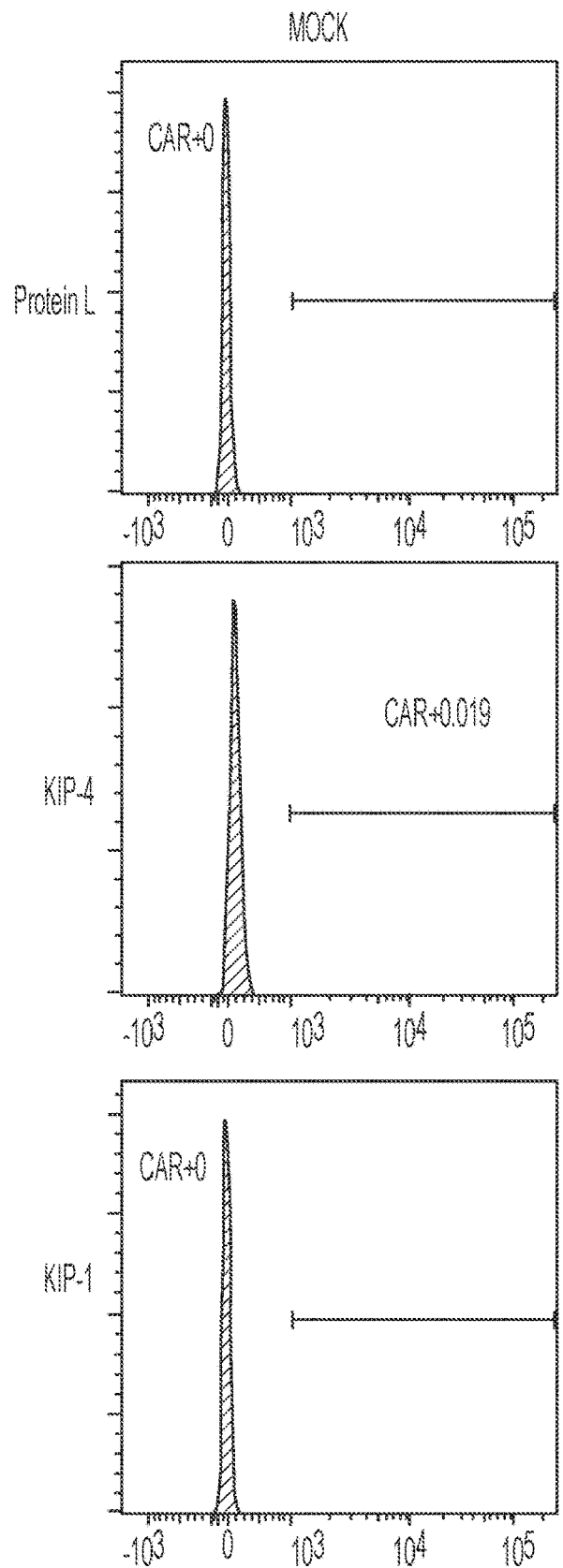

Example 11: Flow Cytometry of Car Expressing Cells Comprising Chimeric Linkers CAR T cells were assayed via flow cytometry using Protein L as a control to confirm the expression of each CAR construct comprising the linker sequences SEQ ID NO: 44 (FMC63 WT), or the SEQ ID NO: 45 (FMC63 G4S). These results confirm expression of the CAR constructs on the surface of T cells. As shown in FIG. 4, CAR T cells were produced in the context of scFv FMC63 and 24C1 scFv. KL2 (SEQ ID NO: 50), KL3 (SEQ ID NO: 51), KL4 (SEQ ID NO: 47), KL5 (SEQ ID NO: 52), KL6 (SEQ ID NO: 48), and G4S2 (SEQ ID NO: 53) linkers were used to link the VL and VH domains of the scFv.

Sequences and SEQ ID NOs

The instant disclosure comprises a number of nucleic acid and polypeptide sequences. For convenience, Table C below correlates each sequence with its appropriate description and SEQ ID NO.

Table C

| SEQ ID NO. | Description | Sequence |
|---|---|---|
| SEQ ID NO: 1 | G3S Consensus | GGGS |
| SEQ ID NO: 2 | KIP-4_132_VH | METGLRWLLLVAVLKGVQCQEQLEESGGDLVQPEG SLTLTCTASGFSFSSSYYMCWVRQAPGKGLEWIAC IDDGGSYTYYASWAKGRFTISKTSSTTVTLQMTSL TDADTATYFCTRHVRGADYYNLWGPGTLVTVSS |
| SEQ ID NO: 3 | KIP-4_132_VL | MDTRAPTQLLGLLLLWLPGATFAIVMTQTPSSVSAA VGGTVTISCQASQSVYNNNRLSWYQQKPGQPPKLLI YLASTLASGVPSRFKGSGSGTQFTLTISDLECDDAA TYYCAGYQYSETDGFAFGGGTEVVVK |
| SEQ ID NO: 4 | KIP-4_154_VH | METGLRWLLLVAVLKGVQCQSLEESGGDLVKPEGSL TLTCTASGFSFSSSAYMCWVRQAPGKGLEWIACIYG SNSGNTYYANWAKGRFTISKTSSTTVTLQMTSLTA ADTATYFCARYAVGSWDYFDLWGPGTLVTASS |
| SEQ ID NO: 5 | KIP-4_154_VL | MDTRAPTQLLGLLLLWLPGARCDFVMTQTPASVSEP VGGTVTIKCQASQSIGSHLAWYQQKPGQPPKLLIYG ASTLASGVPSRFKGSGSGTQFTLTISDLECADAATY YCQCTYAGGYYVFAFGGGTEVVVK |
| SEQ ID NO: 6 | KIP-4_163_VH | METGLRWLLLVAVLKGVQCQQQLEESGGDLVKPEG SLTLTCTASKFSFNKKYYMCWVRQAPGKGLEWIGC VDTGDAFIGYANWAKGRFTVSKTSSTTVDLKMTSLT AADTATYFCARGVYPINTGYYYFDLWGPGTLVTVSS |
| SEQ ID NO: 7 | KIP-4_163_VL | MDTRAPTQLLGLLLLWLPGARCALVMTQTPASVEAA VGGTVTIKCQASEDITNSLAWYQQKPGQPPNLLIYR ASTLASGVSSRFKGSRSGTEFTLTISGVECADAATY YCQQGYSSTNVDNIFGGGTEVVVK |
| SEQ ID NO: 8 | 132_VL CDR1 (Kabat) (Clothia) | QASQSVYNNNRLS |
| SEQ ID NO: 9 | 132_VL CDR2 (Kabat) (Clothia) (IMGT) | LASTLAS |
| SEQ ID NO: 10 | 132_VL CDR3 (Kabat) (Clothia) (IMGT) | AGYQYSETDGFA |
| SEQ ID NO: 11 | 154_VL CDR1 (Kabat) (Clothia) | QASQSIGSHLA |
| SEQ ID NO: 12 | 154_VL CDR2 (Kabat) (Clothia) (IMGT) | GASTLAS |
| SEQ ID NO: 13 | 154_VL CDR3 (Kabat) (Clothia) (IMGT) | QCTYAGGYYVFA |

Table C-continued

| SEQ ID NO. | Description | Sequence |
|---|---|---|
| SEQ ID NO: 14 | 163_VL CDR1 (Kabat) (Clothia) | QASEDITNSLA |
| SEQ ID NO: 15 | 163_VL CDR2 (Kabat) (Clothia) (IMGT) | RASTLAS |
| SEQ ID NO: 16 | 163_VL CDR3 (Kabat) (Clothia) (IMGT) | QQGYSSTNVDNI |
| SEQ ID NO: 17 | 132_VH CDR1 (Kabat) | SSYYMC |
| SEQ ID NO: 18 | 132_VH CDR2 (Kabat) | CIDDGGSYTYYASWAK |
| SEQ ID NO: 19 | 132_VH CDR3 (Kabat) (Clothia) | HVRGADYYNL |
| SEQ ID NO: 20 | 154_VH CDR1 (Kabat) | SSAYMC |
| SEQ ID NO: 21 | 154_VH CDR2 (Kabat) | CIYGSNSGNTYYANWAK |
| SEQ ID NO: 22 | 154_VH CDR3 (Kabat) (Clothia) | YAVGSWDYFDL |
| SEQ ID NO: 23 | 163_VH CDR1 (Kabat) | KKYYMC |
| SEQ ID NO: 24 | 163_VH CDR2 (Kabat) | CVDTGDAFIGYANWAK |
| SEQ ID NO: 25 | 163_VH CDR3 (Kabat) (Clothia) | GVYPINTGYYYFDL |
| SEQ ID NO: 26 | 132_VH CDR1 (Clothia) | GFSFSSSY |
| SEQ ID NO: 27 | 132_VH CDR2 (Clothia) | DDGGS |
| SEQ ID NO: 28 | 154_VH CDR1 (Clothia) | GFSFSSSA |
| SEQ ID NO: 29 | 154_VH CDR2 (Clothia) | YGSNSG |
| SEQ ID NO: 30 | 163_VH CDR1 (Clothia) | KFSFNKKY |
| SEQ ID NO: 31 | 163_VH CDR2 (Clothia) | DTGDA |
| SEQ ID NO: 32 | 132_VL CDR1 (IMGT) | QSVYNNNR |
| SEQ ID NO: 33 | 154_VL CDR1 (IMGT) | QSIGSH |
| SEQ ID NO: 34 | 163_VL CDR1 (IMGT) | EDITNS |
| SEQ ID NO: 35 | 132_VH CDR1 (IMGT) | GFSFSSSYY |
| SEQ ID NO: 36 | 132_VH CDR2 (IMGT) | IDDGGSY |
| SEQ ID NO: 37 | 132_VH CDR3 (IMGT) | TRHVRGADYYNL |
| SEQ ID NO: 38 | 154_VH CDR1 (IMGT) | GFSFSSSAY |
| SEQ ID NO: 39 | 154_VH CDR2 (IMGT) | IYGSNSGN |
| SEQ ID NO: 40 | 154_VH CDR3 (IMGT) | ARYAVGSWDYFDL |
| SEQ ID NO: 41 | 163_VH CDR1 (IMGT) | KFSFNKKYY |
| SEQ ID NO: 42 | 163_VH CDR2 (IMGT) | VDTGDAF |
| SEQ ID NO: 43 | 163_VH CDR3 (IMGT) | ARGVYPINTGYYYFDL |
| SEQ ID NO: 44 | Whitlow Linker | GSTSGSGKPGSGEGSTKG |
| SEQ ID NO: 45 | G45 linker | GGGGSGGGGSGGGGS |
| SEQ ID NO: 46 | G45 consensus | GGGGS |
| SEQ ID NO: 47 | KL 4 | GGGSGKPGSGEGGGS |
| SEQ ID NO: 48 | KL 6 | GGGSGKPGSGEGGGGS |
| SEQ ID NO: 49 | KL 1 | GGGGSGKPGSGGGGS |

Table C-continued

| SEQ ID NO. | Description | Sequence |
|---|---|---|
| SEQ ID NO: 50 | KL 2 | GGGGSGKPGSGEGGS |
| SEQ ID NO: 51 | KL 3 | GGGGSGKPGSGEGGGS |
| SEQ ID NO: 52 | KL 5 | GGGGSGKPGSGEGGGGS |
| SEQ ID NO: 53 | G452 | GGGGSGGGGSGGGGSG |
| SEQ ID NO: 54 | G453 | GGGGGSGGGGSGGGGS |
| SEQ ID NO: 55 | G454 | GGGGSGGGGSGGGGGS |
| SEQ ID NO: 56 | Clone 132 VH DNA Coding Sequence | ATGGAGACTGGGCTGCGCTGGCTTCTCCTGGTCGC TGTGCTCAAAGGTGTCCAGTGTCAGGAGCAGCTGG AGGAGTCCGGGGGAGACCTGGTCCAGCCTGAGGGA TCCCTGACACTCACCTGCACAGCTTCTGGATTCTC CTTCAGTAGCAGCTACTACATGTGCTGGGTCCGCC AGGCTCCAGGGAAGGGGCTGGAGTGGATCGCGTG CATTGATGATGGTGGTAGTTATACTTACTACGCGA GCTGGGCGAAAGGCCGATTCACCATCTCCAAAACC TCGTCGACCACGGTGACTCTGCAAATGACCAGTCT GACAGACGCGGACACGGCCACTTATTTCTGTACGA GACATGTTAGGGGTGCTGATTATTATAATTTGTGG GGCCCAGGCACCCTGGTCACCGTCTCCTCA |
| SEQ ID NO: 57 | Clone 132 VL DNA Coding Sequence | ATGGACACGAGGGCCCCCACTCAGCTGCTGGGGCTC CTGCTGCTCTGGCTCCCAGGTGCCACATTTGCCAT CGTGATGACCCAGACTCCATCCTCCGTGTCTGCAG CTGTGGGAGGCACAGTCACCATCAGTTGCCAGGCC AGTCAGAGTGTTTATAATAACAACCGCTTATCCTG GTATCAGCAGAAACCAGGGCAGCCTCCCAAGCTCC TGATCTATCTGGCATCCACTCTGGCATCTGGGGTC CCATCGCGGTTCAAAGGCAGTGGATCTGGGACACA GTTCACTCTCACCATCAGCGACCTGGAGTGTGACG ATGCTGCCACTTATTATTGTGCAGGATATCAATAT AGTGAGACTGATGGTTTTGCTTTCGGCGGAGGGAC CGAGGTGGTGGTCAAA |
| SEQ ID NO: 58 | Clone 154 VH DNA Coding Sequence | ATGGAGACTGGGCTGCGCTGGCTTCTCCTGGTCGC TGTGCTCAAAGGTGTCCAGTGTCAGTCGTTGGAGG AGTCCGGGGGAGACCTGGTCAAGCCTGAGGGATCC CTGACACTCACCTGCACAGCCTCTGGATTCTCCTT CAGTAGCAGCGCCTACATGTGCTGGGTCCGCCAGG CTCCAGGGAAGGGGCTGGAGTGGATCGCATGCATT TATGGTAGTAATAGTGGTAACACTTACTACGCGAA CTGGGCGAAAGGCCGATTCACCATCTCCAAAACCT CGTCGACCACGGTGACTCTGCAGATGACCAGTCTG ACAGCCGCGGACACGGCCACCTATTTCTGTGCGAG ATATGCTGTCGGTAGTTGGGACTATTTTGACTTGT GGGGCCCAGGCACCCTGGTCACCGCCTCCTCA |
| SEQ ID NO: 59 | Clone 154 VL DNA Coding Sequence | ATGGACACGAGGGCCCCCACTCAGCTGCTGGGGCT CCTGCTGCTCTGGCTCCCAGGTGCCAGATGTGATG TTGTGATGACCCAGACTCCAGCCTCCGTGTCTGAA CCTGTGGGAGGCACAGTCACCATCAAGTGCCAGGC CAGTCAGAGCATTGGTAGTCATTTAGCCTGGTATC AGCAGAAACCAGGGCAGCCTCCCAAGCTCCTGAT ATATGGTGCATCCACTCTGGCATCTGGGGTCCCAT CGCGGTTCAAAGGCAGTGGATCTGGGACACAGTTC ACTCTCACCATCAGCGACCTGGAGTGTGCCGATGC TGCCACTTACTACTGTCAATGTACTTATGCTGGTG GTTATTATGTTTTTGCCTTCGGCGGAGGGACCGAG GTGGTGGTCAAG |
| SEQ ID NO: 60 | Clone 163 VH DNA Coding Sequence | ATGGAGACTGGGCTGCGCTGGCTTCTCCTGGTCGC TGTGCTCAAAGGTGTCCAGTGTCAGCAGCAGCTGG AGGAGTCCGGGGGAGACCTGGTCAAGCCTGAGGGA TCCCTGACACTCACCTGCACAGCTTCTAAATTCTC CTTCAATAAGAAGTATTACATGTGCTGGGTCCGCC AGGCTCCAGGGAAGGGGCTGGAGTGGATCGGATG TGTTGATACTGGTGATGCTTTCATCGGCTACGCGA ACTGGGCGAAAGGCCGATTCACCGTCTCCAAAACC TCGTCGACCACGGTGGATCTGAAAATGACCAGTCT GACAGCCGCGGACACGGCCACCTATTTCTGTGCGA GAGGGGTTTATCCTATTAATACTGGTTATTACTAC TTTGACTTGTGGGGCCCAGGCACCCTGGTCACCGT CTCCTCA |

Table C-continued

| SEQ ID NO. | Description | Sequence |
|---|---|---|
| SEQ ID NO: 61 | Clone 163 VL DNA Coding Sequence | ATGGACACGAGGGCCCCCACTCAGCTGCTGGGGCT<br>CCTGCTGCTCTGGCTCCCAGGTGCCAGATGTGCCC<br>TTGTGATGACCCAGACTCCAGCCTCCGTGGAGGCA<br>GCTGTGGGAGGCACAGTCACCATCAAGTGCCAGG<br>CCAGTGAGGATATTACTAATTCTTTAGCCTGGTAT<br>CAGCAGAAACCAGGGCAGCCTCCCAACCTCCTGAT<br>CTACAGGGCATCCACTCTGGCATCTGGGGTCTCAT<br>CGCGGTTCAAAGGCAGTAGATCTGGGACAGAGTTC<br>ACTCTCACCATCAGCGGCGTGGAGTGTGCCGATGC<br>TGCCACTTACTACTGTCAACAGGGTTATAGTAGTA<br>CTAATGTTGATAATATTTTCGGCGGAGGGACCGAG<br>GTGGTGGTCAAA |

What is claimed is:

1. A polynucleotide encoding a heavy chain variable region (VH) of an antigen binding molecule that specifically binds to amino acid sequence GGGS (SEQ ID NO: 1); wherein the VH comprises the nucleotide sequence of SEQ ID NO: 56, 58 or 60.

2. A polynucleotide encoding a light chain variable region (VL) of an antigen binding molecule of claim 1; wherein the VL comprises the nucleotide sequence of SEQ ID NO: 57, 59, or 61.

3. A vector comprising the polynucleotide of claim 1 and claim 2.

4. A cell comprising the vector of claim 3.

5. A method of making an antigen binding molecule, comprising incubating the cell of claim 4 under suitable conditions to produce the antigen binding molecule.

* * * * *